(12) United States Patent
de Paz et al.

(10) Patent No.: US 11,613,775 B2
(45) Date of Patent: Mar. 28, 2023

(54) MEASURING DNA POLYMERASE FIDELITY

(71) Applicant: Northwestern University, Evanston, IL (US)

(72) Inventors: Alexandra M. de Paz, Evanston, IL (US); Keith E.J. Tyo, Evanston, IL (US)

(73) Assignee: Northwestern University, Evanston, IL (US)

(*) Notice: Subject to any disclaimer, the term of this patent is extended or adjusted under 35 U.S.C. 154(b) by 598 days.

(21) Appl. No.: 16/231,013

(22) Filed: Dec. 21, 2018

(65) Prior Publication Data

US 2019/0276882 A1 Sep. 12, 2019

Related U.S. Application Data

(60) Provisional application No. 62/608,811, filed on Dec. 21, 2017.

(51) Int. Cl.
*C12Q 1/6848* (2018.01)
*C12Q 1/686* (2018.01)

(52) U.S. Cl.
CPC ........... *C12Q 1/6848* (2013.01); *C12Q 1/686* (2013.01)

(58) Field of Classification Search
CPC .............................. C12Q 1/686; C12Q 1/6848
See application file for complete search history.

(56) References Cited

PUBLICATIONS

Lee, Mapping DNA polymerase errors by single-molecule sequencing, Nucleic Acids Research, 44(13): e188, pp. 1-9, 2016. (Year: 2016).*
Cadwell, Randomization of Genes by PCR Mutagenesis, PCR Methods and Applications, 2:28-33, 1992. (Year: 1992).*
Bebenek, The Effects of dNTP Pool Imbalances on Frameshift Fidelity during DNA Replication, Journal of Biological Chemistry 267(6): 3589-3596, 1992. (Year: 1992).*
Leung, A Method for Random Mutagenesis of a Defined DNA Segment using a Modified Polymerase Chain Reaction, Technique, 1:1, 11-15, 1989. (Year: 1989).*

* cited by examiner

*Primary Examiner* — Angela M. Bertagna
*Assistant Examiner* — Carolyn L Greene
(74) *Attorney, Agent, or Firm* — Foley & Lardner LLP

(57) ABSTRACT

Provided herein are systems and methods for high-resolution mapping of DNA polymerase fidelity using nucleotide imbalances and next-generation sequencing.

37 Claims, 65 Drawing Sheets
(64 of 65 Drawing Sheet(s) Filed in Color)
Specification includes a Sequence Listing.

DNA Polymerase Fidelity

Sequenase 2.0

AMV RT

Sequence Context Effects on Phi29 $FC_{50}$

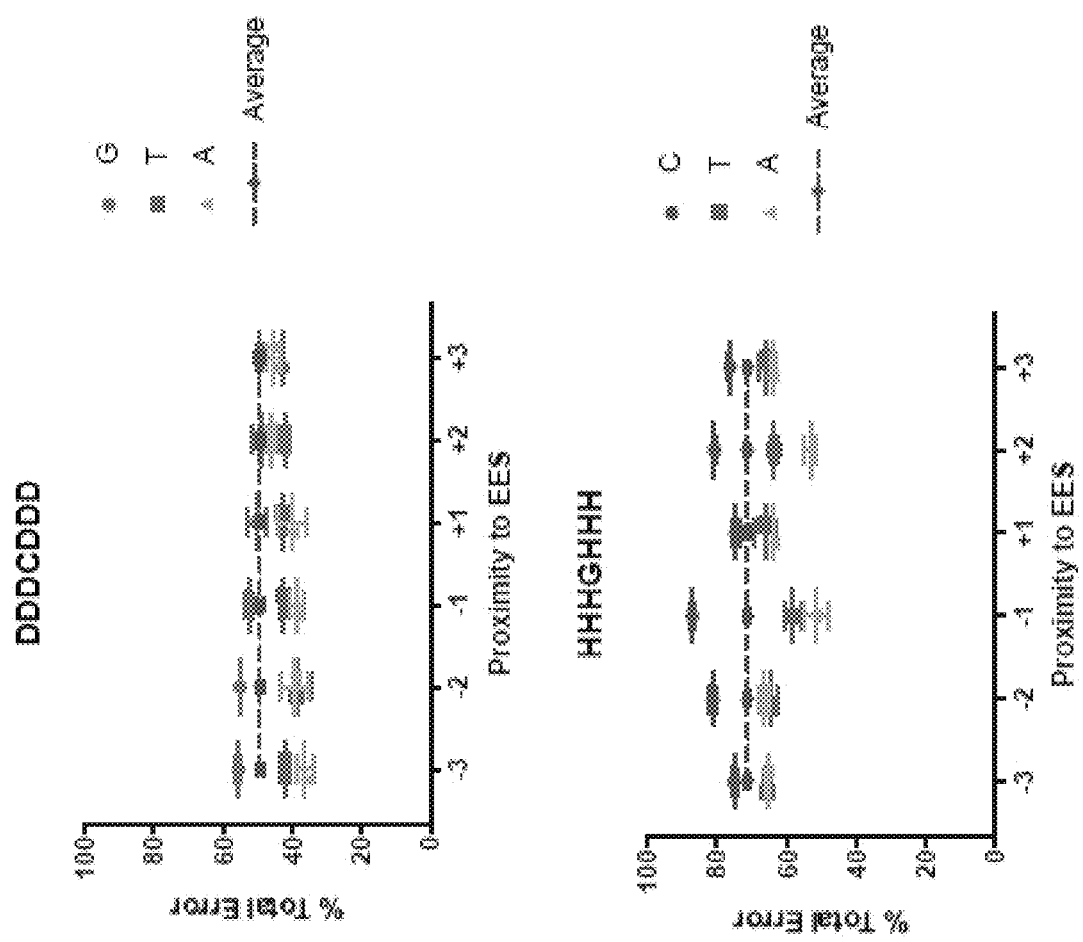

+1 Template Base Effects on Dpo4 Error Preference

Sequenase 2.0

AMV RT

Phi29

Taq

VVVTVVV

BBBABBB

DDDCDDD

HHHGHHH

VVVTVVV

BBBABBB

DDDCDDD

HHHGHHH

VVVTVVV

BBBABBB

DDDCDDD

HHHGHHH

VVVTVVV

BBBABBB

DDDCDDD

HHHGHHH

VVVTVVV

BBBABBB

DDDCDDD

HHHGHHH

Sequenase 2.0

AMV RT

Phi29

Taq

Dpo4

VVVTVVV

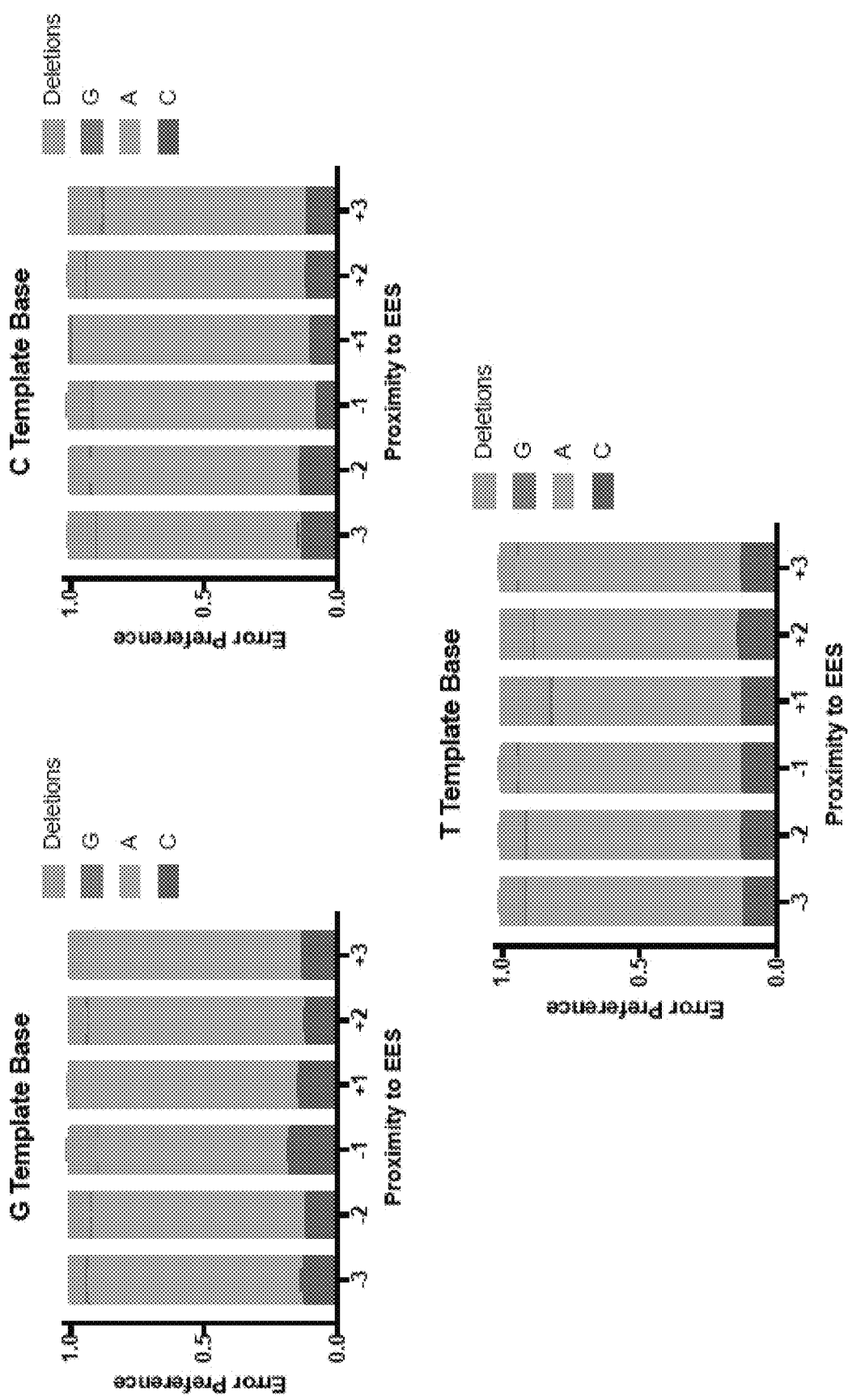

DDDCDDD

HHHGHHH

VVVTVVV

BBBABBB

DDDCDDD

HHHGHHH

VVVTVVV

BBBABBB

DDDCDDD

HHHGHHH

VVVTVVV

BBBABBB

DDDCDDD

HHHGHHH

VVVTVVV

BBBABBB

DDDCDDD

HHHGHHH

SEQUENCE LISTING

```
<160> NUMBER OF SEQ ID NOS: 8

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcatgctacc                                                                10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gctagcatgc                                                                10

<210> SEQ ID NO 3
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ggagaacacc caaaacaaca ccaaacagca aacaaaaagg agagagaaga avvvtvvvaa         60
ggaaaggaaa gaagcggaga cctatacaga cgactagccc                              100

<210> SEQ ID NO 4
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 4
ggtgttctcc cttttcttct cctttctcct ttcttttcc tgtgtgttgt tbbbabbbtt      60
ggtttggttt gttgcggtgt cctatacaga cgactagccc                           100

<210> SEQ ID NO 5
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
caacaactcc taactcaaca actaacatcc aacctttctc atatccacca ahhhghhhaa     60
ccaaaccaaa caacccaca cctatacaga cgactagccc                            100

<210> SEQ ID NO 6
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaagaagtgg taagtgaaga agtaagatgg aaggtgtgtg atatggagga adddcdddaa     60
ggaaaggaaa gaagggaaga cctatacaga cgactagccc                           100

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acactgacga catggttcta caatcaccag gtgtgggcta gtcgtctgta tagg           54

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agaccaagtc tctgctaccg ta                                              22
```

MEASURING DNA POLYMERASE FIDELITY

CROSS-REFERENCE TO RELATED APPLICATIONS

The present application claims the priority benefit of U.S. Provisional Patent Application 62/608,811, filed Dec. 21, 2017, which is incorporated by reference in its entirety.

STATEMENT REGARDING FEDERAL FUNDING

This invention was made with government support under MH103910 awarded by the National Institutes of Health. The government has certain rights in the invention

SEQUENCE LISTING

The instant application contains a Sequence Listing which has been filed electronically in ASCII format and is hereby incorporated by reference in its entirety. Said ASCII copy, created on May 10, 2019, is named 121384-0107 SL.txt and is 2,447 bytes in size.

FIELD

Provided herein are systems and methods for high-resolution mapping of DNA polymerase fidelity using nucleotide imbalances and next-generation sequencing.

BACKGROUND

DNA polymerase fidelity is critical to maintaining faithful replication of the genome (Ref. 1; herein incorporated by reference in its entirety). Despite their overall low frequency, DNA replication errors drive important biological phenomena like evolution and heritable disease genesis (Refs. 2-5; herein incorporated by reference in their entireties). During replication, DNA polymerases rely on built-in fidelity checkpoints, such as nucleotide selectivity and proofreading, to ensure faithful replication of genomic DNA (Refs. 1, 6, 7; herein incorporated by reference in their entireties). Beyond mechanisms intrinsic to the DNA polymerase, external factors such as mismatch repair, nucleotide supply, sequence context and other environmental modulators also influence fidelity outcomes (Refs. 2, 8-11; herein incorporated by reference in its entirety). In vivo, these factors influence a wide population of different DNA polymerases, each with their own fidelity characteristics (Refs. 12, 13; herein incorporated by reference in their entireties). The interplay between these different types of DNA polymerases and their corresponding in vivo replication environments can result in unique error signatures that have been difficult to pinpoint (Refs. 14-17; herein incorporated by reference in their entireties). Since the complexity of in vivo systems can obscure mechanistic insight into DNA polymerase fidelity, it is important to have robust methods for fidelity characterization that allow for dissection of key modulators in specified contexts.

In vitro forward mutation assays that link replication errors with phenotype upon introducing copied DNA into bacterial cells have been used for quantifying error rates of DNA polymerases. These commonly-used lacZ-based assays suffer from drawbacks such as: (a) lack of base-specific observations because only mutations that inactivate lacZ are reported, (b) low throughput as each assay requires significant effort and is not easily scaled, (c) limited capacity to interrogate sequence context effects on fidelity due to copying a defined reporter sequence (e.g., lacZ), and (d) additional sequencing steps to identify error subtypes (Refs. 18-20; herein incorporated by reference in their entireties). Alternatively, gel-based assays, such as denaturing gradient gel electrophoresis (DGGE), can be used to measure DNA polymerase fidelity. This method resolves products with fewer, dominant mutation types as opposed to a highly diverse mix of error-containing products, which requires repeated rounds of separation, purification, and sequencing (Refs. 21-23; herein incorporated by reference in their entireties). Ultimately, the low-throughput nature of both lacZ and DGGE mutation assays render these techniques suboptimal for assaying the impact of a multitude of conditions on fidelity.

High-throughput assays based on next-generation sequencing (NGS) have been successfully employed for direct detection of DNA polymerase errors (Refs. 23-28; herein incorporated by reference in their entireties). These approaches substantially improve throughput and data quality, and allow for fine-grained testing and analysis of fidelity in different sequence contexts. Even inherent limitations such as errors introduced during sample preparation and sequencing can be circumvented using different barcoding strategies (Refs. 23, 25-27; herein incorporated by reference in their entireties). However, NGS-based approaches require extensive sequencing (at least as many reads as the inverse of the error rate being measured) to identify naturally rare error events, limiting sample-scaling capacity within a fixed sequencing lane. Thus, these approaches do not scale economically when investigating the impact of a large set of conditions on DNA polymerase fidelity.

SUMMARY

Provided herein are systems and methods for high-resolution mapping of DNA polymerase fidelity using nucleotide imbalances and next-generation sequencing.

For example, in some embodiments, provided herein is a method comprising: (a) contacting a polymerase with: (i) at least one nucleic acid template primarily comprising three out of four of: (1) adenine (A), (2) cytosine (C), (3) guanine (G), and (4) thymine (T) or uracil (U) nucleotide types, wherein an error-enriched site (EES) on the nucleic acid template comprises the fourth nucleotide type; and (ii) nucleoside triphosphates (NTPs) for the four nucleotide types, wherein the complementary NTP for the EES is present at lower concentration than the complementary NTPs for the primary nucleic acid types of the nucleic acid template; (b) allowing the polymerase to synthesize a new nucleic acid strand from the nucleic acid template and NTPs; and (c) monitoring correct and/or errant incorporation (e.g., incorrect incorporation of nucleotide at the EES and/or an insertion/deletion at the EES). In some embodiments, incorporation of nucleotide and/or an insertion/deletion at the EES is monitored by nucleic acid sequencing. In some embodiments, incorporation of nucleotide and/or an insertion/deletion at the EES is monitored by a next-generation sequencing (NGS) technique. In some embodiments, the NGS technique is a single-molecule sequencing technique. In some embodiments, the nucleic acid template is deoxyribonucleic acid (DNA) or ribonucleic acid (RNA). In some embodiments, the NTPs are deoxyribonucleoside triphosphates (dNTPs) and the new nucleic acid strand is a DNA strand or ribonucleotides (rNTPs) and the new nucleic acid strand is an RNA strand. In some embodiments, the polymerase is a DNA polymerase, RNA polymerase, or reverse transcriptase. In some embodiments, (i) the primary nucleic acid types of the nucleic acid template are A, C, and G, and the EES is T or U; (ii) the primary nucleic acid types of the nucleic acid template are A, C, and T or U, and the EES is G; (iii) the primary nucleic acid types of the nucleic acid template are A, G, and T or U, and the EES is C; and/or (iv) the primary nucleic acid types of the nucleic acid template are C, G, and T or U, and the EES is A. In some embodiments, one or more nucleotides in the nucleic acid template are non-natural nucleic acids (e.g., one of the primary nucleic acids, the EES, etc.) and NTPs (e.g., natural, non-natural) used for synthesis/replication are compatible with synthesis from such nucleotides (Appella, Daniel H. Curr Opin Chem Biol. 2009 December; 13(5-6): 687-696; herein incorporated by reference in its entirety). In some embodiments, In some embodiments, the nucleotide type present at the EES is present at 5% or fewer of the positions of the nucleic acid template. In some embodiments, the nucleotide type present at the EES is not present elsewhere in the nucleic acid template. In some embodiments, the complementary NTPs for the primary nucleic acid types are present at concentrations between 10 and $10^9$ (10, 100, 1000, $10^4$, $10^5$, $10^6$, $10^7$, $10^8$, $10^9$, or ranges therebetween) greater than the complementary NTP for the EES. In some embodiments, a replication error results in a nucleotide substitution, insertion or deletion in the new nucleic acid strand. In some embodiments, the method further comprises: (d) repeating steps (a) through (c) with varied concentrations of the complementary NTP for the EES. In some embodiments, the method further comprises: (e) determining the concentration of the complementary NTP for the EES at which the polymerase makes a replication/synthesis error (e.g., incorrectly incorporates or makes an insertion/deletion) at the EES 50% of the time (e.g., the $FC_{50}$).

Certain embodiments provide a method comprising performing the steps of a method described herein for separate nucleic acid templates comprising each of the four nucleotide types at the EES. In some embodiments, the method comprises four separate reactions, each of which comprises a single one of each of the four nucleotide types at the EES. In some embodiments, at least one template comprises a plurality of different templates, wherein each of the templates comprises different nucleic acid sequences flanking the EES. In some embodiments, the flanking sequence comprises 1 to 9 nucleotides (e.g., 1, 2, 3, 4, 5, 6, 7, 8, 9, or ranges therebetween) on one or both sides of the EES (e.g., upstream (−) and/or downstream (+)).

In other embodiments, the present disclosure provides a kit, comprising: a plurality of nucleic acid templates, wherein each of the templates primarily comprises three out of four of: (1) adenine (A), (2) cytosine (C), (3) guanine (G), and (4) thymine (T) or uracil (U) nucleotide types, wherein an error-enriched site (EES) on the nucleic acid template comprises the fourth nucleotide type. In some embodiments, kits further comprise a plurality of nucleoside triphosphate (NTP) reagents, wherein each of the reagents comprises NTPs for the four nucleotide types, wherein the complementary NTP for the EES is present at lower concentration than the complementary NTPs for the primary nucleic acid types of the nucleic acid template. In some embodiments, each of the templates and each of the NTP reagents are present in separate containers. In some embodiments, the kit further comprises one or more additional components selected from, for example, buffers, analysis software, or one or more sequencing primers.

Additional embodiments are described herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A: The nucleotide imbalance fidelity assay relies on imbalanced dNTP pools (e.g. [dATP]<<< [dTTP, dCTP, dGTP]) to magnify native DNA polymerase error rates through forced misincorporation at a specified Error-Enriched Site (EES, e.g. T) on a template consisting of three bases (e.g. A, G, C). Rare base concentration can be tuned to a threshold where a low fidelity DNA polymerase preferentially creates replication errors but a high fidelity polymerase still correctly copies. Therefore, rare base concentration can be used to resolve differences in DNA polymerase fidelity. FIG. 1B: Each extension template (yellow) consists of a primer binding site (dark blue) and a 6-base combinatorial sequence context library (grey) flanking the EES (pink).

FIG. 2A: Simulation of the minimum number of sequencing reads required to accurately measure different error rates. Black line denotes a CV of 15%. FIG. 2B: Sensitivity of $FC_{50}$ values to sampling error and DNA polymerase stochasticity. Distribution of calculated $FC_{50}$ values for 1000 simulated rare base titration experiments, with each rare base condition receiving 50 simulated reads. Each condition was simulated by drawing 50 samples from a Bernoulli process with an underlying error rate equal to the experimentally derived error rate. $FC_{50}$ values were determined using the fitting procedure described in Methods. Histograms are shown for simulations based on Dpo4 (blue) and Phi29 (pink) error rates in a "T" template context. FIG. 2C: Determination of assay sample variability across different read counts. Error rate data collected for Dpo4 copying in all four template contexts reveal that error rate differences between 36 sets of biological replicates (n=2) do not vary with read count differences between the same set of biological replicates. FIG. 2D: Resolving power of the exemplary nucleotide imbalance fidelity assay based on $FC_{50}$ sensitivity. Minimum detectable fold change in $FC_{50}$ was determined based on the 95% confidence interval of the fitted $FC_{50}$ (see Table 3 for values). The ratio of the Upper Bound 95% CI: Fitted $FC_{50}$ was determined for Dpo4 copying in "T", "A", "C", and "G" template contexts.

FIG. 3A: Fidelity dose response curves of Sequenase 2.0, AMV RT, Phi29, Dpo4, and Taq copying in "T" template contexts. Values are the average of two experiments. Standard deviation error bars (n=2) are smaller than data points. Curves show qualitative agreement between DNA polymerase $FC_{50}$ values (indicated by black dotted line) and the expected rank order of natural DNA polymerase error rates (Table 4). In general, fidelity increases from right to left. FIG. 3B: Calibration between error rate and [$FC_{50}$]. A calibration curve relating multiple reported error rates per DNA polymerase (Table 4) and the average $FC_{50}$ value of each DNA polymerase (Table 3). Nonlinear fitting on a log-log plot (line of best fit in grey) revealed the following equation: $y=10^{(2.0631 \cdot log(x)+1.557)}$, RMSE=0.0008998 errors/bp.

FIGS. 6A-6C: Local sequence context effects on DNA polymerase fidelity. FIG. 6A: The identity and position of template bases neighboring a "T" EES impact the measured $FC_{50}$ of Phi29 copying in a VVVTVVV template context. Change in log $FC_{50}$ (log $FC_{50}$_Average–log $FC_{50}$_Fixed Template Base) was calculated for each base identity/position. Positive Δ log $FC_{50}$ values pertain to an increase in fidelity whereas negative values signify a decrease in fidelity. FIG. 6B: The identity and position of template bases flanking "C" and "G" EESs impact the % total error Phi29 creates at $10^{-7}$ µM dRTP when copying in DDDCDDD and HHHGHHH template contexts, respectively. A grey dotted line represents the average % total error made by Phi29 in a given context. FIG. 6C: Base identity at the +1 template position (in DDDCDDD, VVVTVVV, and BBBABBB contexts) impacts the distribution of Dpo4 error preferences (nucleotide substitutions and deletions). Error preference was determined by normalizing error subtype frequency to the total error rate measured at $10^{-7}$ µM dRTP. For all graphs shown in FIGS. 6A-6C, values represent the average of two experiments. Error bars signify standard deviation (n=2).

FIGS. 21A-21D: Effect of sequence context on Sequenase 2.0 error preference. The identity and position of template bases flanking "T", "A", "C" and "G" EESs impact the distribution of preferred errors (nucleotide substitutions and deletions) created by Sequenase 2.0 when copying in VVVTVVV (as shown in FIG. 21A), BBBABBB, (as shown in FIG. 21B) DDDCDDD (as shown in FIG. 21C), and HHHGHHH (as shown in FIG. 21D) template contexts, respectively. Error preference was determined by normalizing error subtype frequency to the total error rate measured at $10^{-7}$ μM dRTP. Values represent the average of two experiments. Error bars signify standard deviation (n=2).

DEFINITIONS

Figure 1A:
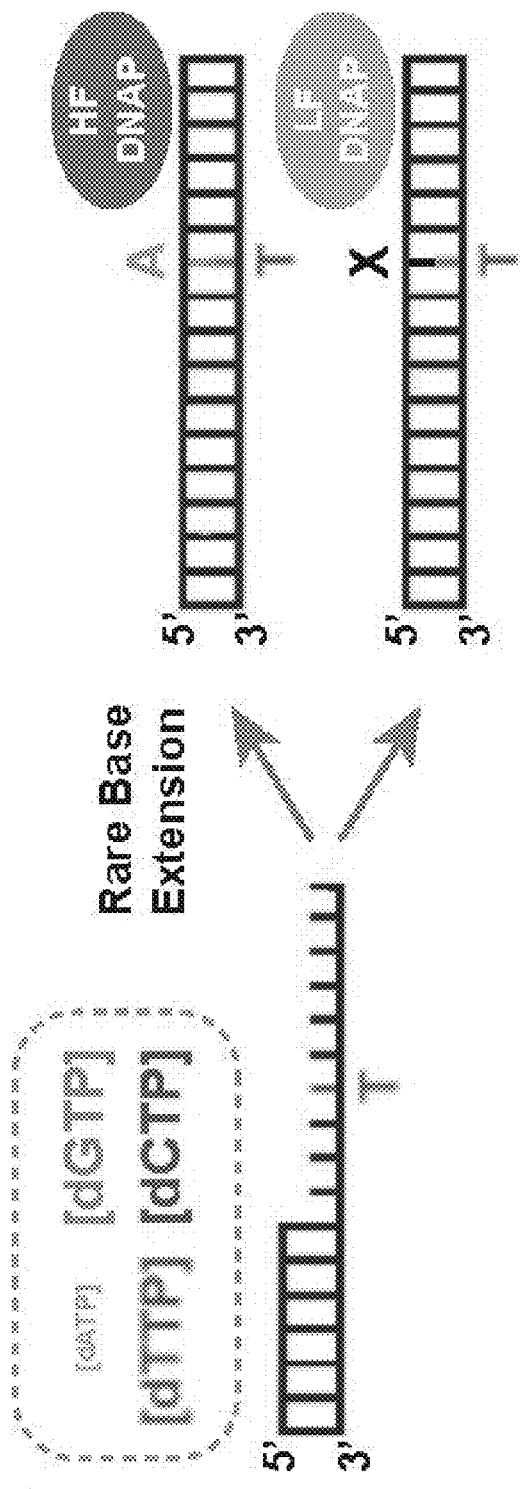
FIGS. 1A and 1B: Exemplary nucleotide imbalance fidelity assay concept.

The terminology used herein is for the purpose of describing the particular embodiments only, and is not intended to limit the scope of the embodiments described herein. Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a polymerase" is a reference to one or more polymerases and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "polymerase" refers to any enzyme suitable for use in the amplification of nucleic acids (e.g., DNA or RNA). It is intended that the term encompass prokaryotic and eukaryotic polymerases, RNA and DNA polymerases, reverse transcriptases, high-fidelity and error-prone polymerases, thermostable and thermolabile polymerases, etc.

As used herein, the term "DNA polymerase" refers to an enzyme which catalyzes the polymerization of deoxyribonucleoside triphosphates to make DNA chains using a nucleic acid template. Exemplary DNA polymerases that utilize a DNA template include prokaryotic family A polymerases (e.g., Pol I), prokaryotic family B polymerases (e.g., Pol II), prokaryotic family C polymerases (e.g., Pol III), prokaryotic family Y polymerases (e.g., Pol IV, Pol V), eukaryotic family X polymerases (e.g., Pol β, Pol λ, Pol σ and Pol µ), eukaryotic family B polymerases (e.g., Pol α, Pol δ, Pol ε, Pol ζ/Rev1), eukaryotic family Y polymerases (e.g., Pol η, Pol ι, and Pol κ), telomerase, eukaryotic family A polymerases (e.g., Pol γ and Pol θ), etc. DNA polymerases that are capable of utilizing an RNA template are "reverse transcriptases" ("RT"). Some RTs are also capable of utilizing DNA templates.

As used herein, the terms "replication error" and "synthesis error" refer to misincorporations, insertions, and deletions by a polymerase (See, e.g., Kunkel T A J Biol Chem. 2004 Apr. 23; 279(17):16895-8; Kunkel T A. Cold Spring Harb Symp Quant Biol. 2009; 74:91-101; herein incorporated by reference in their entireties).

As used herein, the term "oligonucleotide" (alternatively "oligo" or "oligomer refers to a molecule formed by covalent linkage of two or more nucleotides. Oligonucleotides are typically linear and about 5-50 (e.g., 5, 10, 15, 20, 25, 30, 35, 40, 45, 50, or ranges therebetween) nucleotides in length (although longer and shorter oligonucleotides may be within the scope of particular embodiments herein.

As used herein, the term "modified nucleotide" refers to nucleotides with sugar, base, and/or backbone modifications. Examples of modified nucleotides include, but are not limited to, locked nucleotides (LNA), ethylene-bridged nucleotides (ENA), 2'-C-bridged bicyclic nucleotide (CBBN), 2',4'-constrained ethyl nucleic acid called S-cEt or cEt, 2'-4'-carbocyclic LNA, and 2' substituted nucleotides. Examples of base modifications include deoxyuridine, diamino-2,6-purine, bromo-5-deoxyuridine, 5-methylcytosine, and the like. Nucleotide modifications can also be evident at the level of the internucleotide bond, for example phosphorothioates, H-phosphonates, alkyl phosphonates, etc.; and/or at the level of the backbone, for example, alpha-oligonucleotides, polyamide nucleic acids (PMA), 2'-O-alkyl-ribonucleotides, 2'-O-fluoronucleotides, 2'-amine nucleotides, arabinose nucleotides, etc.

As used herein, the term "sequence identity" refers to the degree two polymer sequences (e.g., peptide, polypeptide, nucleic acid, etc.) have the same sequential composition of monomer subunits. For example, if oligonucleotides A and B are both 20 nucleotides in length and have identical bases at all but 1 position, then peptide A and peptide B have 95% sequence identity. As another example, if oligonucleotide C is 20 nucleotides in length and oligonucleotide D is 15 nucleotides in length, and 14 out of 15 nucleotides in oligonucleotide D are identical to those of a portion of oligonucleotide C, then oligonucleotides C and D have 70% sequence identity, but oligonucleotide D has 93.3% sequence identity to an optimal comparison window of oligonucleotide C. For the purpose of calculating "percent sequence identity" (or "percent sequence similarity") herein, any gaps in aligned sequences are treated as mismatches at that position.

Any oligonucleotides described herein as having a particular percent sequence identity or similarity (e.g., at least 70%) with a reference sequence, may also be expressed as having a maximum number of substitutions (or terminal deletions) with respect to that reference sequence. For example, a sequence having at least Y % sequence identity (e.g., 90%) with SEQ ID NO:Z (e.g., 25 nucleotides) may have up to X substitutions (e.g., 2) relative to SEQ ID NO:Z, and may therefore also be expressed as "having X (e.g., 2) or fewer substitutions relative to SEQ ID NO:Z."

As used herein, the term "hybridization" and linguistic variations thereof (e.g., hybridize) refers to the binding or duplexing (e.g., via Watson-Crick, Hoogsteen, reversed Hoogsteen, or other base pair formation) of a nucleic acid molecule (e.g., oligonucleotide (e.g., primer)) to a sufficiently-complementary nucleotide sequence (e.g., template) under suitable conditions, e.g., under stringent conditions.

As used herein, the term "stringent conditions" (or "stringent hybridization conditions") refers to conditions under which an oligonucleotide (e.g., primer) will hybridize well to a perfectly complementary target sequence, to a lesser extent to less, but still significantly complementary sequences (e.g., 75% or greater complementarity), and not at all to, other non-complementary sequences.

As used herein, the term "complementary" (or "complementarity") refers to the capacity for pairing between two nucleotide sequences with each another. Nucleic acid strands (e.g., primer and template) are considered "sufficiently complementary" to each other when a sufficient number of bases in the nucleic acids are capable of forming hydrogen bonds (e.g., with complementary bases) to enable the formation of a stable complex between the strands. To be stable in vitro or in vivo the sequence of an oligonucleotide need not be 100% complementary to its target nucleic acid. The terms "complementary" and "specifically hybridisable" imply that the nucleic acids bind strongly and specifically to each other to achieve a desired effect (e.g., priming of a template). Nucleic acid strands (e.g., primer and template) are considered "perfectly complementary" to each other when all of the bases in one nucleic acid strand are capable of forming Watson-Crick base pairs with a contiguous segment of the other nucleic acid. For the purposes herein, percent complementarity is expressed and evaluated in a similar manner to percent identity, but considering only Watson-Crick pairs to be complementary (e.g., 5'-GCATGC-TACC-3' (SEQ ID NO: 1) is 90% complementary to 5'-GCTAGCATGC-3' (SEQ ID NO: 2)).

DETAILED DESCRIPTION

Provided herein are systems and methods for high-resolution mapping of DNA polymerase fidelity using nucleotide imbalances and next-generation sequencing.

Available techniques for measuring DNA polymerase error rate require trade-offs between scalability, error sensitivity (e.g., error subtype sensitivity), and flexibility in types of error-modulating conditions that can be tested. Provided herein are assays that combine high-throughput NGS with an error rate-amplification strategy that dramatically reduces the amount of sequencing reads required. Error rates increase proportionally to imbalances in nucleotide concentrations (Refs. 29-31; herein incorporated by reference in their entireties). Leveraging the nucleotide imbalance amplification of error rates, the use of nucleotide imbalances allows the assays described herein to amplify naturally low DNA polymerase error rates well above noise levels. Forced misincorporation through either limiting or completely withholding one or more nucleotides during replication has been employed previously for analysis of DNA polymerase fidelity and as a strategy for random and site-specific mutagenesis (Refs. 32-37; herein incorporated by reference in their entireties). In some embodiments, assays herein titrate the concentration of a designated "rare" base (dRTP) during synthesis until errors (e.g., base substitutions or single nucleotide deletions) are induced (FIG. 1A). Custom creation of extension templates by DNA synthesis allows design of the exact site that errors will be made (by synthesizing a template that only contains the complement to the dRTP at a specific location), and testing of the full combinatorial space of neighboring nucleotides to determine the effect of sequence context on the type and frequency of errors. By coupling the assays herein with a NGS readout, provided herein is a standardized platform for obtaining reproducible, high-resolution DNA polymerase fidelity profiles. Experiments conducted during development of embodiments herein measured five distinct DNA polymerases, spanning families A, B, Y, and RT and show strong agreement between fidelity outputs and literature-reported error rates. Assays herein are powerful tools for exploring the impact of local sequence context on error propensity and type. Experiments conducted during development of embodiments herein demonstrate robust methods for high-throughput interrogation of DNA polymerase fidelity.

Most DNA polymerases in nature rarely make mistakes (Ref. 51; herein incorporated by reference in its entirety), which makes accurate measurement of their fidelity dependent on many observations. To overcome this technical barrier, provided herein are assays that substantially magnify DNA polymerase error rates using imbalanced dNTP pools during extension, allowing for robust measurement of otherwise difficult-to-obtain values by tracking the concentration of the dRTP. This error-rate amplification strategy is coupled with a NGS readout, measuring DNA polymerase fidelity under varying levels of dNTP pool asymmetry. Through the assay, DNA polymerase $FC_{50}$ is calculated. $FC_{50}$ is a robust metric of polymerase fidelity which strongly correlates with DNA polymerase error rate while requiring far fewer sequencing reads for estimation, allowing for high-throughput determination of DNA polymerase fidelity.

In experiments conducted during development of embodiments herein, using a nucleotide imbalance fidelity assay, the fidelity properties of five DNA polymerases were examined and known fidelity trends for these polymerases were recapitulated based on the $FC_{50}$ metric. The polymerases tested included: two widely used commercial DNA polymerases (Taq, and Sequenase 2.0, a modified T7 polymerase without 3'-5' exonuclease activity), a reverse transcriptase (AMV RT) (Ref. 52; herein incorporated by reference in its entirety), a high fidelity polymerase with proofreading ability (Phi29) (Refs. 44-46; herein incorporated by reference in their entireties), and a low fidelity translesional polymerase (S. islandicus Dpo4) (Refs. 41-43; herein incorporated by reference in their entireties). Agreement with the literature demonstrate that nucleotide imbalance fidelity assays are a valid approach for rapidly assessing DNA polymerase fidelity. Beyond capturing general error rates, nucleotide imbalance fidelity assays also recapitulated known sequence context-dependent fidelity effects in a couple of the polymerases that were examined using a simple, generalizable template library approach. These results indicate a role for the nucleotide imbalance fidelity assay as a high-throughput tool in the DNA polymerase toolkit, alongside established measures of DNA polymerase fidelity (Refs. 18-28, 36; herein incorporated by reference in their entireties).

An advantage of using error rate magnification in combination with NGS is the scalability. Elevating DNA polymerase error rates means that far fewer observations are required for accurate estimates of polymerase error behavior. On top of this, it pushes error rates substantially above the baseline imposed by phosphoramidite synthesis (~0.05%-0.09%) (Refs. 26, 28; herein incorporated by reference in their entireties) and NGS (~0.1%) (Ref 53; herein incorporated by reference in its entirety), removing the need for more intricate error-correction methods (Refs. 23, 25-27; herein incorporated by reference in their entireties). In addition, NGS allows for substantially multiplexed samples using DNA barcoding. This makes nucleotide imbalance fidelity assays suitable for medium- to high-throughput investigations of DNA polymerase fidelity properties.

Compared to standard NGS approaches for measuring error rates, experiments conducted during development of embodiments herein demonstrate that to obtain an estimated, $FC_{50}$-based error rate of a moderate fidelity DNA polymerase (error rate of $10^{-5}$ errors/bp) using the assays herein, the required number of sequenced bases would be reduced by 250-fold. Assays would require sequencing of $4 \times 10^4$ bases compared to a required $\sim 10^7$ bases using other approaches. Additionally, if an objective were to simply analyze how DNA polymerase error preference changed across conditions, $FC_{50}$ calculation would not be necessary, and a single rare base condition where error rate is maximal (i.e. $10^{-7}$ µM dRTP) would suffice for determining error fraction. In this case, the required number of sequenced bases using the assay methods herein is reduced to 2000 bases per template type. Overall, the methods herein require substantially less sequencing coverage compared to standard NGS-based methods that rely on balanced dNTP levels.

Another advantage of amplifying errors is that sequencing reads are freed up that can be used to gain other types of fidelity information, such as how unique sequence contexts may change DNA polymerase error rate or preferred error type under any set of conditions. By embedding this information capacity in every rare base condition tested, these assays provide powerful tools for rapidly dissecting the effect of a particular sequence context on a given fidelity outcome. This is particularly useful since commonly used fidelity assays lack the flexibility to systematically evaluate the role of a particular sequence context in dictating error frequency and type. At the same time, by encoding a library of many different sequence contexts into each reaction, these assays circumvent potential sequence bias (which is inherent when a fixed extension template is used, like lacZ) by considering the average effect of sequence composition on polymerase error rate. Therefore, even without exploiting the built-in capacity to parse sequence effects, the assays herein reduce sequence bias, allowing the detection of errors that may be rare or even non-existent in commonly used template sequences. Nucleotide imbalance fidelity assays find use in, for example, substantiating proposed template-driven polymerase fidelity mechanisms and also facilitating discovery of sequence-based modulators of fidelity.

Using nucleotide imbalance fidelity assays herein, experiments conducted during development of embodiments herein demonstrated capture of a substantial number of DNA polymerase fidelity trends that were consistent with the known literature. This allowed establishment of rare base dose response curves as valid measurements of DNA polymerase fidelity. Further, it was also observed that a number of sequence context- and polymerase-dependent phenomena that suggested that the error-rate nucleotide imbalance fidelity magnification of the nucleotide imbalance fidelity assay was done in a relatively unbiased manner. Amplification of DNA polymerase errors was observed in the correct proportion to their natural error rates, revealing nucleotide imbalance fidelity error preferences that matched known DNA polymerase error preferences. For example, the assays correctly captured the general DNA polymerase preference for dGTP and dTTP misincorporations at T and G bases, respectively (Refs. 20, 22, 28, 37, 41, 54-57; herein incorporated by reference in their entireties). Polymerase-specific preferences such as AMV RT's unique tendency to misincorporate dCTP at A bases (Refs. 56, 58; herein incorporated by reference in their entireties) was also observed.

Experiments were conducted during development of embodiments herein to characterize a number of DNA polymerase fidelity characteristics that have not previously been interrogated. For instance, although base substitution preferences for exonuclease-deficient Phi29 have been previously measured (Ref. 46; herein incorporated by reference in its entirety), amplification of errors using a nucleotide imbalance fidelity assay herein detected Phi29 error preferences without having to disable 3'-5' proofreading. As a consequence, Phi29 fidelity was characterized in a more natural state, and sequence context-dependent fidelity phenomena were detected that supported previously cited sequence effects on 3'-5' exonuclease activity (Ref 9, 47-50; herein incorporated by reference in their entireties).

Another advantage of amplifying DNA polymerase errors through nucleotide imbalance fidelity assays is the observation of rare error subtypes that are not detectable by other assays. For example, traditional fidelity assays report T:dGTP mismatches as the dominant error preference of Taq polymerase (Ref. 20, 22, 54; herein incorporated by reference in their entireties), but are unable to report higher resolution of error preferences beyond that particular mismatch. The assays herein provide further detection of preferred mispairs at the three remaining types of template bases: A:dATP, C:dATP, and G:dTTP.

Reported polymerase error preferences are heavily biased by the sequence context used to measure them. For instance, discrepancies were observed in error preferences for Dpo4 at rare C sites (preference for C:dATP) and previous measurements that used a lacZ template (preference for C:dCTP) (Ref. 41; herein incorporated by reference in its entirety). However, further investigation of sequence context effects revealed the template-driven nature of that preference. Although, on average, Dpo4 preferred misincorporating dATP at "C" template sites, Dpo4 distinctly preferred C:dCTP in a context where +1 G flanked the EES. This +1 G-driven error preference, confirmed by the literature (Ref. 41, 43; herein incorporated by reference in their entireties), emphasized the importance of bias introduced by the template used to measure the fidelity of a DNA polymerase.

In addition to finding use in the study of DNA polymerase fidelity, the nucleotide imbalance fidelity assay platform described herein finds use in, for example, directed evolution of DNA polymerases, where a single rare base concentration, the $FC_{50}$ of a specified polymerase, could be supplied during extension to resolve high fidelity and low fidelity library variants, as even relatively small changes in a mutant's fidelity will result in a large change in error frequency near the $FC_{50}$. The use of the assays herein in such applications allows sorting of DNA polymerase mutants that produce a desired error response under any conditions of interest. Alternatively, implementing a cut-off rare base concentration independent of a parent polymerase's $FC_{50}$ reflects the desired level of fidelity of the target polymerase, providing user-defined fidelity to be selected and enriched for in a directed evolution scheme. In some embodiments, DNA polymerases with specified fidelity responses are evolved for applications including but not limited to DNA data storage (Ref. 59; herein incorporated by reference in its entirety), molecular recording (Ref. 28; herein incorporated by reference in its entirety), random mutagenesis (Ref. 60; herein incorporated by reference in its entirety), and DNA/RNA sequencing (Refs. 53, 61; herein incorporated by reference in their entireties).

The systems and methods described herein have numerous advantages over existing strategies for analyzing polymerase fidelity.

Since DNA polymerase error rates typically range from 1 error every 100 bases to 1 error every 100,000,000 bases (e.g., $1/10^2$, $1/10^3$, $1/10^4$, $1/10^5$, $1/10^6$, $1/10^7$, $1/10^8$, or ranges therebetween), it is difficult to reliably capture native error rate of polymerases with short templates using existing methods. However, because the methods and systems herein amplify the polymerase error rate, even a rare copying error can be detected on short (e.g., <1000, <750, <500, <250, <200, <150, <100 nucleotide) templates.

Although most embodiments herein are described for use with next-generation sequencing, the methods herein are compatible with any readout technique that detects single nucleotide polymorphisms (e.g., DNA sequencing, molecular beacon probes, peptide nucleic acids, TaqMan probes, etc.).

In some embodiments, the methods and systems herein allow for rapid identification of changes in polymerase error rate. The methods are more scalable than existing methods for measuring error rate of DNA polymerases. In some embodiments, the methods herein standardize the measurement of DNA polymerase fidelity (e.g., via $FC_{50}$), allowing for direct comparison between disparate DNA polymerases from different families.

In some embodiments, methods comprise the steps of: (a) contacting a polymerase with: (i) at least one nucleic acid template primarily comprising three out of four of: (1) adenine (A), (2) cytosine (C), (3) guanine (G), and (4) thymine (T) or uracil (U) nucleotide types, wherein an error-enriched site (EES) on the nucleic acid template comprises the fourth nucleotide type; and (ii) nucleoside triphosphates (NTPs) for the four nucleotide types, wherein the complementary NTP for the EES is present at lower concentration that the complementary NTPs for the primary nucleic acid types of the nucleic acid template; (b) allowing the polymerase to synthesize a new nucleic acid strand from the nucleic acid template and NTPs; and (c) monitoring correct and/or incorrect incorporation of nucleotide at the EES and/or an insertion/deletion at the EES. In some embodiments, the method further comprises: (d) repeating steps (a) through (c) with varied concentrations of the complementary NTP for the EES. In some embodiments, the method further comprises: (e) determining the concentration of the complementary NTP for the EES at which the polymerase makes a replication/synthesis error (e.g., incorrectly incorporates or makes an insertion/deletion) at the EES 50% of the time (e.g., the $FC_{50}$).

In some embodiments, methods comprise performing the steps of a method described herein for separate nucleic acid templates comprising each of the four nucleotide types at the EES. In some embodiments, the method comprises four separate reactions, each of which comprises a single one of each of the four nucleotide types at the EES. In some embodiments, at least one template comprises a plurality of different templates, wherein each of the templates comprises different nucleic acid sequences flanking the EES. In some embodiments, the flanking sequence comprises 1 to 3 nucleotides on one or both sides of the EES.

As described herein, the compositions and methods of the present disclosure utilize nucleic acid templates comprising three out of four of: (1) adenine (A), (2) cytosine (C), (3) guanine (G), and (4) thymine (T) or uracil (U) nucleotide types, wherein an error-enriched site (EES) on the nucleic acid template comprises the fourth nucleotide type. In some embodiments, (i) the primary nucleic acid types of the nucleic acid template are A, C, and G, and the EES is T or U; (ii) the primary nucleic acid types of the nucleic acid template are A, C, and T or U, and the EES is G; (iii) the primary nucleic acid types of the nucleic acid template are A, G, and T or U, and the EES is C; and/or (iv) the primary nucleic acid types of the nucleic acid template are C G, and T or U, and the EES is A. In some embodiments, the nucleotide type present at the EES is present at 5% or fewer of the positions of the nucleic acid template. In some embodiments, the nucleotide type present at the EES is not present elsewhere in the nucleic acid template.

In some embodiments, the nucleic acid template is deoxyribonucleic acid (DNA) or ribonucleic acid (RNA). In some embodiments, the template or the EES comprises one or more modified nucleotides. In some embodiments, a modified nucleotide having unique complementarity is present at the EES, and four standard nucleotides are present in the rest of the template. In such embodiments, complementary nucleotides for the four nucleotides are present at standard concentration and the complementary nucleotide for the modified nucleotide at the EES is rare.

The present disclosure is not limited to particular template lengths. In some embodiments, the template is 20-500 nucleotides in length (e.g., 20, 30, 40, 50, 60, 70, 80, 90, 100, 200, 300, 400, 500, or ranges therebetween), although other lengths are specifically contemplated.

In some embodiments, templates comprise regions of variation or degeneracy (e.g., 1, 2, 3, 4, 5, 6, or more) nucleotides flanking the EES. For example, in some embodiments, each template (e.g., A, C, G, and T/U EES) comprises a pool of templates with degeneracy flanking the EES. In some embodiments, the pool of templates comprises all possible combinations of nucleotides that are not the EES flanking the EES. In some embodiments, the following sequence context libraries are utilized: VVVTVVV, BBBABBB, DDDCDDD, and HHHGHHH (using IUPAC ambiguity codes). A Table of IUPAC ambiguity codes is provided below.

| IUPAC Code | Meaning | Complement |
|---|---|---|
| A | A | T |
| C | C | G |
| G | G | C |
| T/U | T | A |
| M | A or C | K |
| R | A or G | Y |
| W | A or T | W |
| S | C or G | S |
| Y | C or T | R |
| K | G or T | M |
| V | A or C or G | B |
| H | A or C or T | D |
| D | A or G or T | H |
| B | C or G or T | V |
| N | G or A or T or C | N |

In some embodiments, templates for each nucleotide (e.g., with or without degeneracy) are provided for use in multiple (e.g., 4) primer extension reactions.

In some embodiments, particularly depending upon the sequencing technique used, templates comprise labels, handles, or other tags. In some embodiments, template labeling/tagging facilitates sequencing. In some embodiments, a tag facilitates immobilization of the template on a solid surface (e.g., to facilitate sequencing).

In some embodiments, assays comprise nucleoside triphosphates (NTPs) for the four nucleotide types, wherein the complementary NTP for the EES is present at lower concentration than the complementary NTPs for the primary nucleic acid types of the nucleic acid template. In some embodiments, the NTPs are deoxyribonucleoside triphosphates (dNTPs) or ribonucleotides (rNTPs) or modified versions thereof. In some embodiments, the complementary NTPs for the primary nucleic acid types are present at concentrations between 10 and $10^9$ (e.g., 10, 100, 1000, $10^5$, $10^6$, $10^7$, $10^8$, or $10^9$) times greater than the complementary NTP for the EES.

In some embodiments, particularly depending upon the sequencing technique used, nucleotides comprise labels. In some embodiments, nucleotide labeling facilitates detection/identification of the nucleotide incorporated at any position along the template (e.g., correct or incorrect incorporation at the EES).

In some embodiments, one or more steps of methods herein (e.g., template amplification, monitoring polymerase fidelity, rare base incorporation, etc.) utilize one or more primers. In some embodiments, templates for use in the systems and methods herein comprise primer binding sequences, and the binding of a complementary primer to the primer binding region of the template facilitates synthesis of a new nucleic acid strand by the polymerase on the template.

In some embodiments, a primer is at least 60% (e.g., 60%, 65%, 70%, 75%, 80%, 85%, 90%, 95%, 100%, or ranges therebetween) complementary to a primer binding region of a template. In some embodiments, assays utilize a single primer that generates a single amplicon of variable length. In some embodiments, assays utilize two primers that each anneal to opposite strands of the template and generate an amplicon of determinate length.

In some embodiments, particularly depending upon the sequencing technique used, primers comprise labels, handles, or other tags. In some embodiments, primer labeling/tagging facilitates sequencing of the new strand generated therefrom. In some embodiments, primers are attached to a solid surface; thereby facilitating immobilization of the nucleic acid synthesis.

In some embodiments, the assays herein utilize nucleic acid sequencing to monitor polymerase fidelity under imbalanced nucleotide conditions. Nucleic acid molecules may be sequence analyzed by any number of techniques. Illustrative non-limiting examples of nucleic acid sequencing techniques include, but are not limited to, chain terminator (Sanger) sequencing and dye terminator sequencing, as well as "next generation" sequencing (NGS) techniques. In particular embodiments, single molecule sequencing techniques are utilized as they allow robust resolution of different error subtypes created by a DNA polymerase of interest, and detection of single molecule events. The use of NGS and/or single molecule techniques allows counting of every incorporation event and quantification of the fraction of those events that are errors vs. correct incorporations, and then further determination of the composition of those errors (e.g., all possible nucleotide substitutions, deletions, insertions, etc.).

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833.246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), the Adessi PCR colony technology (Adessi et al. (2000). Nucleic Acid Res. 28, E87; WO 00018957; herein incorporated by reference in its entirety), and suitable combinations or alternatives thereof.

A set of methods referred to as "next-generation sequencing" techniques have emerged as alternatives to Sanger and dye-terminator sequencing methods (Voelkerding et al., Clinical Chem., 55: 641-658, 2009; MacLean et al., Nature Rev. Microbiol., 7: 287-2%; each herein incorporated by reference in their entirety). Next-generation sequencing (NGS) methods share the common feature of massively parallel, high-throughput strategies, with the goal of lower costs and higher speeds in comparison to older sequencing methods. NGS methods can be broadly divided into those that require template amplification and those that do not.

Sequencing techniques that find use in embodiments herein include, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/$cm^2$. The flow cell is then loaded into a sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), each of which is incorporated by reference in their entireties.

Another example of a DNA sequencing technique that finds use in embodiments herein is 454 sequencing (Roche) (Margulies, M et al. 2005, Nature, 437, 376-380; incorporated by reference in its entirety). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments are attached to DNA capture beads, e.g., streptavidin-coated beads using, e.g., Adaptor B, which contains a 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that finds use in embodiments herein is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that finds use in embodiments herein is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982; incorporated by reference in their entireties). In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton ($H^+$), which is detected and recorded in a sequencing instrument. The signal strength is proportional to the number of nucleotides incorporated.

Another example of a DNA sequencing technique that finds use in embodiments herein is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a DNA sequencing technique that finds use in embodiments herein is the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a DNA sequencing technique that finds use in embodiments herein involves nanopore sequencing (Soni G V and Meller A. (2007) Clin Chem 53: 1996-2001; incorporated by reference in its entirety). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a DNA sequencing technique that finds use in embodiments herein involves using a chemical-sensitive field effect transistor (chemFET) array to sequence DNA (for example, as described in US Patent Application Publication No. 20090026082; incorporated by reference in its entirety). In one example of the technique, DNA molecules can be placed into reaction chambers, and the template molecules can be hybridized to a sequencing primer bound to a polymerase. Incorporation of one or more nucleoside triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In some embodiments, other sequencing techniques (e.g., NGS techniques) understood in the field, or alternatives or combinations of the above techniques find use in embodiments herein.

In some embodiments, the assays herein utilize single-molecule, highly-multiplexed, and/or high-throughput samples and techniques. In some embodiments, DNA barcoding of nucleic acid templates facilitates analysis of the substantial data collected in the assays herein. In certain embodiments, sequencing components that employ barcoding for labelling individual nucleic acid molecules are employed. Examples of such barcoding methodologies and reagents are found in, for example, U.S. Pat. Pub. 2007/0020640, U.S. Pat. Pub. 2012/0010091, U.S. Pat. Nos. 8,835,358, 8,481,292, Qiu et al. (Plant. Physiol., 133, 475-481, 2003), Parameswaran et al. (Nucleic Acids Res. 2007 October; 35(19): e130), Craig et al. reference (Nat. Methods, 2008 Oct. 5(10):887-893), Bontoux et al. (Lab Chip, 2008, 8:443-450), Esumi et al. (Neuro. Res., 2008, 60:439-451), Hug et al., J. Theor., Biol., 2003, 221:615-624), Sutcliffe et al. (PNAS, 97(5):1976-1981; 2000), Hollas and Schuler (Lecture Notes in Computer Science Volume 2812, 2003, pp 55-62), and WO201420127; all of which are herein incorporated by reference in their entireties, including for reaction conditions and reagents related to barcoding and sequencing of nucleic acids.

In further embodiments, the present disclosure provides a kit, comprising: a) a plurality of nucleic acid templates, wherein each of the templates primarily comprises three out of four of: (1) adenine (A), (2) cytosine (C), (3) guanine (G), and (4) thymine (T) or uracil (U) nucleotide types, wherein an error-enriched site (EES) on the nucleic acid template comprises the fourth nucleotide type; and b) a plurality of nucleoside triphosphate (NTP) reagents, wherein each of the reagents comprises NTPs for the four nucleotide types, wherein the complementary NTP for the EES is present at lower concentration than the complementary NTPs for the primary nucleic acid types of the nucleic acid template. The various components of the kit optionally are provided in suitable containers. In some embodiments, each of the templates and each of the NTP reagents are present in separate containers. Where appropriate, the kit may also optionally contain reaction vessels, mixing vessels and other components that facilitate the preparation of reagents or the test polymerase.

In some embodiments, the kit further comprises one or more additional components selected from, for example, buffers, analysis software, or one or more sequencing primers. Optionally, the kit can also contain at least one calibrator or control. Any calibrator or control can be included in the kit. The kit further can optionally include instructions for use, which may be provided in paper form or in computer-readable form, such as a disc, CD, DVD or the like.

The assays and platforms described herein find use in a variety of applications. In some embodiments, provided herein are medium-to-high throughput fidelity screening of DNA polymerases, for the purposes of directed evolution, rational design, etc. In some embodiments, provided herein are systems and methods in which amplification of polymerase error rate is a marker for one or more environmental cues/signals such as metal ion concentration, temperature, pH, light, or any type of small molecule/protein ligand interaction being recorded by the polymerase (e.g., a polymerase that has been found to have altered error rate/type in the presence/absence of such cues/signals). In some embodiments, systems and methods herein find use in recording/deciphering information encoded in nucleic acids (for signal recording purposes or otherwise). In some embodiments, assays herein are used to screen the effects of sample conditions and/or another environment (e.g. metal type/concentration), template composition (e.g. sequence context), and enzyme structure on DNA polymerase fidelity. In some embodiments, systems herein (e.g., polymerases with characteristics identified using the assays herein) find use as biosensors, molecular recording devices (neural recording application). In some embodiments, assays find use in identifying polymerases for use in particular applications, such as DNA polymerase directed evolution/engineering (e.g. DNA polymerases that can copy unnatural bases/sugar backbones, XNAs, DNA polymerases for PCR, lesion repair, random mutagenesis, etc.). In some embodiments, the assays and systems herein find use in the development of polymerase-based tools. Other uses and applications for the assays herein and polymerases screened or identified using the platforms herein are within the scope of the present invention.

EXPERIMENTAL

Materials and Methods
DNA Polymerases

Enzymes and corresponding reaction buffers were commercially obtained (Table 1). Purified Taq polymerase, Avian Myeloblastosis Virus (AMV) RT, Phi29, and *Sulfolobus islandicus* Dpo4 were purchased through New England Biolabs. Purified Sequenase 2.0 was purchased through Affymetrix.

TABLE 1

DNA polymerase extension reaction conditions.

| DNA Polymerase | Enzyme Units/Reaction | Reaction Buffer | Supplier(s) | Incubation Temperature |
|---|---|---|---|---|
| Sequenase2.0 | 3.25 | 5X Sequenase Reaction Buffer | Affymetrix | 37° C. |
| AMV Reverse Transcriptase (AMV RT) | 6.25 | 10X AMV Reverse Transcriptase Reaction Buffer | New England Biolabs | 37° C. |
| Phi29 | 5.00 | 10X Phi28 DNA Polymerase Reaction Buffer | New England Biolabs | 30° C. |
| Taq | 1.00 | 10X Standard Taq Reaction Buffer | New England Biolabs | 68° C. |
| *S. Isiandicus* DNA Polymerase IV (Dpo4) | 1.00 | 10X REC Buffer 15 (extension reactions were supplemented with 10 mM MgCl$_2$) | New England Biolabs (enzyme); Trevigen (buffer) | 37° C. |

Extension Template Design

Extension templates ($T_T$, $T_A$, $T_C$, and $T_G$) were designed for all four rare base contexts (Table 2). Templates were 100 bp in length and contained a single T, A, C, or G, or Error-Enriched Site (EES), near the middle of the template. Extension templates were designed to contain only three bases, with the exception of the EES (fourth base) and the extension primer-binding site. For each template type, the EES was flanked by 3 degenerate bases before the EES and 3 degenerate bases after the EES in order to create the following sequence context libraries: VVVTVVV, BBBA-BBB, DDDCDDD, and HHHGHHH (using IUPAC ambiguity codes). Because each of the 6 degenerate sites can be composed of 3 possible bases, each template library contained 729 ($3^6$) unique sequence contexts surrounding the EES. With the exception of the 6 bases flanking the EES, template sequences within a given library were identical. All templates contained a 3' dideoxy-C modification to prevent extension from the template strand during a final PCR amplification step. Extension templates were purified via PAGE (Integrated DNA Technologies).

TABLE 2

DNA sequences used in the exemplary nucleotide imbalance fidelity assays. Table discloses SEQ ID NOS 3-8, respectively, in order of appearance.

| Sequence Name | DNA Sequence (5'- 3') |
|---|---|
| $T_T$ | GGAGAACACCCAAAACAACACCAAACAGCAAACAAAAAGGA GAGAGAAGAAVVVTVVVAAGGAAAGGAAAGAAGCGGAGACC TATACAGACGACTAGCC/3ddC/ |

TABLE 2-continued

DNA sequences used in the exemplary nucleotide imbalance fidelity assays. Table discloses SEQ ID NOS 3-8, respectively, in order of appearance.

| Sequence Name | DNA Sequence (5'- 3') |
|---|---|
| $T_A$ | GGTGTTCTCCCTTTTCTTCTCCTTTCTCCTTTCTTTTTCCT GTGTGTTGTTBBBABBBTTGGTTTGGTTTGTTGCGGTGTCC TATACAGACGACTAGCC/3ddC/ |
| $T_G$ | CAACAACTCCTAACTCAACAACTAACATCCAACCTTTCTCA TATCCACCAAHHHGHHHAACCAAACCAAACAACCCCACACC TATACAGACGACTAGCC/3ddC/ |
| $T_C$ | GAAGAAGTGGTAAGTGAAGAAGTAAGATGGAAGGTGTGTGA TATGGAGGAADDDCDDDAAGGAAAGGAAAGAAGGGAAGACC TATACAGACGACTAGCC/3ddC/ |
| $P_{EXT}$ | ACACTGACGACATGGTTCTACAATCACCAGGTGTGGGCTAG TCGTCTGTATAGG |
| CS2 | /5Phos/AGACCAAGTCTCTGCTACCGTA |

Primer Design

A universal extension primer ($P_{EXT}$) was designed to bind to all assay templates ($T_T$, $T_A$, $T_C$, and $T_G$) and was used for all polymerase extension reactions. From 5'-3', the primer contained a 22-base universal tag called common sequence 1 (CS1) of the Fluidigm Access Array Barcode Library for Illumina Sequencers (Fluidigm), a 12 base DNA barcode, and 20 bases of homology with the template (Table 2). To enable assay scalability, a DNA barcode was built into $P_{EXT}$ as a placeholder to allow dual-barcoding of reactions for experimental set ups requiring multiplexing beyond 384 reaction conditions. A library of 2,168 barcodes has been published by Caporaso et al. (Ref 38; herein incorporated by reference in its entirety). $P_{EXT}$ was purified via standard desalting (Integrated DNA Technologies).

Nucleotide Imbalance Fidelity Assay

Individual annealing reactions were performed for each template type ($T_T$, $T_A$, $T_C$, $T_G$). Primer/template DNA was prepared by mixing $P_{EXT}$ with each template library in a 1:1.5 molar ratio (70 nM primer: 105 nM template) in a 1× reaction buffer specific to each DNA polymerase being tested (Table 1). The extension primer was annealed to template DNA by incubation at 95° C. for 2 minutes, followed by a −0.1° C./sec ramp until reaching 4° C.

Primer extension reactions were set up in duplicate for each condition being tested. Biological replicate reactions were performed in parallel, with the same annealed primer/template sample used for both replicates. For each DNA polymerase and rare base context of interest, 9 rare base concentrations were tested (log-fold dilutions from 10 µM-0.1 pM) while the concentration of the 3 non-rare bases was held constant at 10 µM (Bioline). Due to the nature of commercial dNTP manufacturing, a zero [dRTP] condition revealed contaminating trace levels of dRTP in non-rare base stocks. Although trace dRTP contamination could impact the true concentration of dRTP propagated in each dilution series, it was concluded that since the same dNTP stocks were used for each reaction, potential contaminating effects were systematic and did not affect the $FC_{50}$ estimate.

Primer extension reactions consisted of 1 µL of annealing reaction, 1× dNTP stocks (10 non-rare bases+variable [dRTP]), variable DNA polymerase units, and 1×DNA polymerase reaction buffer in a 10 µL reaction. Extension reaction conditions for DNA polymerases tested are described in Table 1. Extension reactions were incubated for 1 hour and stored at −20° C. until purification. The Fluent Automated Liquid Handling Platform (Tecan) was used to set up all primer extension reactions.

Illumina Library Preparation and Sequencing

The sample preparation pipeline for NGS was adapted from a previous protocol (Ref. 28; herein incorporated by reference in its entirety). Products from individual rare base extension reactions were column purified in 96-well plate format using the ZR-96 DNA Clean & Concentrator-5 (Deep well format) kit (Zymo Research). Purified DNA products were eluted in 10 µL of water and stored at −20° C. until ligation. Next, a 22 bp universal tag, common sequence 2 (CS2) of the Fluidigm Access Array Barcode Library for Illumina Sequencers (Fluidigm), synthesized as duplex DNA with a 5' phosphate modification and PAGE purified (Integrated DNA Technologies, Table 2) was blunt-end ligated to the 3' end of extended products. Ligation reactions were carried out in 10 µL volumes and consisted of 6 µL of purified product, 30 nM CS2 duplex DNA, 1× T4 DNA Ligase Reaction Buffer (New England Biolabs), and 2000 Units of T4 DNA Ligase (New England Biolabs). Ligation reactions were incubated at 16° C. for 16 hours. Ligated products were stored at −20° C. until PCR.

PCR was performed with barcoded primer sets from the Access Array Barcode Library for Illumina Sequencers (Fluidigm) to label extension products from up to 384 individual reactions. Each PCR primer set contained a unique barcode in the reverse primer. From 5'-3', the forward PCR primer (PE1_CS1) contained a 25 base paired-end Illumina adapter 1 sequence followed by CS1. The binding target of the forward PCR primer was the reverse complement of the CS1 tag built into $P_{EXT}$. From 5'-3', the reverse PCR primer (PE2_BC_CS2) was a 24 base paired-end Illumina adapter 2 sequence, a 10 base Fluidigm barcode, and the reverse complement of CS2. CS2 DNA that had been ligated onto the 3' end of extended products served as the reverse PCR primer-binding site.

Each PCR reaction contained 2 µL of ligation product, 1× Phusion High-Fidelity PCR Master Mix with HF Buffer (New England Biolabs), and 400 nM forward and reverse Fluidigm PCR primers in a 20 µL reaction volume. Products were initially denatured for 30 seconds at 98° C., followed by 20 cycles of 10 seconds at 98° C. (denaturation), 30 seconds at 60° C. (annealing), and 30 seconds at 72° C. (extension). Final extensions were performed at 72° C. for 10 minutes. Amplified products were stored at −20° C. until clean up and pooling. All ligation and PCR reactions were performed in 96-well plate format. The Fluent Automated Liquid Handling Platform (Tecan) and Mosquito Crystal (TTP Labtech) were used to set up all reactions.

The SequalPrep Normalization 96-well Plate Kit (ThermoFisher Scientific) was used to clean up and normalize the recovery of PCR reaction products up to 25 ng per reaction. Normalized, barcoded products were pooled together to form a library. AMPure XP beads (Beckman Coulter) were used to concentrate each product library 10-fold. Concentrated libraries were analyzed using a 2200 TapeStation (Agilent) to determine size and quality. Concentration of each library was measured using a Qubit 2.0 Fluorometer (Life Technologies). Sequencing was performed using a MiSeq v2 500 cycle kit on a MiSeq Benchtop Sequencer (Illumina). A 15% phiX DNA control was spiked in alongside product libraries during sequencing. Fluidigm sequencing primers, targeting the CS1 and CS2 linker regions, were used to initiate sequencing. De-multiplexing of reads was performed on instrument based on Fluidigm barcodes.

Library concentration, quality analysis, and quantification were performed at the DNA services (DNAS) facility, Research Resources Center (RRC), University of Illinois at Chicago (UIC). Sequencing was performed at the W.M. Keck Center for Comparative and Functional Genomics at the University of Illinois at Urbana-Champaign (UIUC).

Error Rate Analysis

Forward and paired-end sequences were obtained in FASTQ format. Forward sequences were filtered for exact matches to the extension primer and CS2 sequences, as well as for the presence of a corresponding paired-end read. The sequence from the start of the read to the beginning of the Fluidigm reverse PCR primer was isolated, leaving only the sequence corresponding to the extension product. Reads in which the paired-end read did not contain the exact reverse complement of this extension sequence were discarded. Next, reads where any base call in this sequence had a quality score below 20 were discarded. This sequence was then aligned to the expected sequence using the Needleman-Wunsch algorithm and sequences that had an alignment score outside of a specified set of cutoffs (using the EDNA-FULL scoring matrix, a gap-opening penalty of 10, and a gap-extension penalty of 0.5) were filtered for alignments with scores between 300 and 1000 (Refs. 39, 40; herein incorporated by reference in their entireties). Extension sequences that were shorter than 70 bp or longer than 150 bp were discarded.

Extension sequences were indexed based on their alignments to the expected template sequence. To determine error rates at EESs, occurrences of the correct incorporation or error of interest at the given EES were counted and divided by the total number of reads that passed the filtering procedure. Calculated errors included nucleotide substitutions and deletions (e.g., single nucleotide deletions) at the EES. Descriptive statistics for experimental error rates were calculated over the results of two biological replicates.

Mean DNA polymerase error rate data was collected in biological duplicate at 9 concentrations of the rare base (log-fold [dRTP] dilutions from 10 μM-0.1 pM) for each template type tested. To obtain a rare base titration curve, log[dRTP] was plotted against mean error rates (n=2) using nonlinear regression. Sampling error between replicates was plotted using standard deviation values. Curves were fit to a dose-response equation accounting for variable slope, four parameters, and a least squares (ordinary) fit. From each nonlinear fit the concentration of rare base was determined that yields the half maximal error rate, Fidelity Concentration-50 ($FC_{50}$), as well as 95% confidence intervals for $FC_{50}$, and R-squared values.

Error Rate Measurement Simulations

To estimate the coefficient of variation (CV), $$\frac{\sigma}{\mu},$$

for a given error rate estimate, it was assumed that the number of errors present in a given sample, X, was distributed as X~Binomial (n, p), where n is the number of sequencing reads in the sample and p is the underlying DNA polymerase error rate. The error rate estimator $$\frac{X}{n}$$

has variance $$\frac{p(1-p)}{n};$$

thus, the CV for the error rate estimator is $$\sqrt{\frac{1-p}{np}}.$$

The CV was calculated for error rates and read counts representative of potential NGS-based experiments analyzing various natural DNA polymerases.

$FC_{50}$ Simulations

For $FC_{50}$ sensitivity analysis, 1000 rare base titration curve experiments were simulated for both Dpo4 and Phi29 copying in a "T" template context. For each rare base condition, sequencing results based on 50 sequencing reads were simulated by drawing 50 samples from a Bernoulli process with a true error rate equivalent to the experimentally derived value. A $FC_{50}$ value was then determined for each simulated experiment using the fitting procedure described previously.

Mapping $FC_{50}$ onto Literature Error Rates

For each DNA polymerase, an average $FC_{50}$ value was plotted against several literature error rates to enable calibration of $FC_{50}$ with error rate. Nonlinear regression was performed on a log-log plot using a least squares (ordinary) fit and the following equation: $y=10^{(slope*log(x)+y\text{-}intercept)}$. Nonlinear fitting between literature error rates and $FC_{50}$ revealed the following equation: $y=10^{(2.063\ log(x)+1.557)}$ with an RMSE of 0.0008998 errors/bp.

Predicted Error Rate Derivation

In order to relate [$FC_{50}$] to error rate, a first order rate law was used to describe the system. The rate of incorrect incorporation ($r_{inc}$) was defined using the following equation:

$$r_{inc}=k_{inc}[\text{inc}] \tag{1}$$

where $k_{inc}$ is an intrinsic rate constant for misincorporation and [inc] is the concentration of incorrect base. Similarly, the rate of correct base incorporation ($r_{corr}$) was defined as follows:

$$r_{corr}=k_{corr}[\text{corr}] \tag{2}$$

where $k_{corr}$ is an intrinsic rate constant for correct incorporation and [corr] is the concentration of correct base. The probability of misincorporation was defined as follows:

$$P_{inc} = \frac{r_{inc}}{r_{corr}+r_{inc}} \text{ or} \tag{3}$$

$$P_{inc} = \frac{k_{inc}[inc]}{k_{corr}[corr]} \tag{4}$$

where $r_{inc} \lll r_{corr}$ and therefore negligible. At the [$FC_{50}$], (1) is equal to (2) as follows:

$$k_{corr}[FC_{50}]=k_{inc}[\text{inc}] \tag{5}$$

Equation (5) was substituted into equation (4) to obtain the following relationship between [$FC_{50}$] and error rate:

$$P_{inc} = \frac{k_{corr}[FC_{50}]}{k_{corr}[corr]} \text{ or} \quad (6)$$

$$P_{inc} = \frac{[FC_{50}]}{[corr]} \quad (7)$$

Under equimolar dNTP conditions:

$$[inc]=[corr]=10 \text{ μM} \quad (8)$$

Therefore, the following equation was used to obtain predicted error rates:

$$P_{inc}=0.1 \text{ μM}^{-1}[FC_{50}] \quad (9)$$

Sequence Context Analysis

The three bases before (−3, −2, −1) the EES and the three bases after (+1, +2, +3) the EES were analyzed for their fidelity impact at the EES. Reads were identified based on the composition of the −3, −2, −1, +1, +2, and +3 bases flanking the EES and the counts of each error (or correct incorporation) at the EES were determined for each possible 6-base identity. Counts over all possible 6-base sequences were then aggregated by base identity and position surrounding the EES and error rates for each base identity and neighboring position were calculated.

Results

Nucleotide Imbalance Fidelity Assay

Figure 1B:
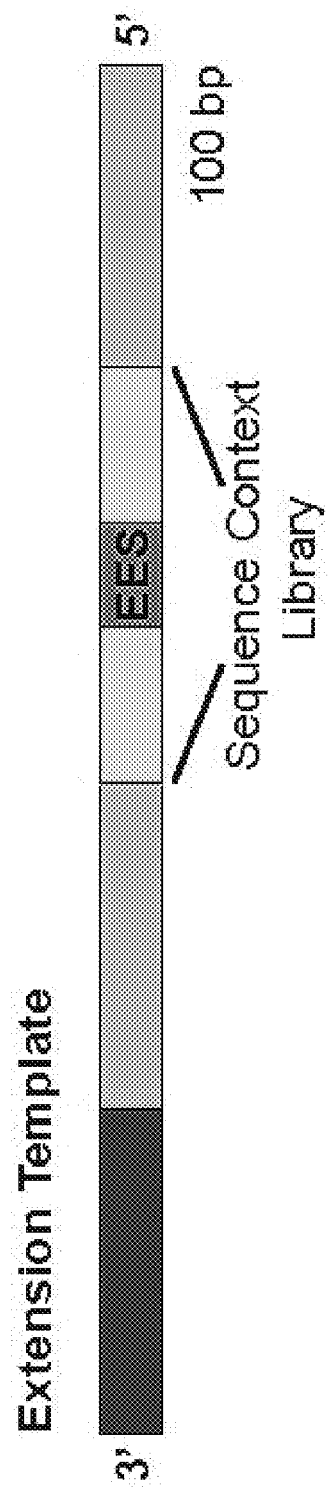

An error-rate amplification strategy for characterizing fidelity (FIG. 1A) uses a DNA polymerase extension assay with a specific template design and controlled levels of dNTPs. In some embodiments, the extension template consists of primarily three nucleotides (e.g., A, G, C) with a fourth base (e.g., T) reserved as the Error-Enriched Site (EES) positioned near the middle of the template (FIG. 1B). During primer extension, asymmetric levels of dNTPs are supplied, where three out of the four dNTPs (e.g., dTTP, dGTP, dCTP) are fixed at an equimolar concentration but the concentration of the dRTP, the complementary base to the template error site (e.g., dATP in FIG. 1A), is limited. The concentration of the dRTP is reduced until a concentration is found where a DNA polymerase is more likely to misincorporate one of the more abundant dNTPs or make a deletion at the EES than incorporate the dRTP correctly. For a given DNA polymerase, a critical concentration of dRTP exists ($FC_{50}$) for which a DNA polymerase will create replication errors as frequently as correct incorporations. This $FC_{50}$ metric correlates with a DNA polymerase's underlying error rate.

Figure 7:
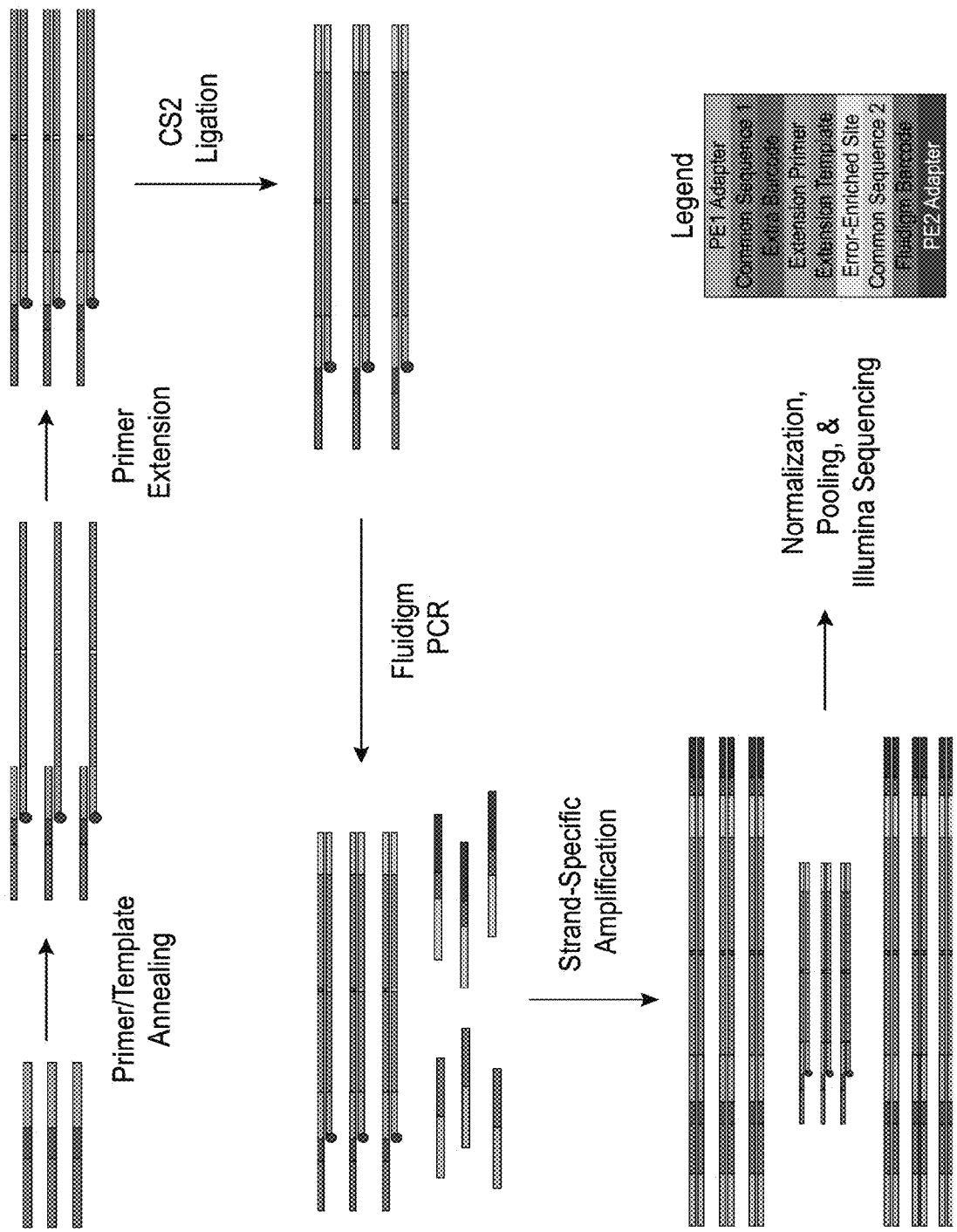
FIG. 7. Assay workflow. The exemplary nucleotide imbalance fidelity assay protocol comprises the following steps: 1) primer/template annealing, 2) primer extension under rare base conditions (red bar indicates a replication error created at the EES, dark purple circle signifies a 3' dideoxy-C modification), followed by column purification of synthesized products, 3) CS2 DNA ligation, 4) top strand-specific Fluidigm PCR of extended products, and 5) PCR product normalization and clean up followed by product pooling for paired-end sequencing.

The nucleotide imbalance fidelity assay procedure is displayed in FIG. 7. First, a universal extension primer is annealed to one of four possible templates. The DNA polymerase of interest is allowed to extend in several parallel reactions where the dRTP for a given template is diluted log-fold across those parallel reactions. After extension, several sample preparation steps are performed before deep sequencing to ensure that sequence-specific PCR amplification bias is suppressed and only the extended strand is sequenced (Ref 28; herein incorporated by reference in its entirety). This procedure allows us to robustly examine the behavior of DNA polymerases over a wide number of conditions in a high-throughput manner.

Scalability, Robustness and Sensitivity

Figure 2A:
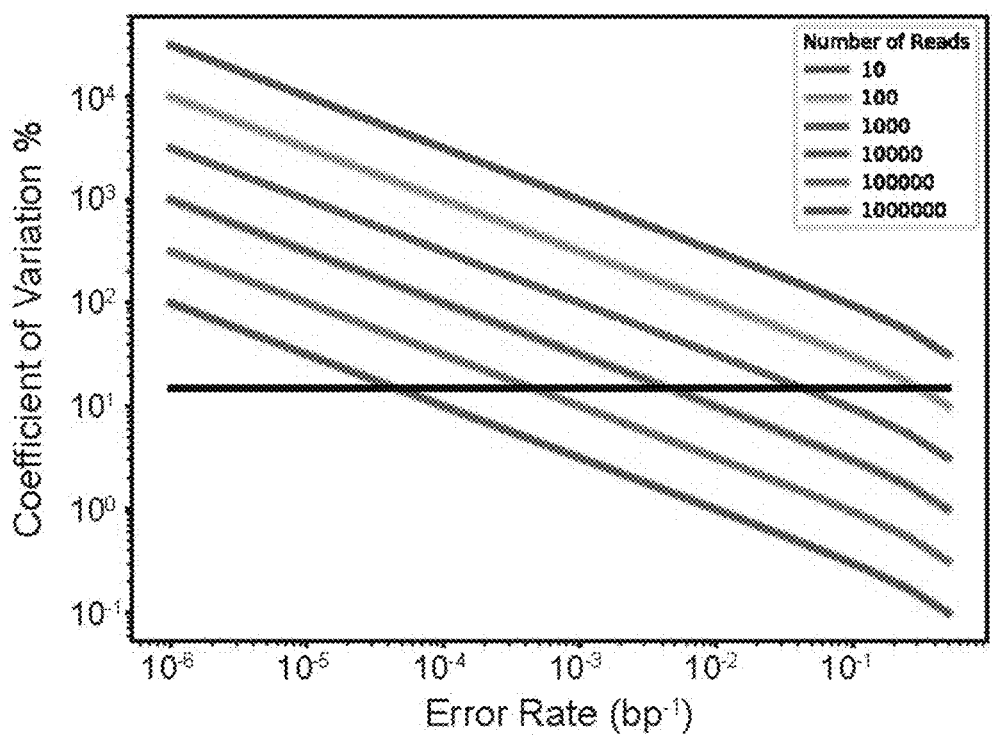
FIGS. 2A-2D: Assessing assay potential.

Experiments were conducted during development of embodiments herein to demonstrate the scalability of a nucleotide imbalance fidelity assay for high-throughput screening of different conditions, and how this scaling compared to other methods. In order to maintain satisfactory precision in apparent error rate measurements, a minimum number of NGS reads would be made. To determine this number, a DNA polymerase was simulated as a Bernoulli process at various error rates, and the variance of the measured error rate was determined based on the number of NGS reads observed (FIG. 2A). It was found that in order to capture error rates between 4%-30% with a coefficient of variation $$\frac{\sigma}{(\mu)} < 15\%,$$

only 1000 sequencing reads were required, and to capture error rates greater than 30%, only 100 reads were needed. Simulations demonstrated accurate determination of amplified error rates (e.g., moderate error rates induced by low dRTP concentration) with substantially fewer reads than those required for extremely low error rates under normal dNTP conditions. Given that the $FC_{50}$ (the previously defined fidelity metric) would correspond to error rate measurements near 50%, it was concluded that as few as 100 sequencing reads per rare base condition would enable reliable fitting of the $FC_{50}$ value. By establishing a correlation between nucleotide imbalanced error rates and true error rates, these findings indicated that nucleotide imbalanced error rates would allow analysis of DNA polymerase fidelity while using substantially reduced sequencing resources.

Figure 2B:
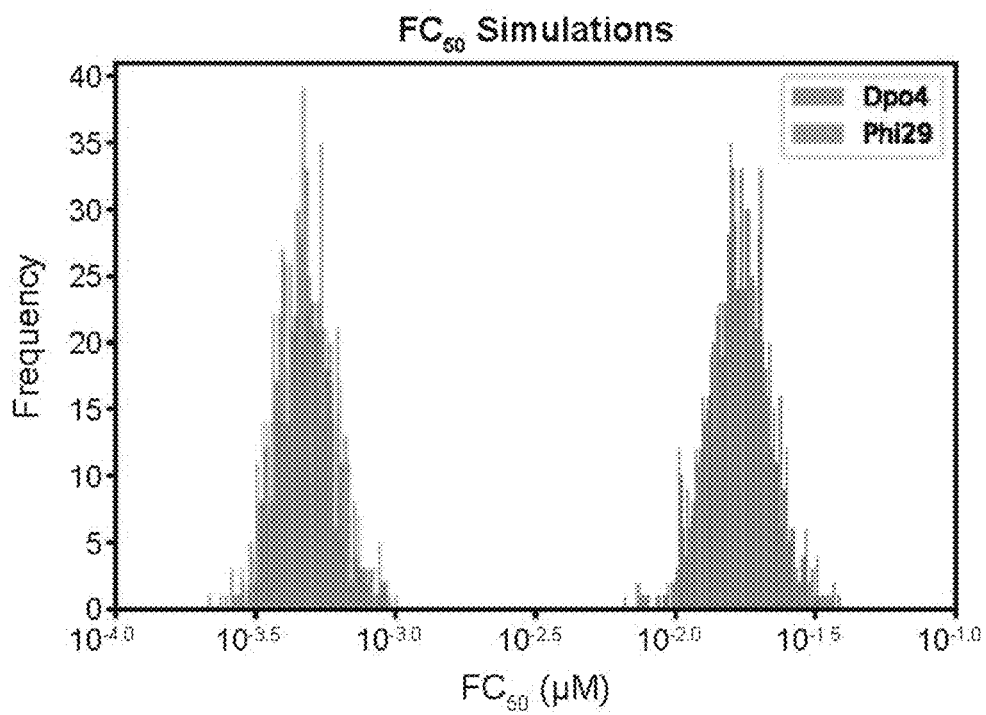

To determine how the apparent error rate uncertainty affects the proxy for actual DNAP error rates (the $FC_{50}$ metric), an initial assay trial was performed with a low fidelity polymerase, *S. islandicus* Dpo4 (Refs. 41-43; herein incorporated by reference in their entireties) and a high fidelity polymerase, Phi29 (Refs. 44-46; herein incorporated by reference in their entireties), copying in a "T" template context. Using these data, many parallel error rate readouts were simulated based on only 50 sequencing reads per rare base condition, providing a distribution of fitted $FC_{50}$ values for each DNA polymerase (FIG. 2B). The results demonstrate that the assay system is well calibrated, since random variance resulted in distributions around the measured $FC_{50}$ values that enabled clear separation of two different polymerases.

Figure 2C:
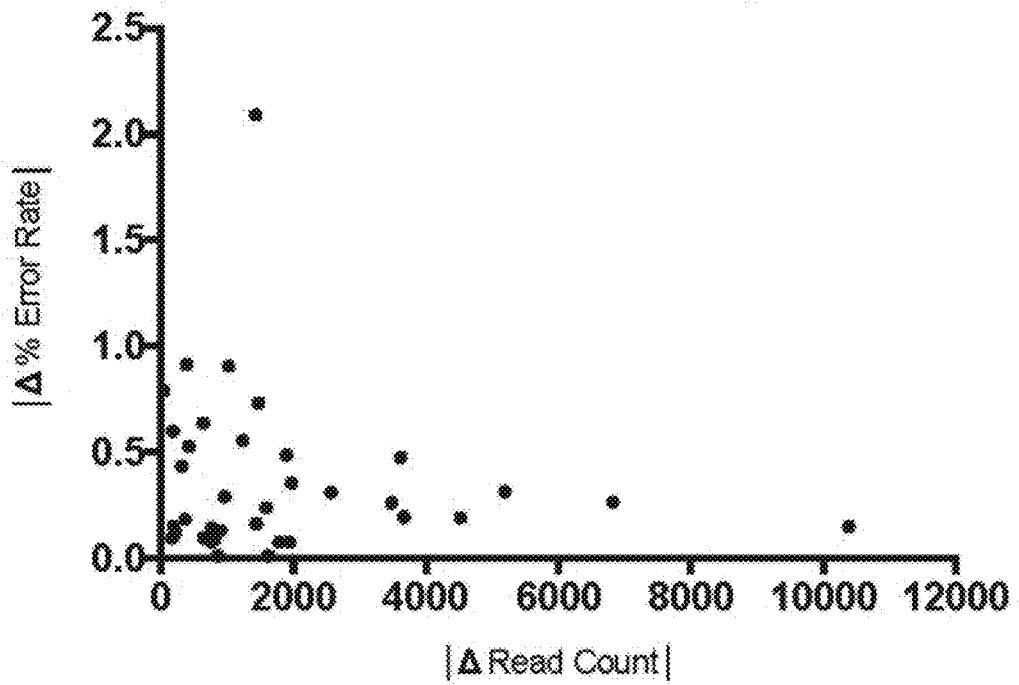
Figure 2D:
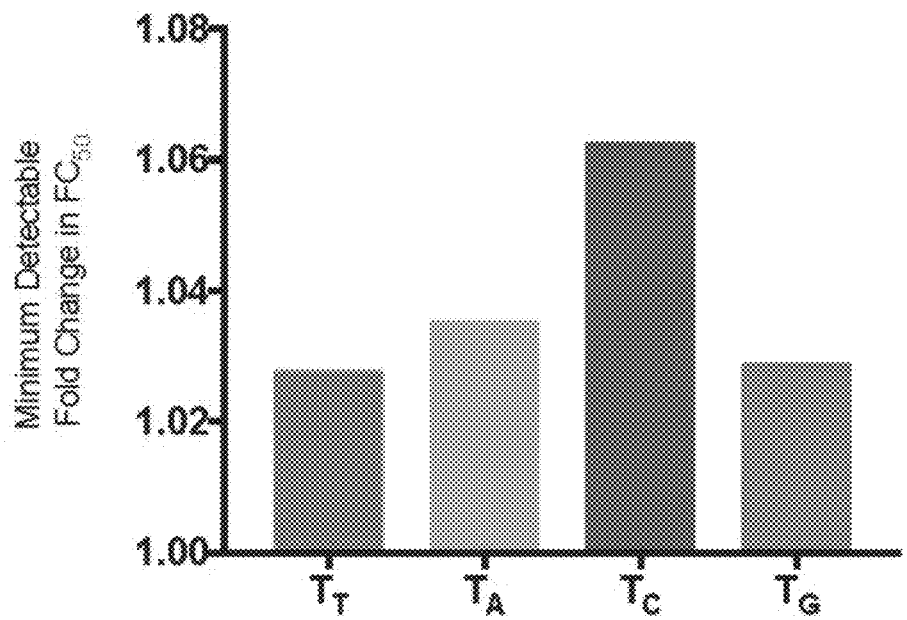

Experiments were conducted during development of embodiments herein to determine the robustness and sensitivity of the assays herein by performing additional nucleotide imbalance fidelity assays with Dpo4 copying in the remaining three rare base contexts. It was first determined whether variation in the number of sequencing reads between biological replicates had any significant impact on error rate readout. 36 sets of biological replicates (n=2) of Dpo4 copying 4 different template types were examined, and it was found that error rate values did not vary substantially with read counts (FIG. 2C). Experiments were conducted during development of embodiments herein to determine whether a nucleotide imbalance fidelity assay could resolve small differences in fidelity. From the Dpo4 data set, it was calculated that 10% changes in $FC_{50}$ (and even smaller) could be resolved with 95% confidence (FIG. 2D). The nucleotide imbalance fidelity assay demonstrated robust properties for large-scale characterization of polymerase fidelity. The assays herein required significantly fewer sequencing reads than other NGS-based methods, were robust against random variance, had low sample variability, and were a highly sensitive reporter of fidelity changes.

$FC_{50}$ Effectively Captures Native Error Rates of DNA Polymerases

Figure 3A:
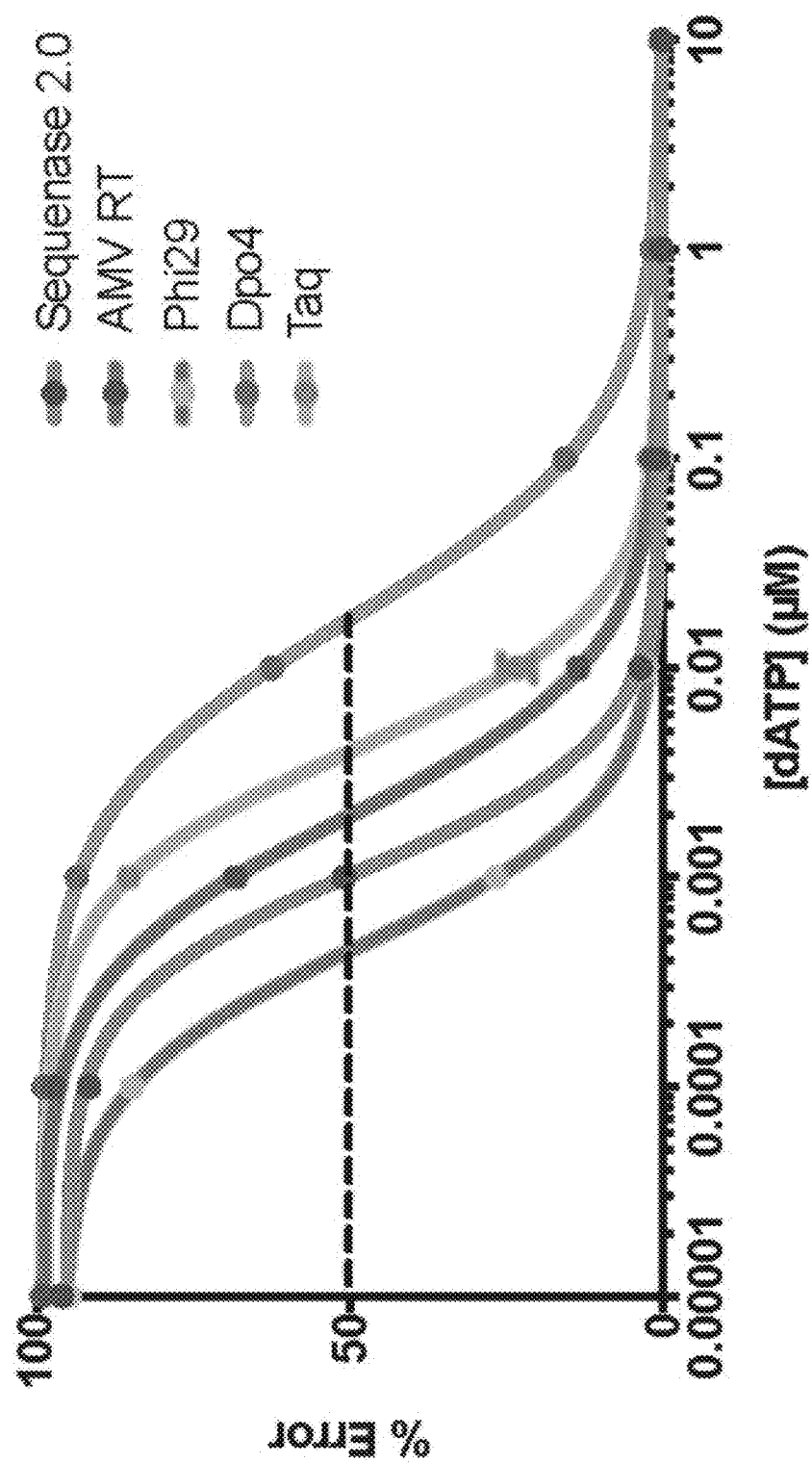
FIGS. 3A and 3B: Nucleotide imbalance fidelity assay validation.
Figure 3B:
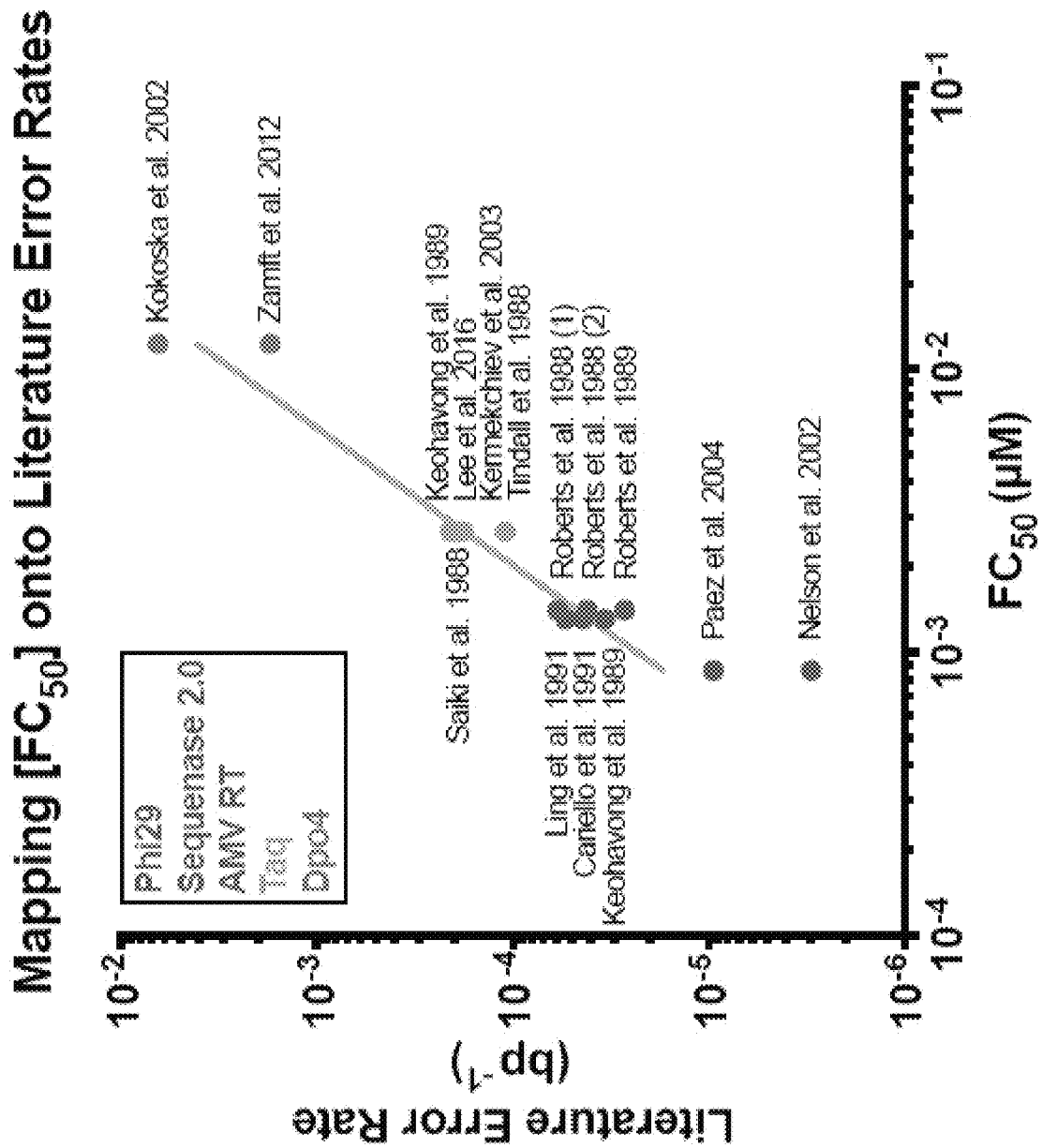

Experiments were conducted during development of embodiments herein to validate that that the assays herein recapitulate previously reported error rates for a range of DNA polymerases (FIG. 3A). Rare base extension assays were performed for five DNA polymerases: Dpo4, Phi29. Sequenase 2.0, Taq, and AMV RT. Dose response fidelity curves were compared of all five DNA polymerases copying in "T" template contexts (FIG. 3B). The lowest fidelity DNA polymerase tested, Dpo4, began making replication errors more than half the time between 0.01 and 0.1 uM dATP, while higher fidelity polymerases maintained lower error rates. Further log dilutions in [dATP] ultimately resulted in error saturation, indicating that an ideal range for resolving fidelity differences was between 0.0001-0.1 uM dATP. Rare base titration curves revealed $FC_{50}$ values of these DNA polymerases (Table 3) that agreed with documented error rates from previous studies (FIG. 3A, Table 4).

TABLE 3

FC50 values, 95% CIs of FC50 values, and R-squared values derived from rare base titration curve fitting of Sequenase 2.0, AMV RT, Phi29, Taq, and Dpo4 error rates (n = 2) in VVVTVVV, BBBABBB, DDDCDDD, and HHHGHHH template contexts. "All Four Contexts" signifies the fitting of duplicate error rate data from all four template contexts (n = 8) to produce an average FC50 representative of all four possible contexts.

| DNA Polymerase | Template Context | $FC_{50}$ (µM) | 95% CI Lower (µM) | 95% CI Upper (µM) | R-square |
|---|---|---|---|---|---|
| Sequenase 2.0 | VVVTVVV | 1.09E-03 | 1.04E-03 | 1.15E-03 | 0.9996 |
| | BBBABBB | 1.46E-03 | 1.23E-03 | 1.74E-03 | 0.9967 |
| | DDDCDDD | 1.09E-03 | 1.03E-03 | 1.16E-03 | 0.9995 |
| | HHHGHHH | 1.67E-03 | 1.62E-03 | 1.72E-03 | 0.9999 |
| | All Four Contexts | 1.31E-03 | 1.04E-03 | 1.64E-03 | 0.9655 |
| AMV RT | VVVTVVV | 1.98E-03 | 1.90E-03 | 2.06E-03 | 0.9999 |
| | BBBABBB | 6.70E-04 | 6.07E-04 | 7.39E-04 | 0.999 |
| | DDDCDDD | 1.02E-03 | 9.62E-04 | 1.09E-03 | 0.9993 |
| | HHHGHHH | 1.75E-03 | 1.61E-03 | 1.89E-03 | 0.9995 |
| | All Four Contexts | 1.41E-03 | 8.37E-04 | 2.36E-03 | 0.8487 |
| Phi29 | VVVTVVV | 4.75E-04 | 4.55E-04 | 4.97E-04 | 0.9998 |
| | BBBABBB | 8.77E-04 | 7.20E-04 | 1.07E-03 | 0.9948 |
| | DDDCDDD | 1.25E-03 | 1.13E-03 | 1.39E-03 | 0.9985 |
| | HHHGHHH | 1.39E-03 | 1.26E-03 | 1.64E-03 | 0.9989 |
| | All Four Contexts | 8.61E-04 | 4.51E-04 | 1.64E-03 | 0.7704 |
| Taq | VVVTVVV | 4.05E-03 | 3.83E-03 | 4.28E-03 | 0.9997 |
| | BBBABBB | 2.61E-03 | 2.47E-03 | 2.74E-03 | 0.9998 |
| | DDDCDDD | 2.15E-03 | 2.00E-03 | 2.30E-03 | 0.9998 |
| | HHHGHHH | 2.08E-03 | 1.98E-03 | 2.18E-03 | 0.9998 |
| | All Four Contexts | 2.67E-03 | 2.29E-03 | 3.12E-03 | 0.9886 |
| Dpo4 | VVVTVVV | 1.74E-02 | 1.70E-02 | 1.79E-02 | 0.9999 |
| | BBBABBB | 1.88E-02 | 1.82E-02 | 1.95E-02 | 0.9999 |
| | DDDCDDD | 1.24E-02 | 1.17E-02 | 1.32E-02 | 0.9997 |
| | HHHGHHH | 6.30E-03 | 6.13E-03 | 6.48E-03 | 0.9999 |
| | All Four Contexts | 1.23E-02 | 1.07E-02 | 1.42E-02 | 0.9899 |

TABLE 4

Previously reported error rates of Sequenase 2.0, AMV RT, Phi29, Taq, and Dpo4 from the literature.

| DNA Polymerase | Error Rate | Publication | Method |
|---|---|---|---|
| Sequenase 2.0 | 0.000034 errors/bp | Keohavong at al. 1989 (1) | Denaturing gradient gel electrophoresis |
| | 0.000044 errors/bp | Cariello et al. 1991 (2) | Denaturing gradient gel electrophoresis |
| | 0.000054 errors/bp | Ling et al. 1991 (3) | Denaturing gradient gel electrophoresis |
| AMV RT | 0.000027 subs/bp | Roberts et al. 1989 (4) | M13mp2 forward mutation assay |
| | 0.000042 subs/bp | Roberts et al. 1988 (5) | M13mp2 codon reversion assay |
| | 0.000059 errors/bp | Roberts et al. 1988 (5) | M13mp2 forward mutation assay |
| Phi29 | 0.0000095 errors/bp | Paez et al. 2004 (6) | Direct sequencing |
| | 0.000003 errors/bp | Nelson et al. 2002 (7) | Modified Kunkel method |

TABLE 4-continued

Previously reported error rates of Sequenase 2.0, AMV RT, Phi29, Taq, and Dpo4 from the literature.

| DNA Polymerase | Error Rate | Publication | Method |
| --- | --- | --- | --- |
| Taq | 0.0002 subs/bp | Saiki et al. 1988 (8) | Colony sequencing |
| | 0.00011 subs/bp | Tindall et al. 1988 (9) | M13mp2 forward mutation assay |
| | 0.00021 errors/bp | Keohavong et al. 1989 (1) | Denaturing gradient gel electrophoresis |
| | 0.00018 errors/bp | Kermekchiev et al. 2003 (10) | lacZ PCR assay |
| Dpo4 | 0.0065 subs/bp | Kokosa et al. 2002 (11) | M13mp2 forward mutation assay |
| | 0.00174 subs/bp | Zamft et al. 2012 (12) | Next-generation sequencing |

To validate how well the assays represent DNA polymerase error rates, dose response data from all four rare base contexts were fit to obtain an average $FC_{50}$ for each DNA polymerase studied (Table 3). Nonlinear calibration between average $FC_{50}$ values and previously reported literature error rates to determine how well the $FC_{50}$ metric would map onto traditional measures of fidelity (FIG. 3B). Each average [$FC_{50}$] was converted to a predicted error rate using Equation 9 derived in Methods. Nonlinear fitting showed good agreement with the spread of literature values reported for each DNA polymerase. Predicted error rates were compared to previously reported literature error rates of all five DNA polymerases (FIG. 3C). The $FC_{50}$-derived error rates showed good linear agreement ($R^2$=0.916) with the relative literature error rate values reported for Sequenase 2.0, AMV RT, Phi29, Taq and Dpo4. For Phi29, the estimated error rate fell 2.7-fold from the mean of the two reported literature error rates.

Figure 8:
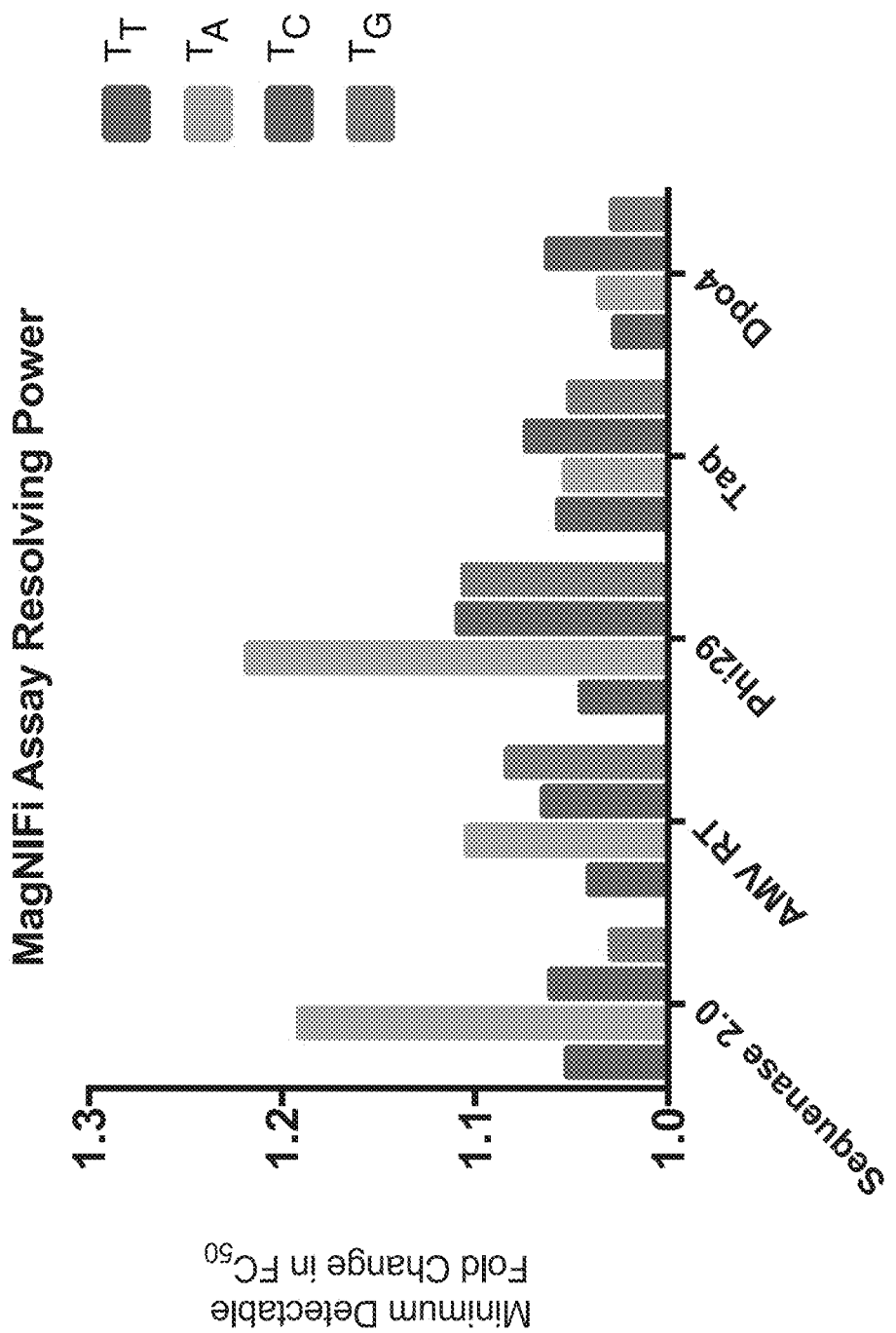
FIG. 8. Resolving power of a nucleotide imbalance fidelity assay based on $FC_{50}$ sensitivity. Minimum detectable fold change in $FC_{50}$ was determined based on the 95% confidence interval of the fitted $FC_{50}$ (see Table 3 for values). The ratio of the Upper Bound 95% CI: Fitted $FC_{50}$ was determined for Sequenase 2.0, AMV RT, Phi29, Taq, and Dpo4 copying in "T", "A", "C", and "G" template contexts.
Figure 9:
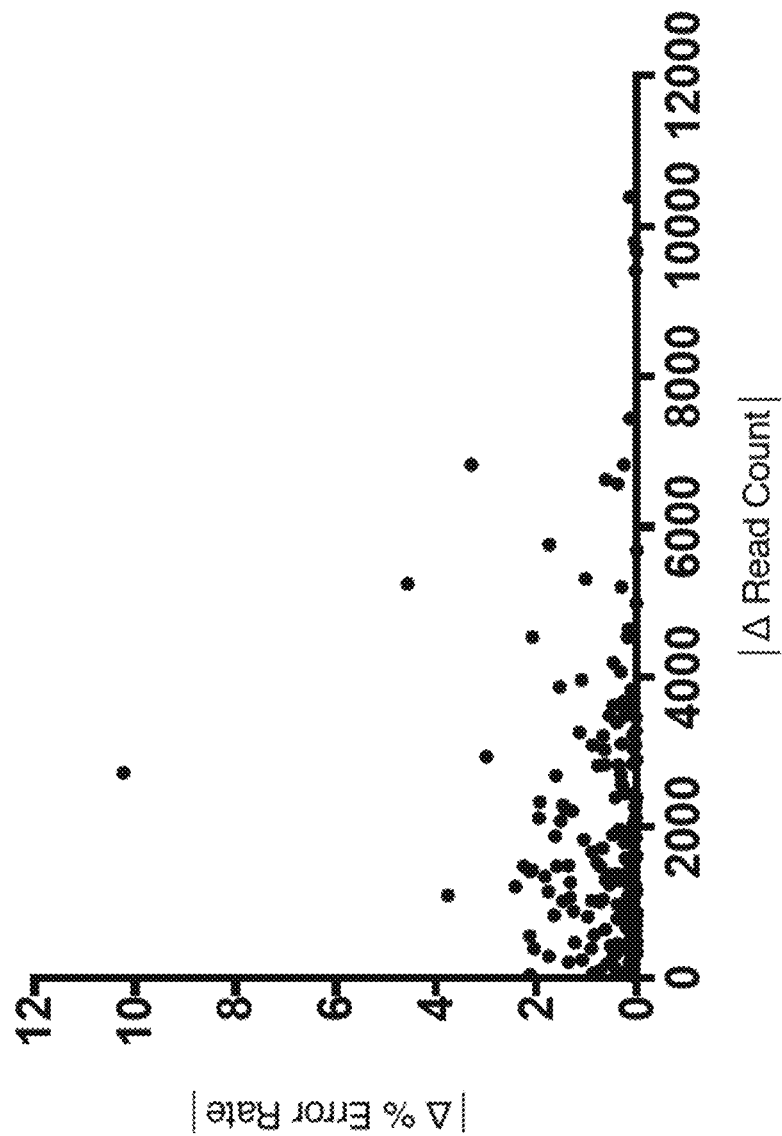
FIG. 9. Determination of assay sample variability across different read counts. Error rate data collected for Sequenase 2.0, AMV RT, Phi29, Taq, and Dpo4 copying in all four template contexts reveal that error rate differences between 180 sets of biological replicates (n=2) do not vary with read count differences between the same set of biological replicates.
Figure 10A:
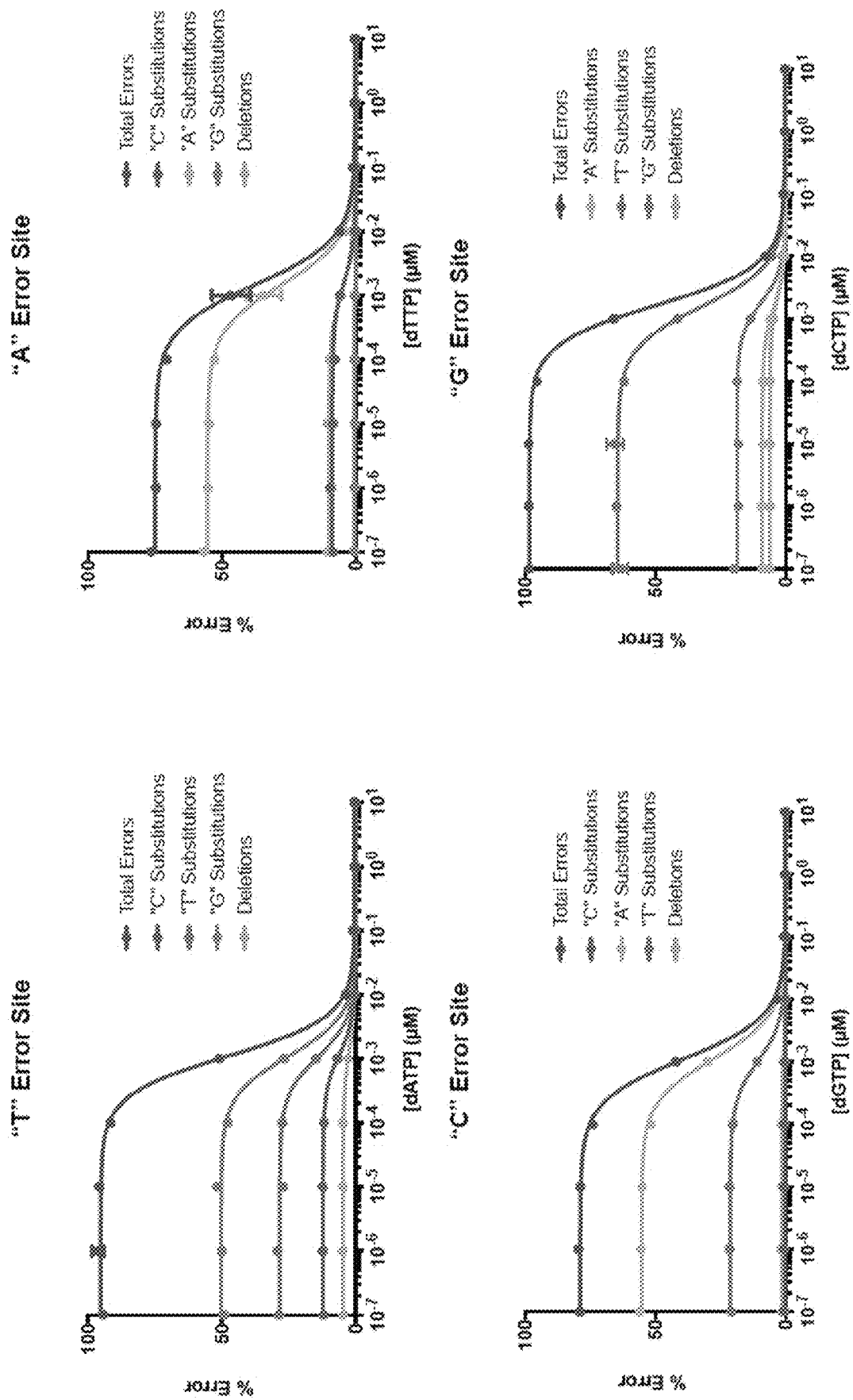
FIGS. 10A-10D: High-resolution fidelity profiles. Rare base titration curves are shown for Sequenase 2.0 in FIG. 10A, AMV RT in FIG. 10B, Phi29 in FIG. 10C, and Taq polymerase in FIG. 10D, copying in all four template contexts. Preferred error type (nucleotide substitutions and deletions) is quantified for each DNA polymerase synthesizing in each template context. Total error represents the sum of all error types. Values are the average of two experiments. Standard deviation error bars (n=2) are smaller than data points. We note that for certain rare base contexts, some DNA polymerases correctly incorporate even at very low concentrations of dRTP ($10^{-7}$ µM), suggesting high substrate sensitivity and selectivity for correct Watson-Crick base pairing. Furthermore, contaminating trace levels of dRTP in non-rare base stocks from commercial dNTP manufacturing could impact the true concentration of dRTP propagated in each dilution series. Since the same dNTP stocks were used for each reaction, potential contaminating effects were systematic and did not impact the $FC_{50}$ estimate.
Figure 10B:
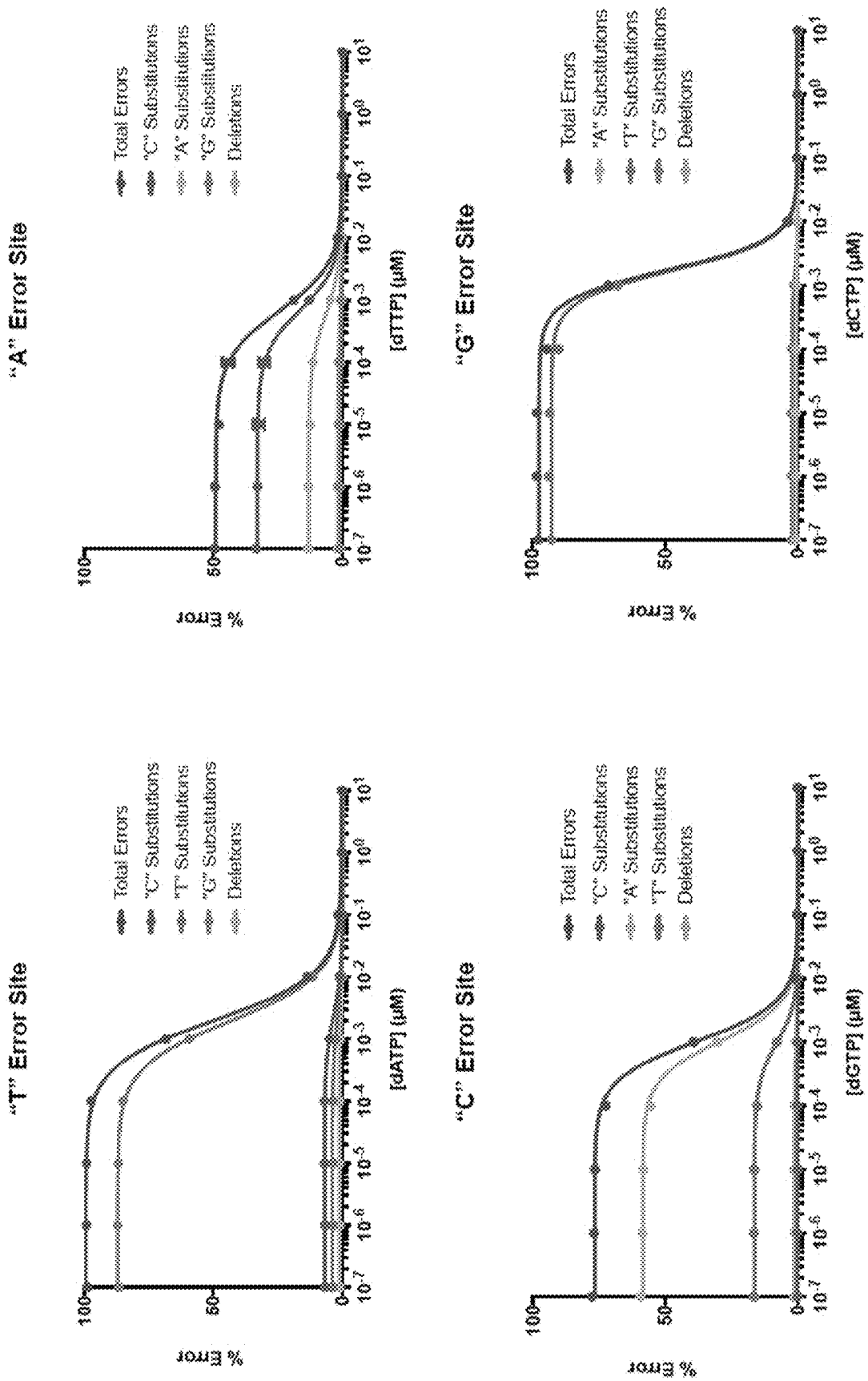
Figure 10C:
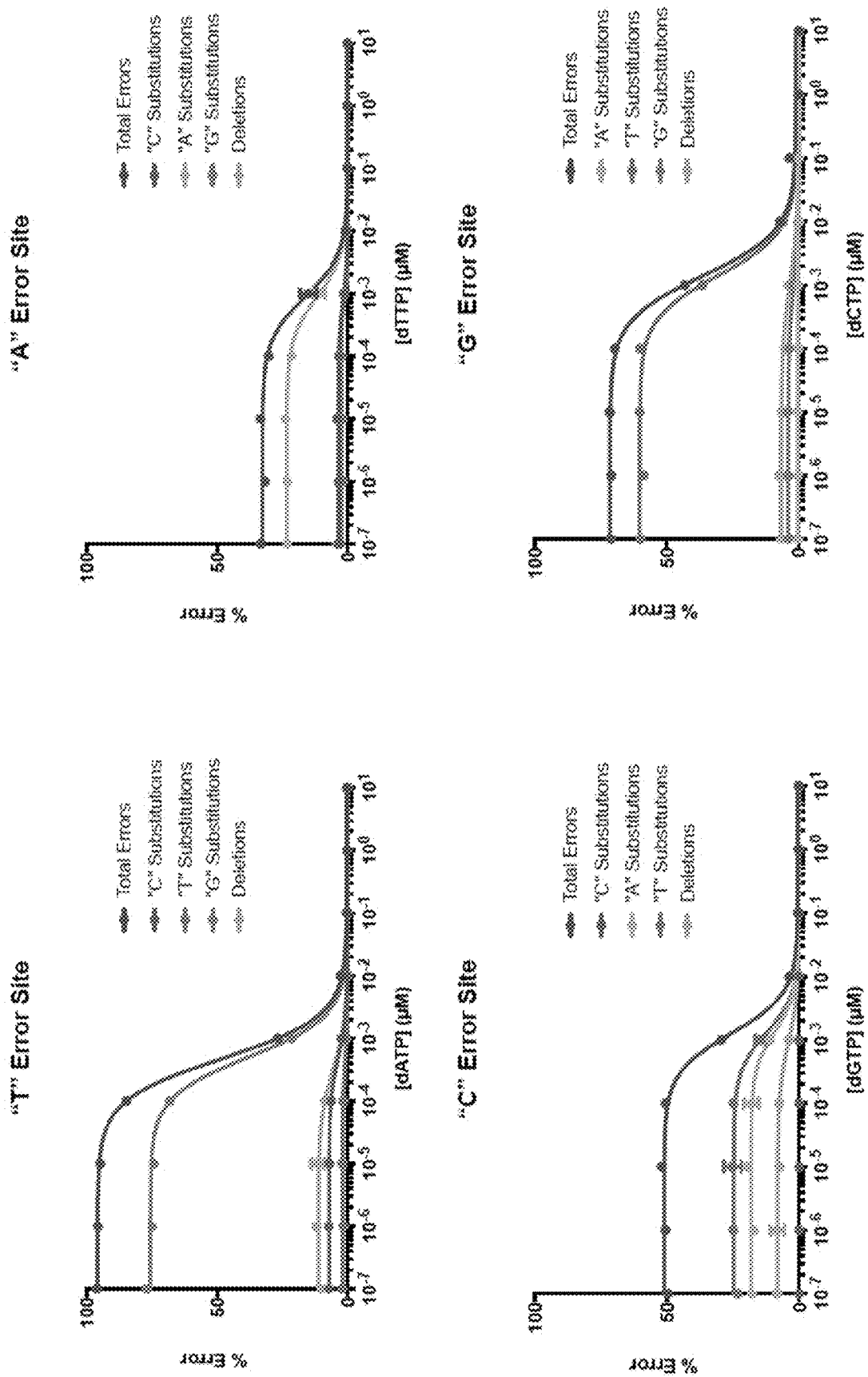
Figure 10D:
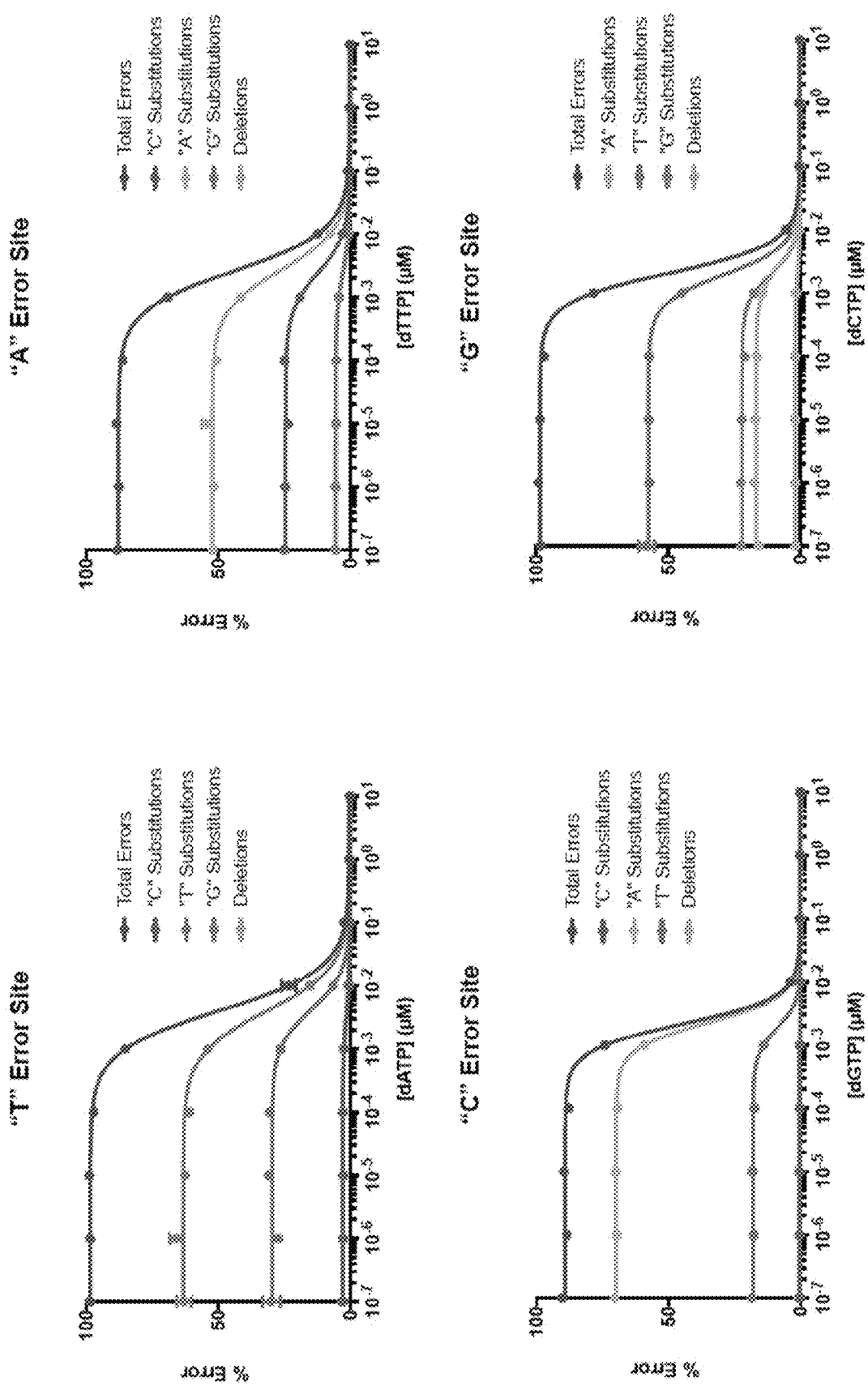
Figure 11A:
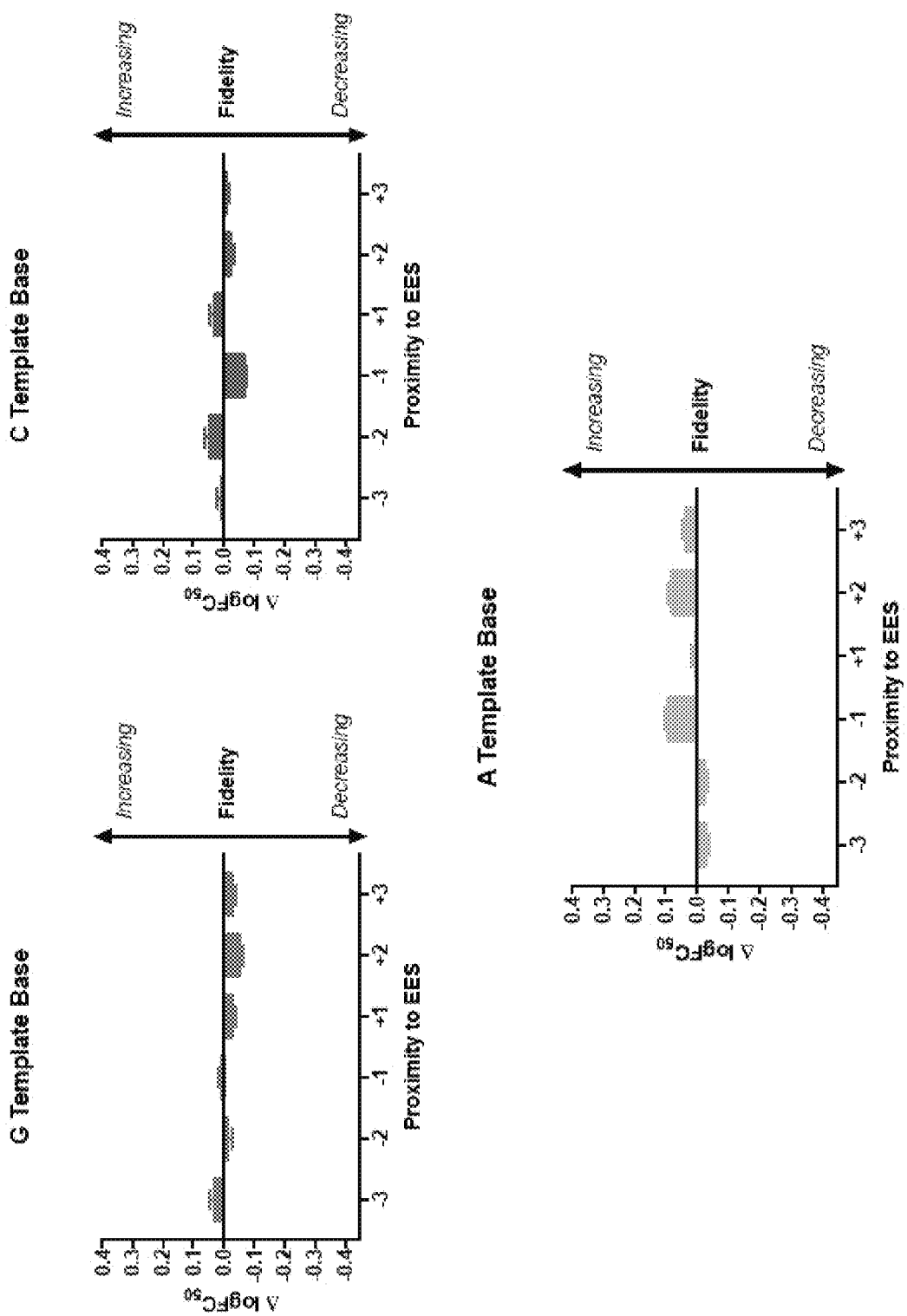
FIGS. 11A-11D: Effect of sequence context on $FC_{50}$ of Sequenase 2.0. The identity and position of template bases neighboring "T", "A", "C" and "G" EESs impact the measured $FC_{50}$ of Sequenase 2.0 copying in VVVTVVV (as shown in FIG. 11A), BBBABBB (as shown in FIG. 11B), DDDCDDD (as shown in FIG. 11C), and HHHGHHH (as shown in FIG. 11D) template contexts, respectively. Change in log $FC_{50}$ (log $FC_{50}$_Average–log $FC_{50}$_Fixed Template Base) was calculated for each base identity/position. Positive Δ log $FC_{50}$ values pertain to an increase in fidelity whereas negative values signify a decrease in fidelity. Values represent the average of two experiments. Error bars signify standard deviation (n=2).
Figure 11B:
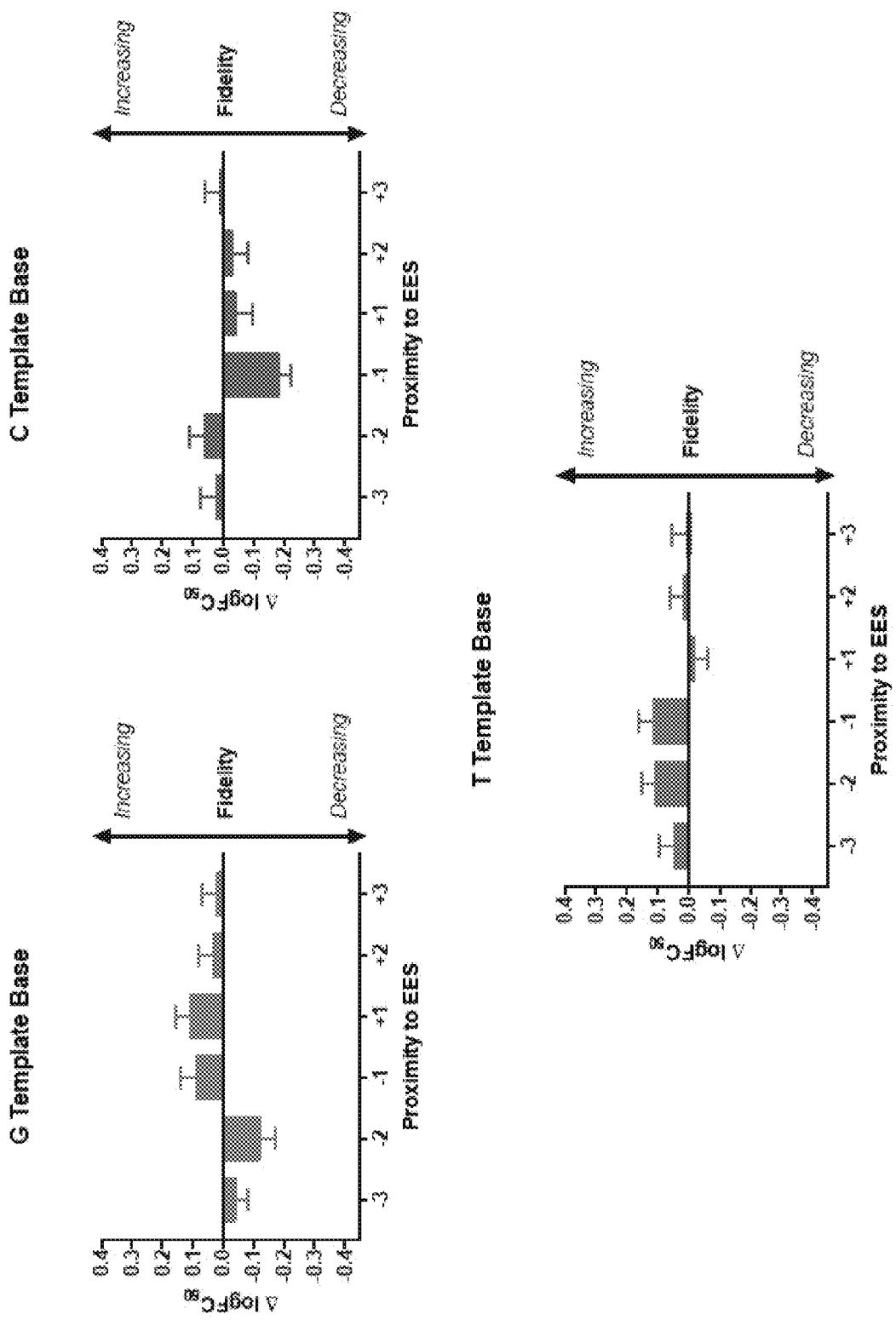
Figure 11C:
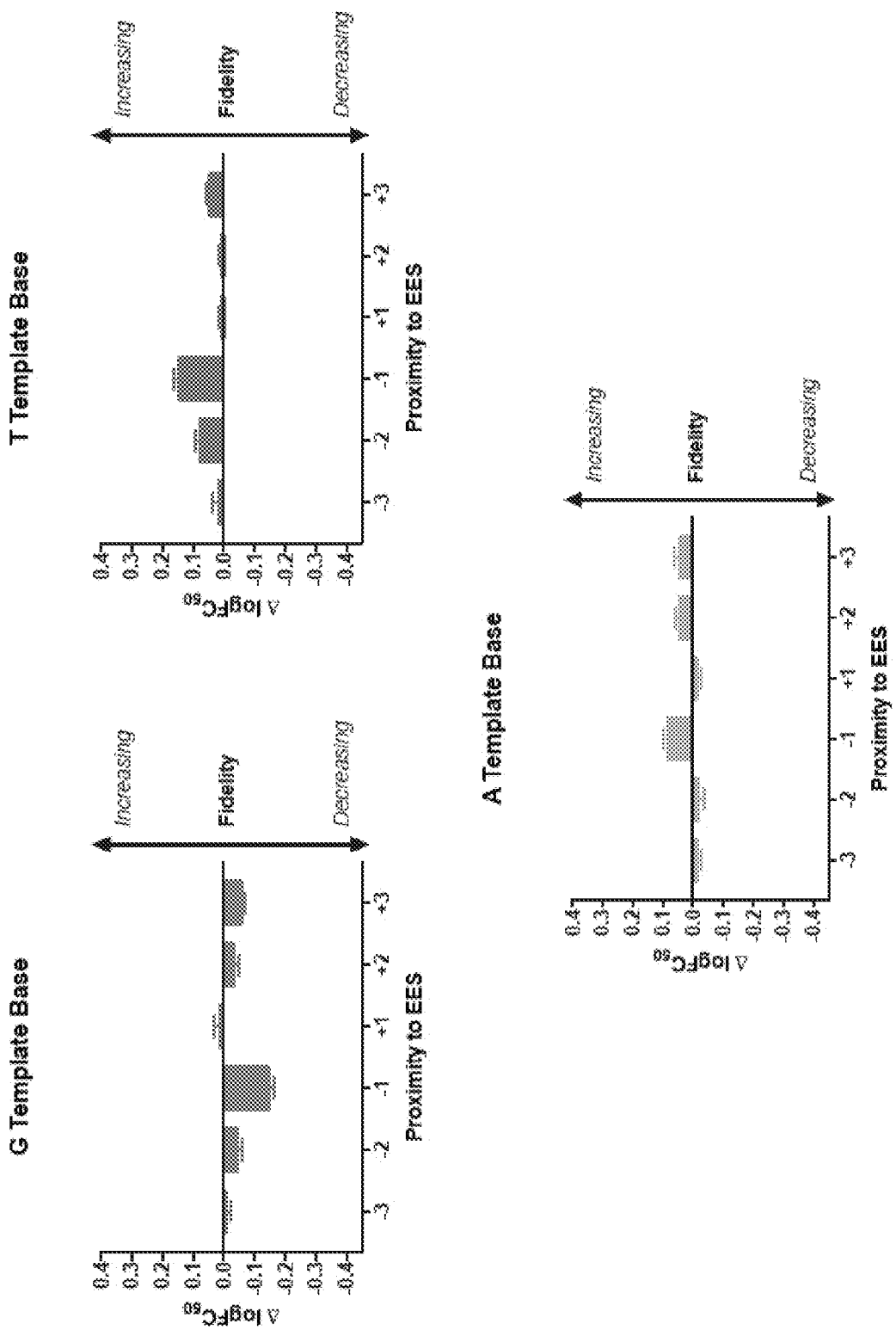
Figure 11D:
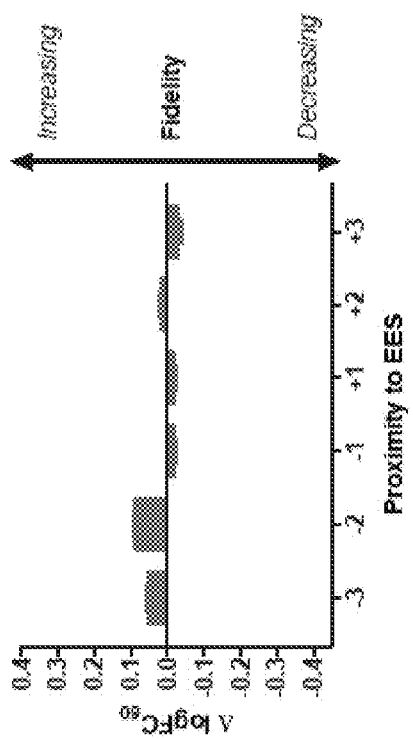
Figure 11D:
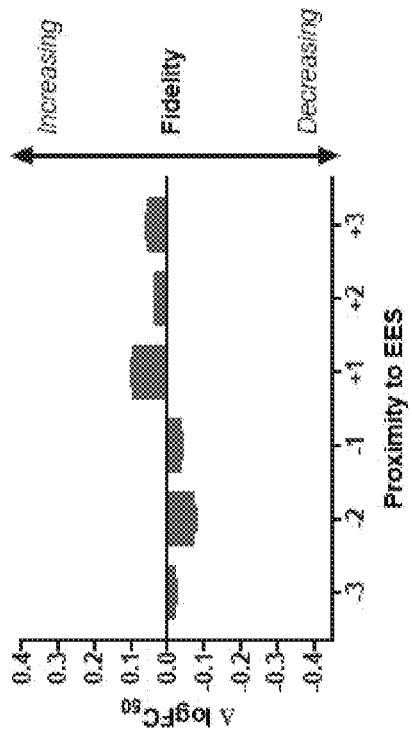
Figure 11D:
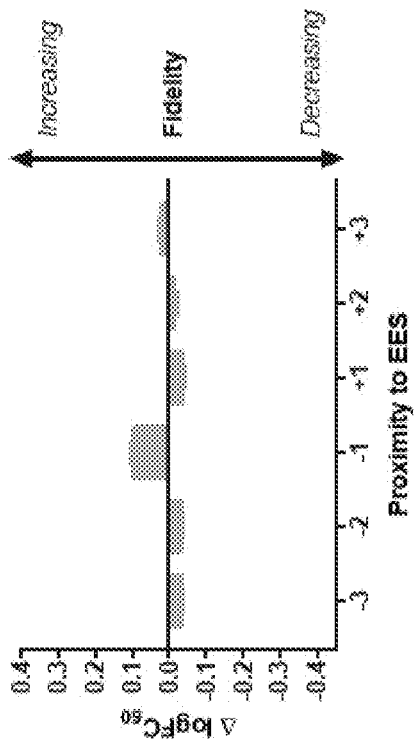
Figure 12A:
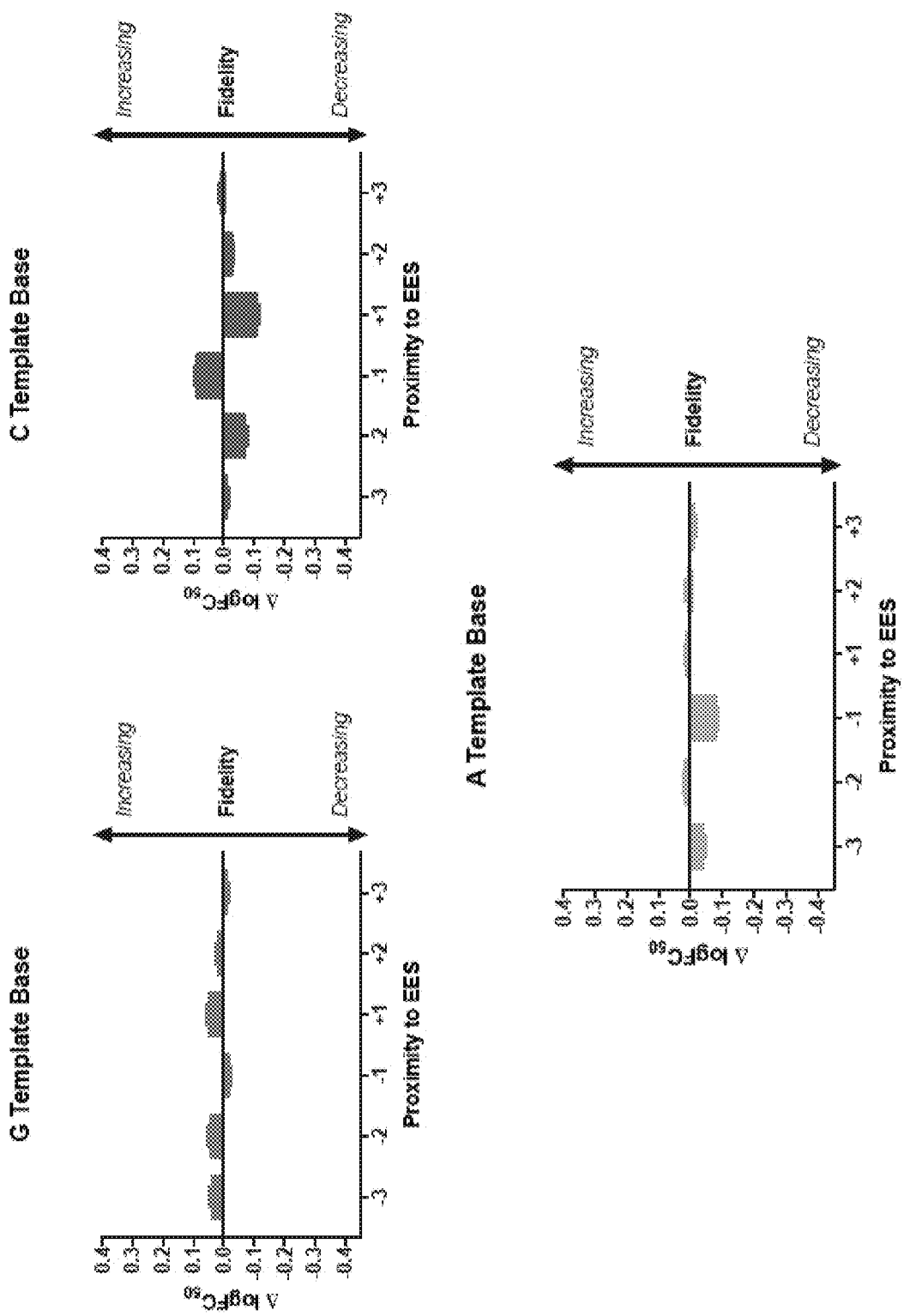
FIGS. 12A-12D: Effect of sequence context on $FC_{50}$ of AMV RT. The identity and position of template bases neighboring "T", "A", "C" and "G" EESs impact the measured $FC_{50}$ of AMV RT copying in VVVTVVV (as shown in FIG. 12A), BBBABBB, (as shown in FIG. 12B) DDDCDDD (as shown in FIG. 12C), and HHHGHHH (as shown in FIG. 12D) template contexts, respectively. Change in log $FC_{50}$ (log $FC_{50}$_Average–log $FC_{50}$_Fixed Template Base) was calculated for each base identity/position. Positive Δ log $FC_{50}$ values pertain to an increase in fidelity whereas negative values signify a decrease in fidelity. Values represent the average of two experiments. Error bars signify standard deviation (n=2).
Figure 12B:
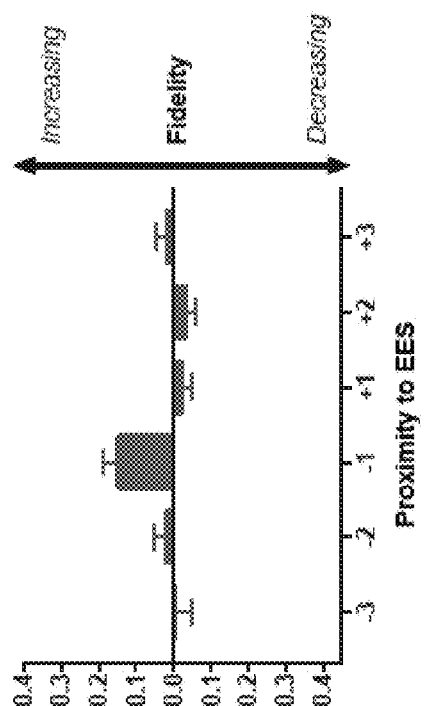
Figure 12B:
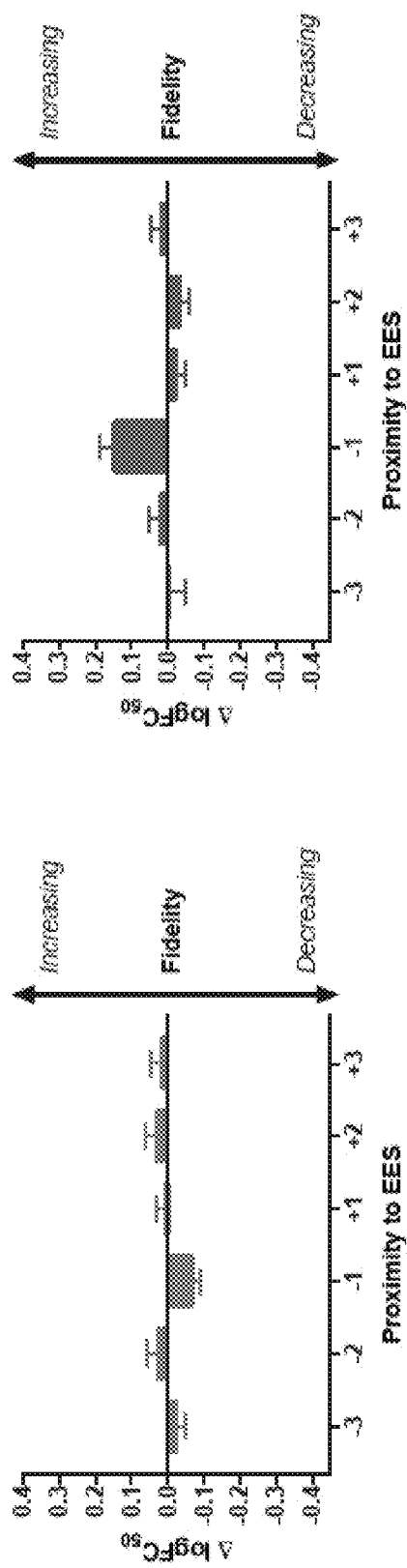
Figure 12B:
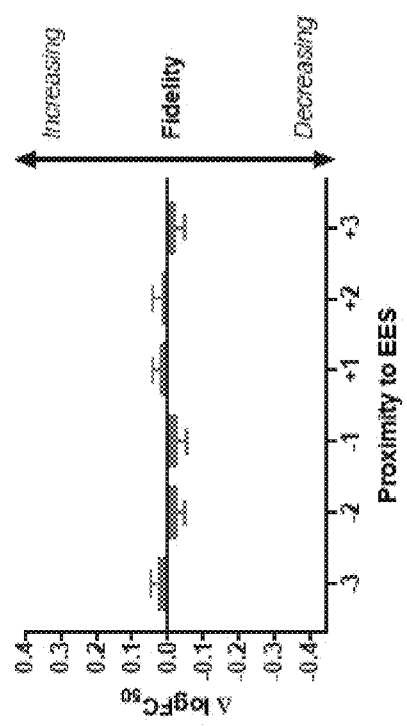
Figure 12C:
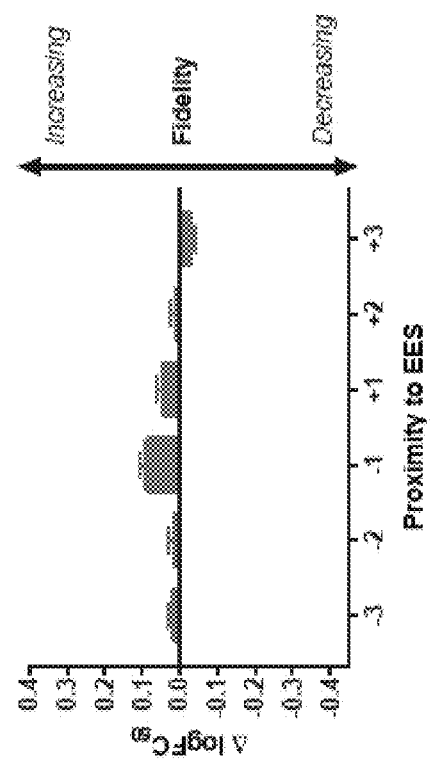
Figure 12C:
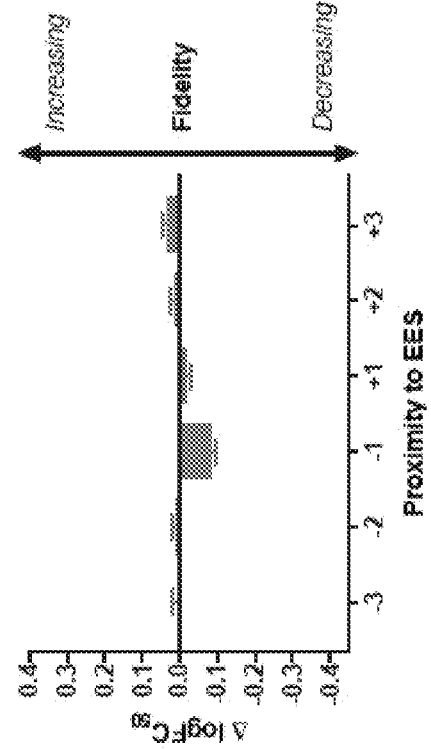
Figure 12C:
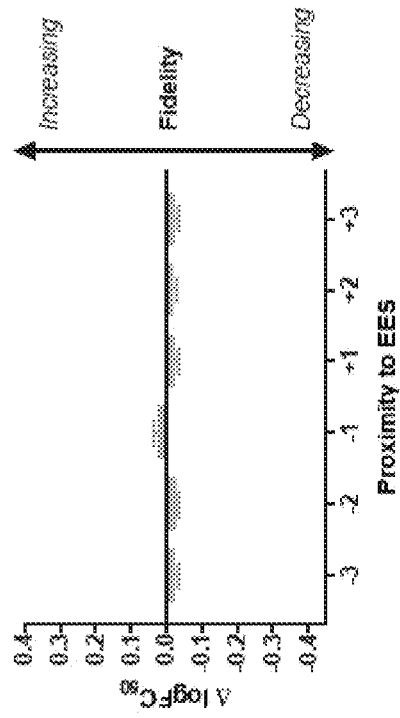
Figure 12D:
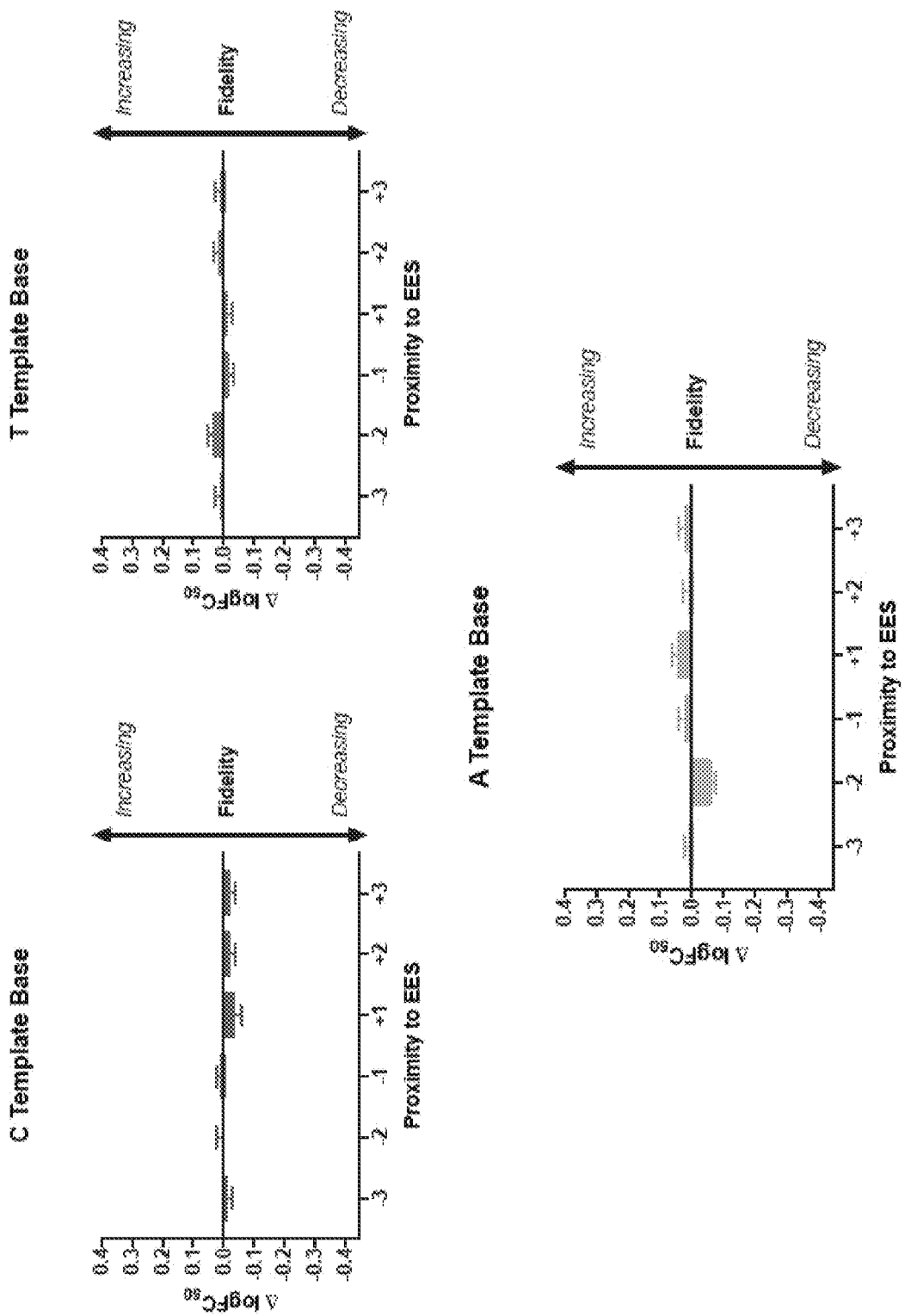
Figure 13A:
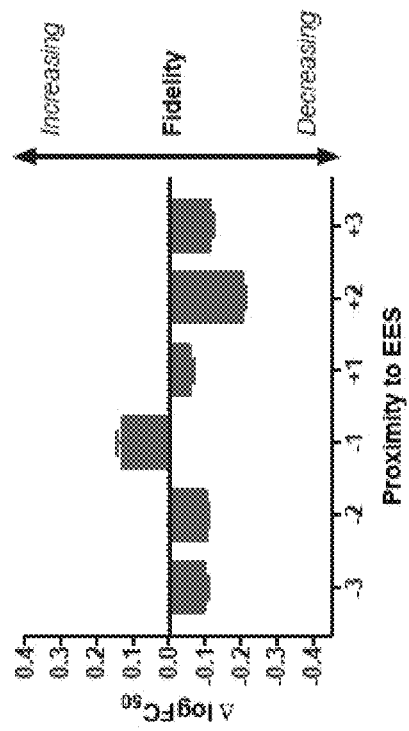
FIGS. 13A-13D: Effect of sequence context on $FC_{50}$ of Phi29. The identity and position of template bases neighboring "T", "A", "C" and "G" EESs impact the measured $FC_{50}$ of Phi29 copying in VVVTVVV (as shown in FIG. 13A), BBBABBB (as shown in FIG. 13B), DDDCDDD (as shown in FIG. 13C), and HHHGHHH (as shown in FIG. 13D) template contexts, respectively. Change in log $FC_{50}$ (log $FC_{50}$_Average–log $FC_{50}$_Fixed Template Base) was calculated for each base identity/position. Positive Δ log $FC_{50}$ values pertain to an increase in fidelity whereas negative values signify a decrease in fidelity. Values represent the average of two experiments. Error bars signify standard deviation (n=2).
Figure 13A:
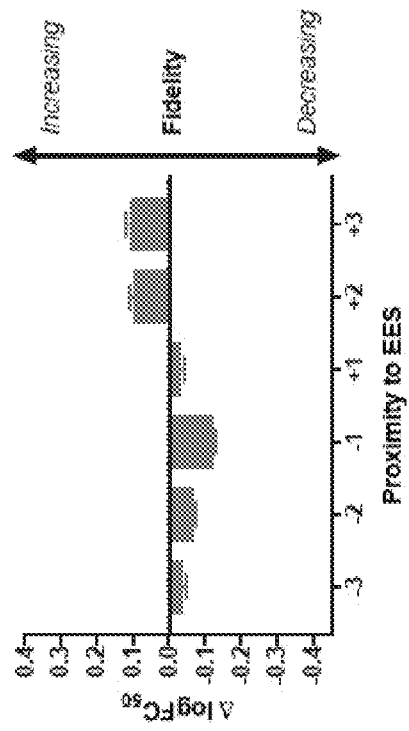
Figure 13A:
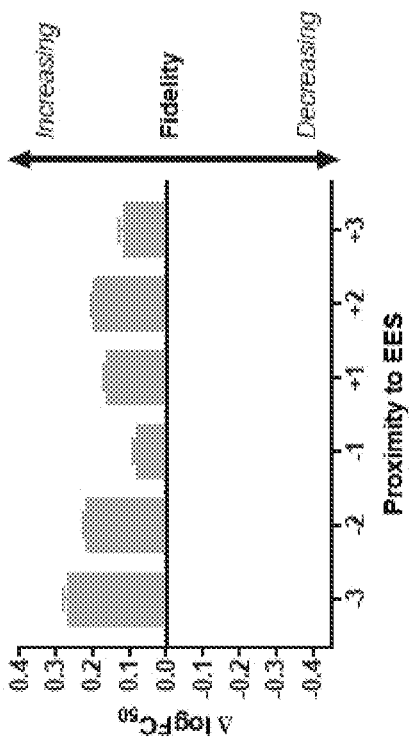
Figure 13B:
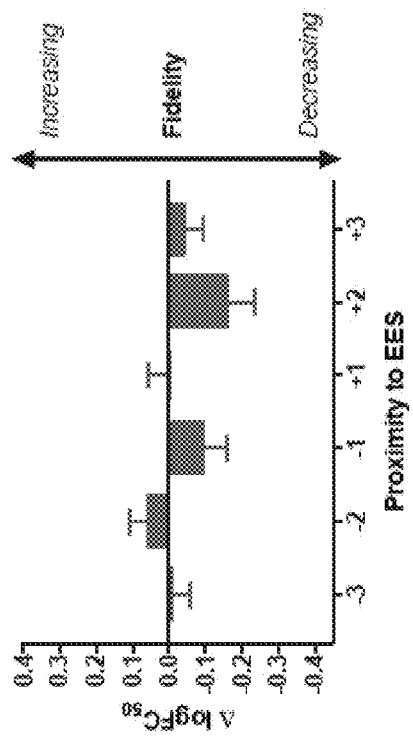
Figure 13B:
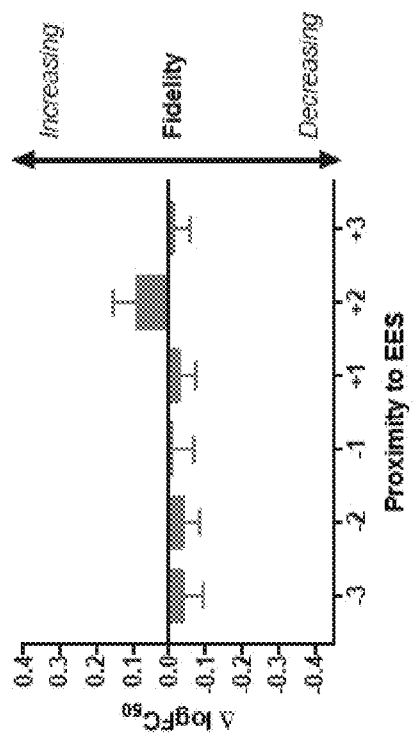
Figure 13B:
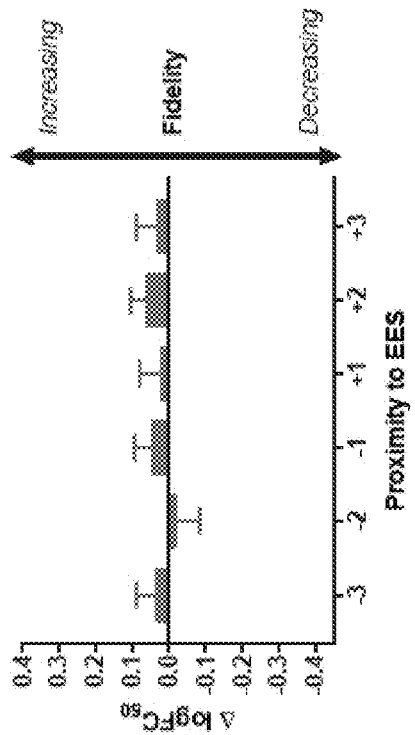
Figure 13C:
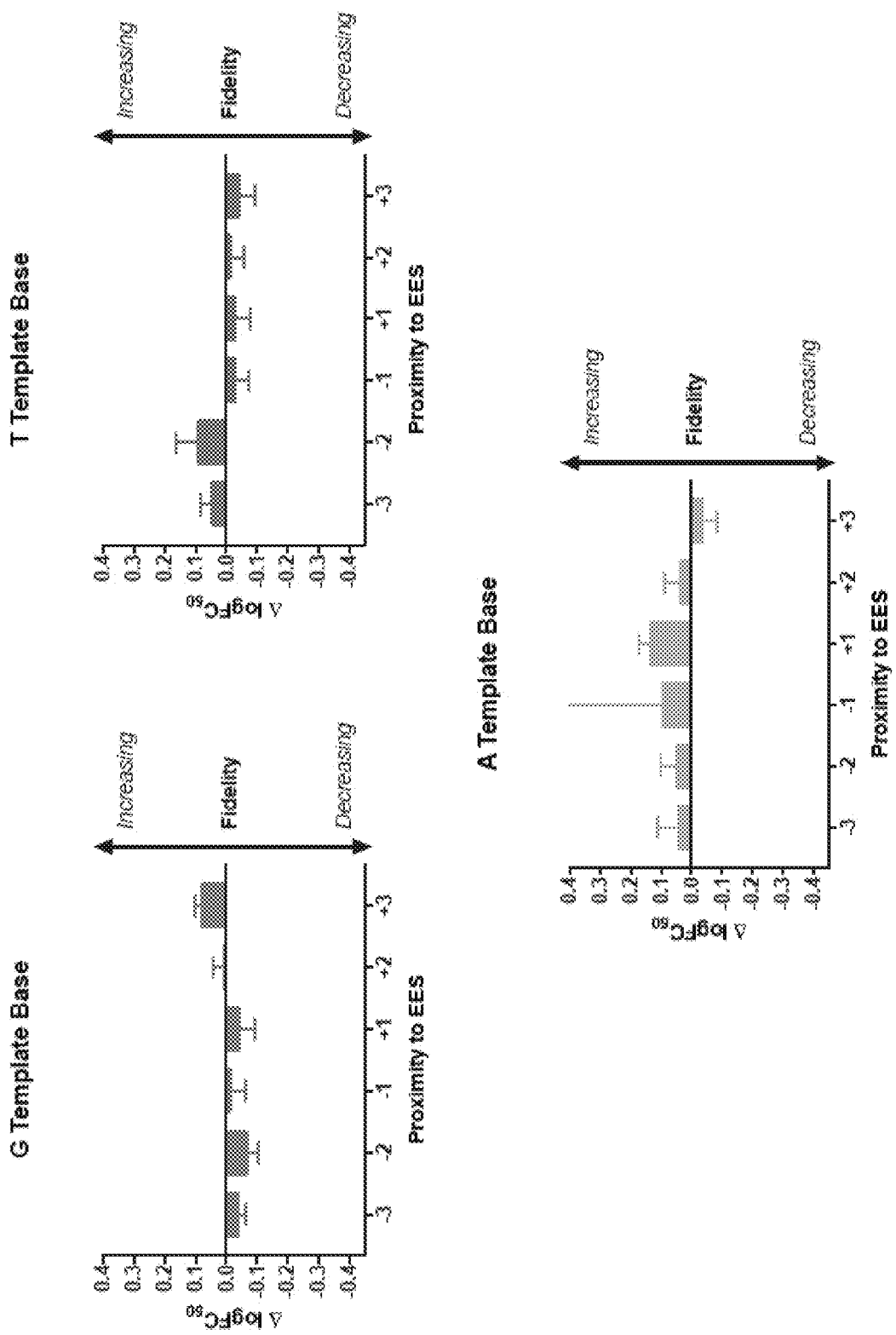
Figure 13D:
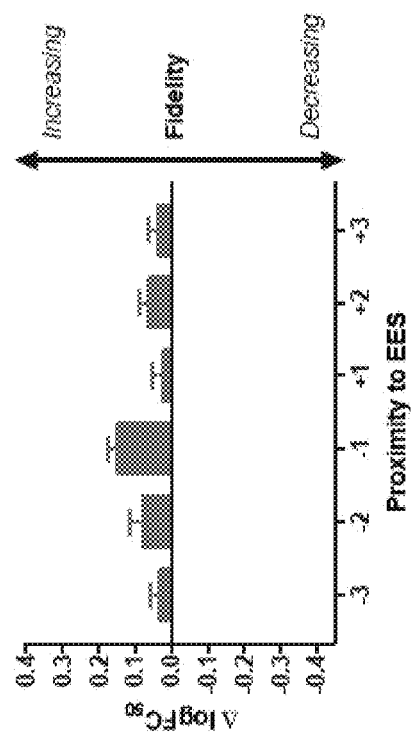
Figure 13D:
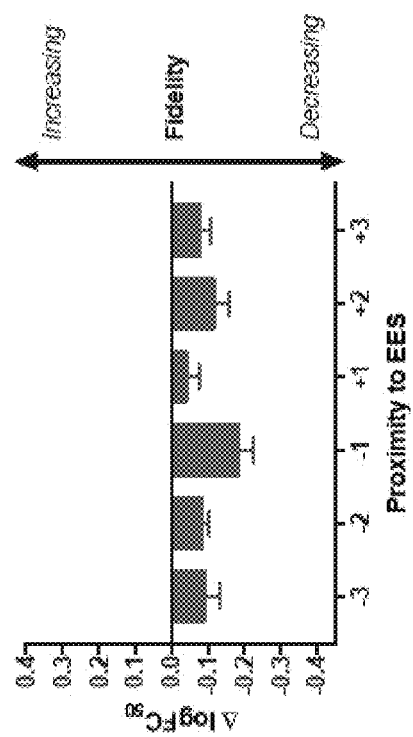
Figure 13D:
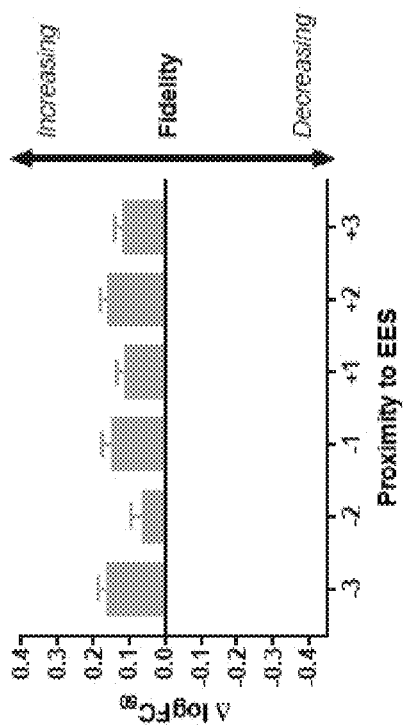
Figure 14A:
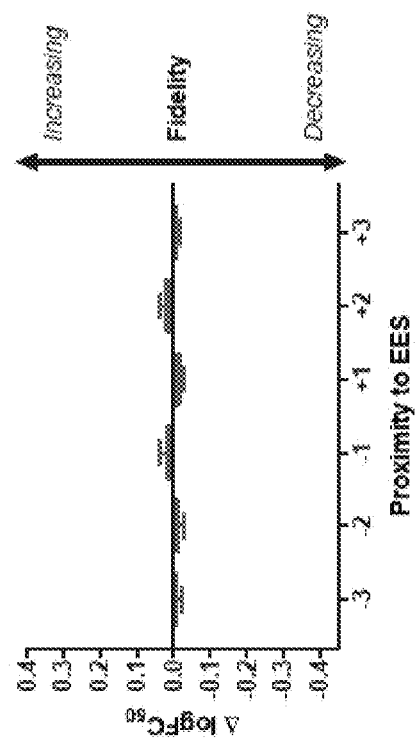
FIGS. 14A-14D: Effect of sequence context on $FC_{50}$ of Taq. The identity and position of template bases neighboring "T", "A", "C" and "G" EESs impact the measured $FC_{50}$ of Taq copying in VVVTVVV (as shown in FIG. 14A), BBBABBB, (as shown in FIG. 14B) DDDCDDD (as shown in FIG. 14C), and HHHGHHH (as shown in FIG. 14D) template contexts, respectively. Change in log $FC_{50}$ (log $FC_{50}$_Average–log $FC_{50}$_Fixed Template Base) was calculated for each base identity/position. Positive Δ log $FC_{50}$ values pertain to an increase in fidelity whereas negative values signify a decrease in fidelity. Values represent the average of two experiments. Error bars signify standard deviation (n=2).
Figure 14A:
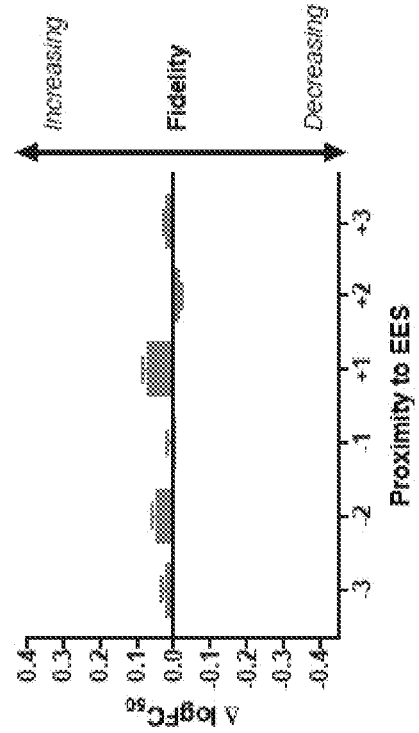
Figure 14A:
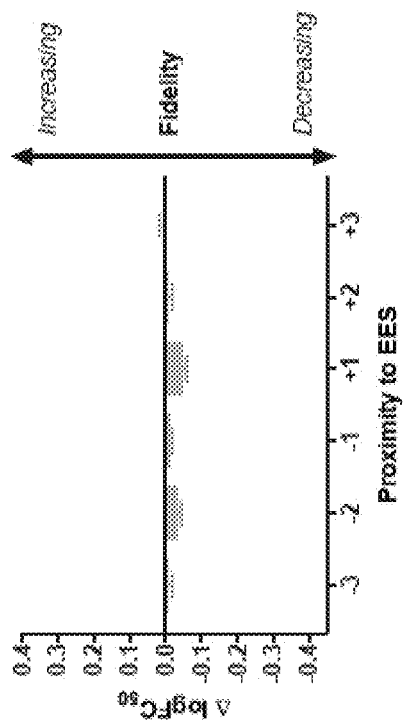
Figure 14B:
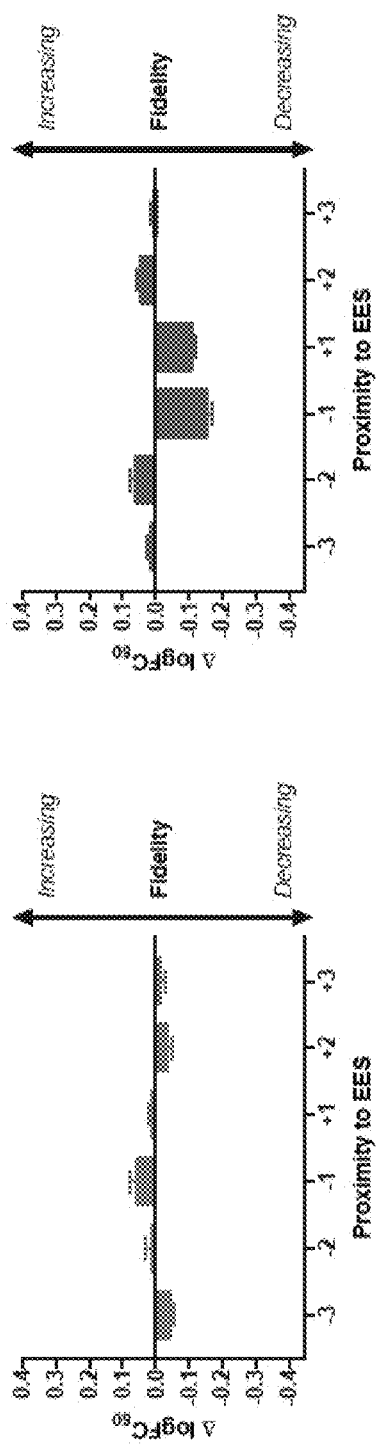
Figure 14B:
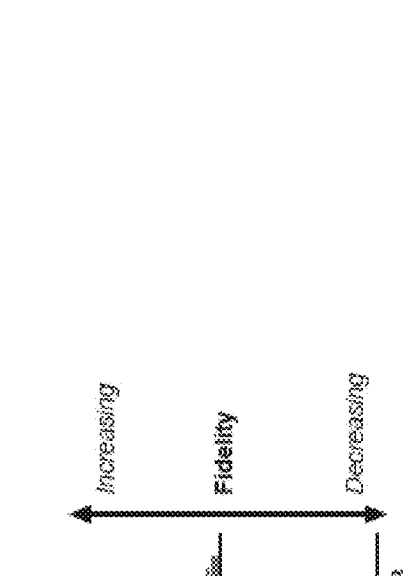
Figure 14B:
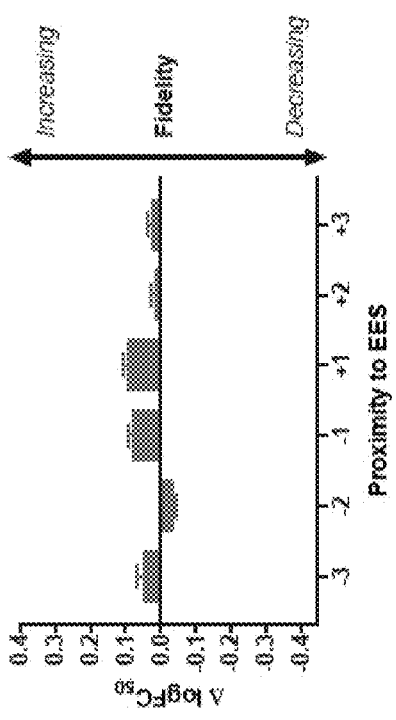
Figure 14C:
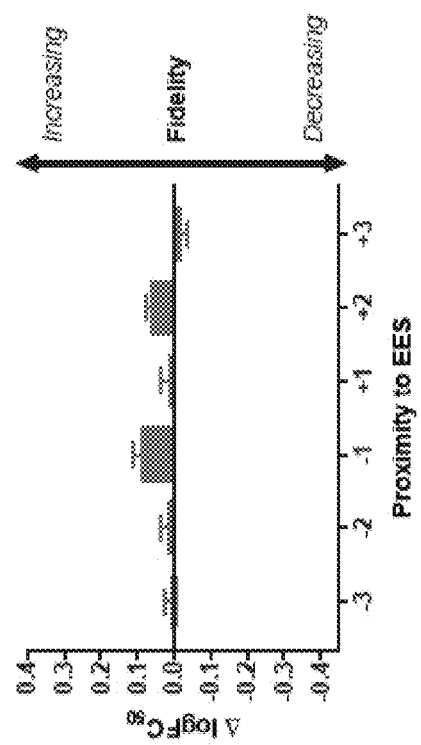
Figure 14C:
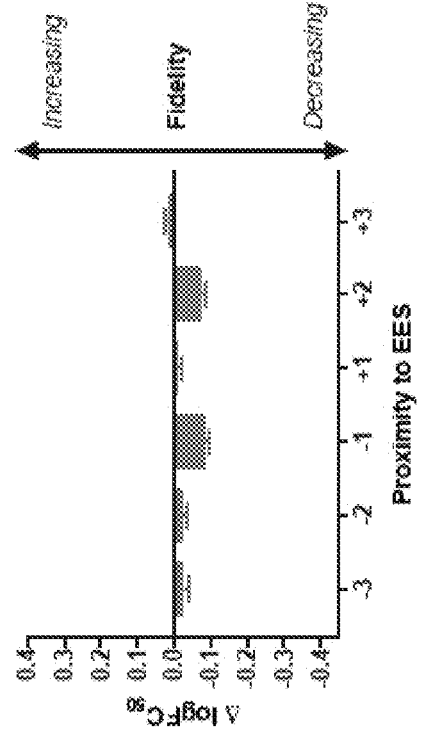
Figure 14C:
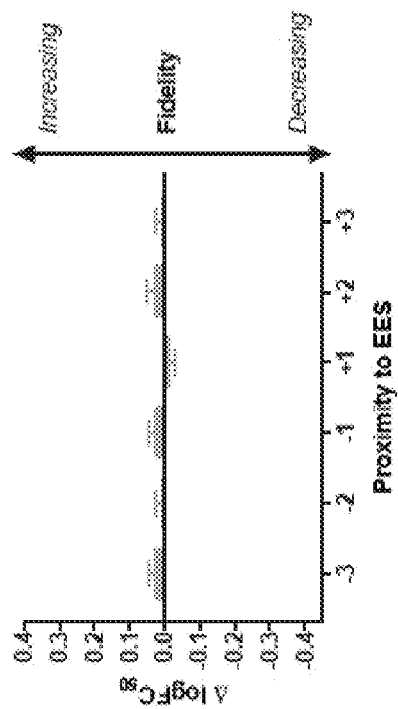
Figure 14D:
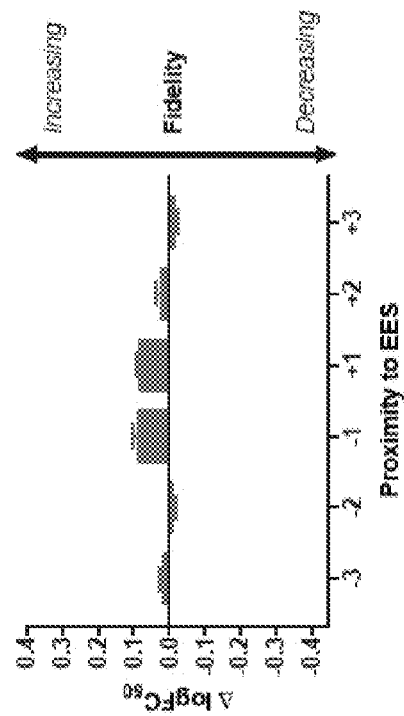
Figure 14D:
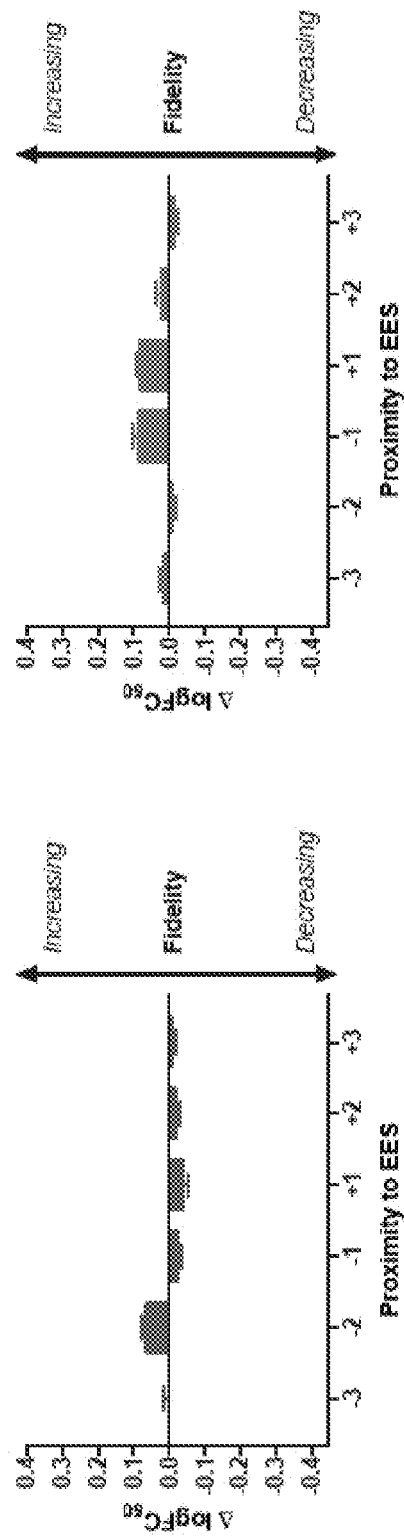
Figure 14D:
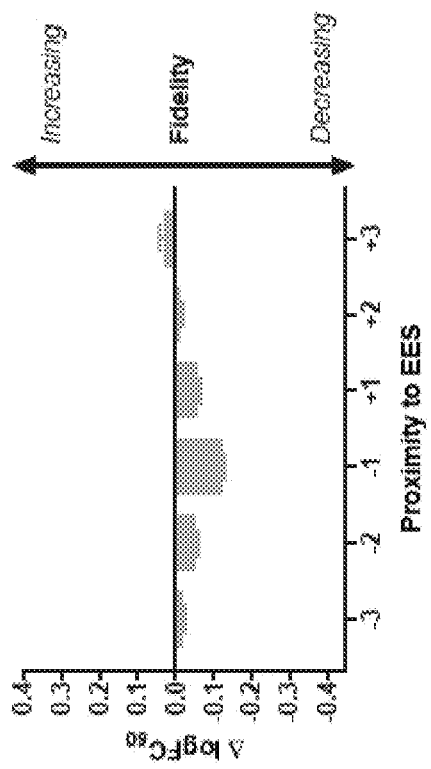
Figure 15A:
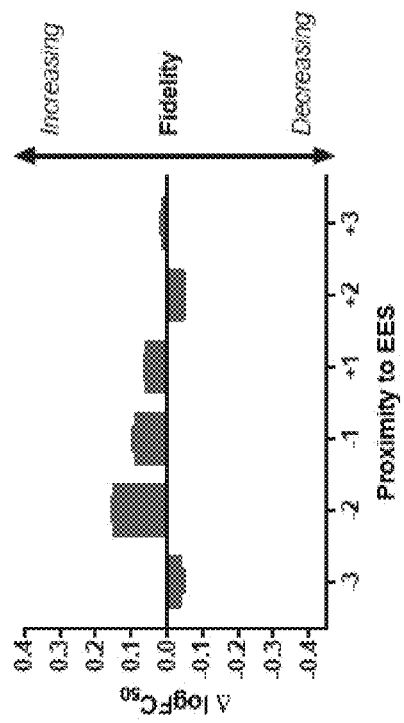
FIGS. 15A-15D: Effect of sequence context on $FC_{50}$ of Dpo4. The identity and position of template bases neighboring "T", "A", "C" and "G" EESs impact the measured $FC_{50}$ of Dpo4 copying in VVVTVVV (as shown in FIG. 15A), BBBABBB, (as shown in FIG. 15B) DDDCDDD (as shown in FIG. 15C), and HHHGHHH (as shown in FIG. 15D) template contexts, respectively. Change in log $FC_{50}$ (log $FC_{50}$_Average–log $FC_{50}$_Fixed Template Base) was calculated for each base identity/position. Positive Δ log $FC_{50}$ values pertain to an increase in fidelity whereas negative values signify a decrease in fidelity. Values represent the average of two experiments. Error bars signify standard deviation (n=2).
Figure 15A:
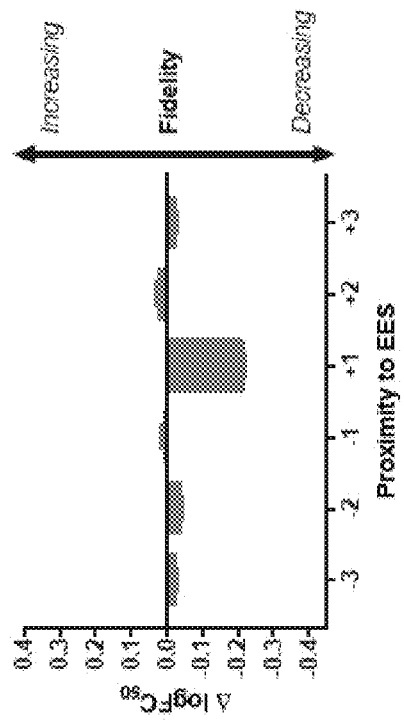
Figure 15A:
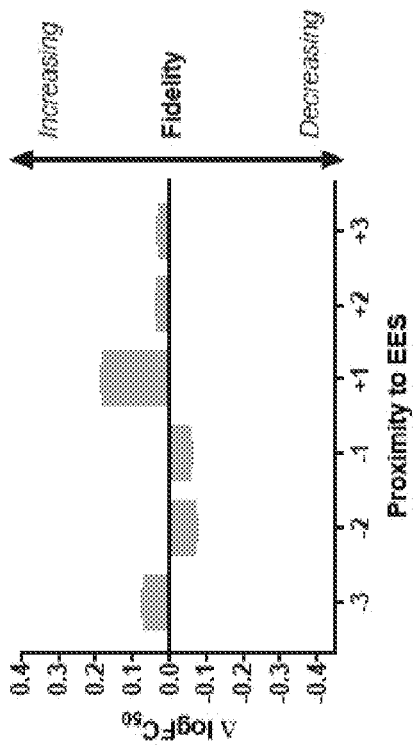
Figure 15B:
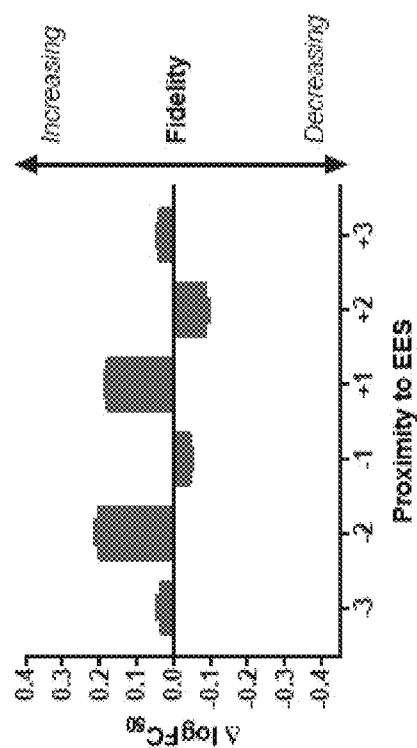
Figure 15B:
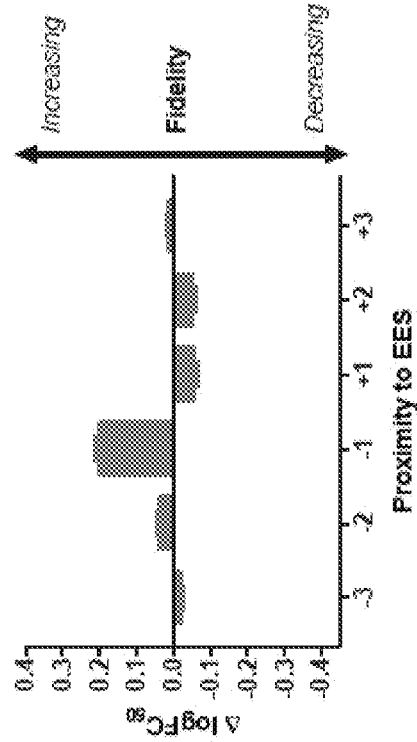
Figure 15B:
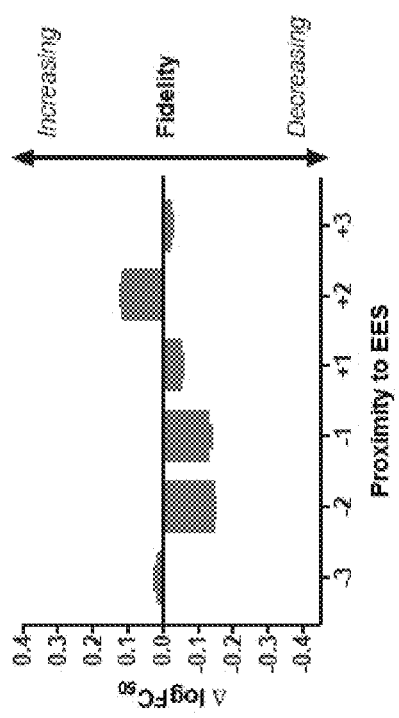
Figure 15C:
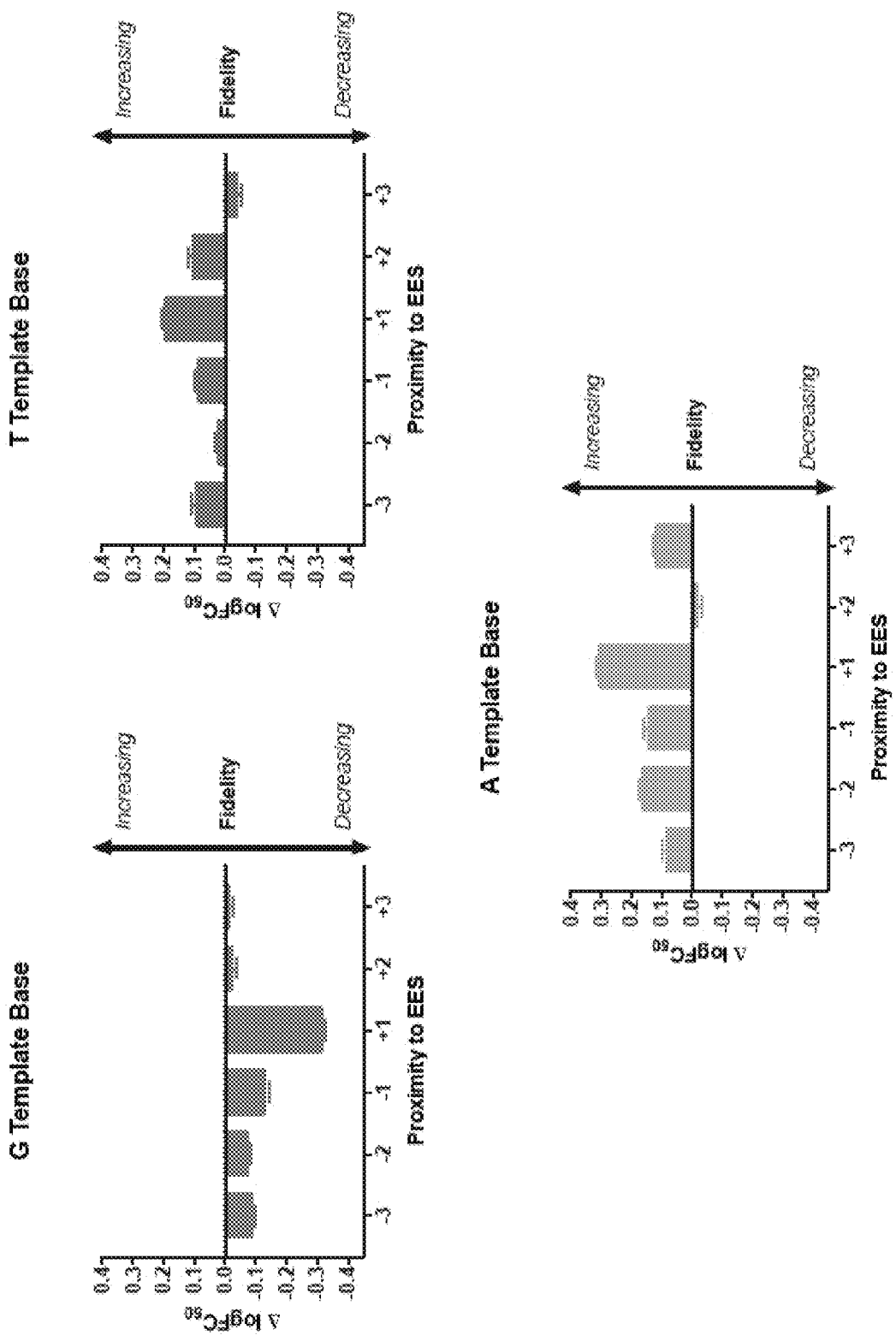
Figure 15D:
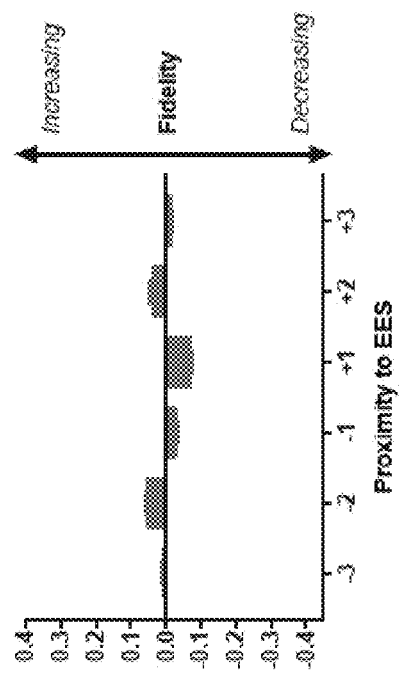
Figure 15D:
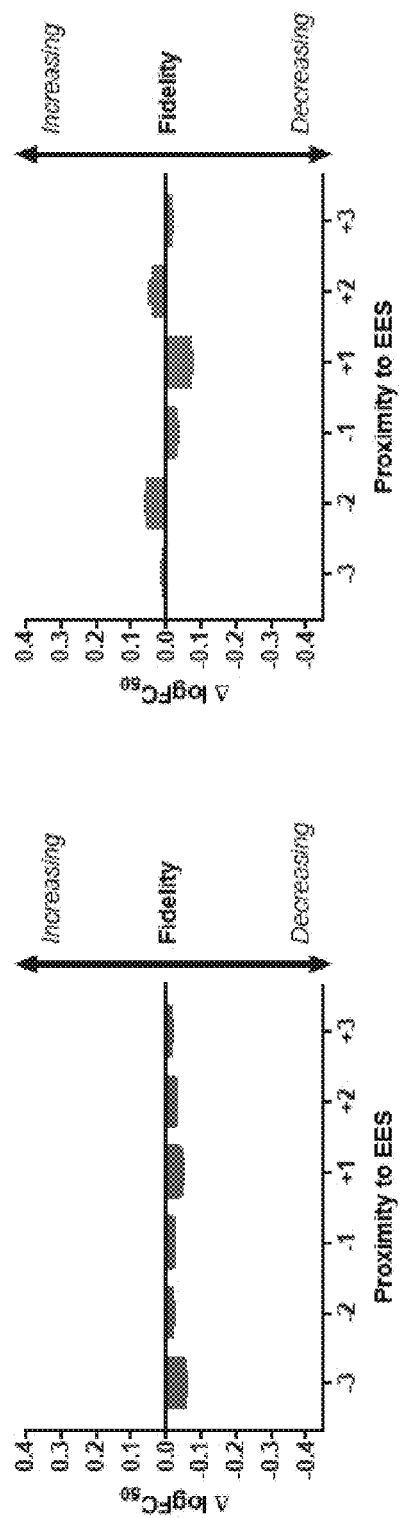
Figure 15D:
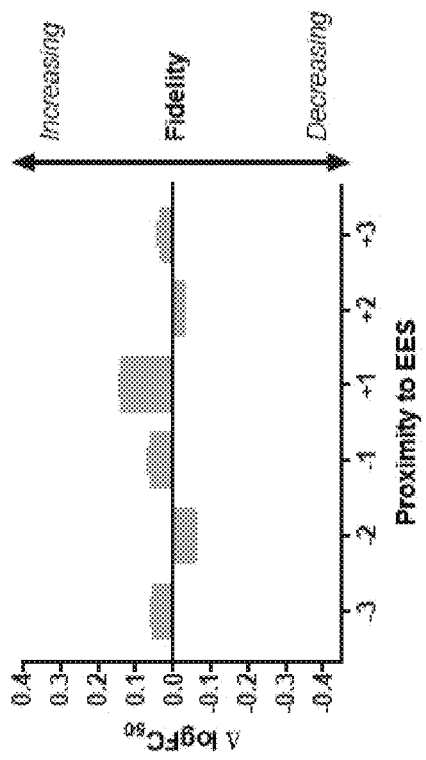
Figure 16:
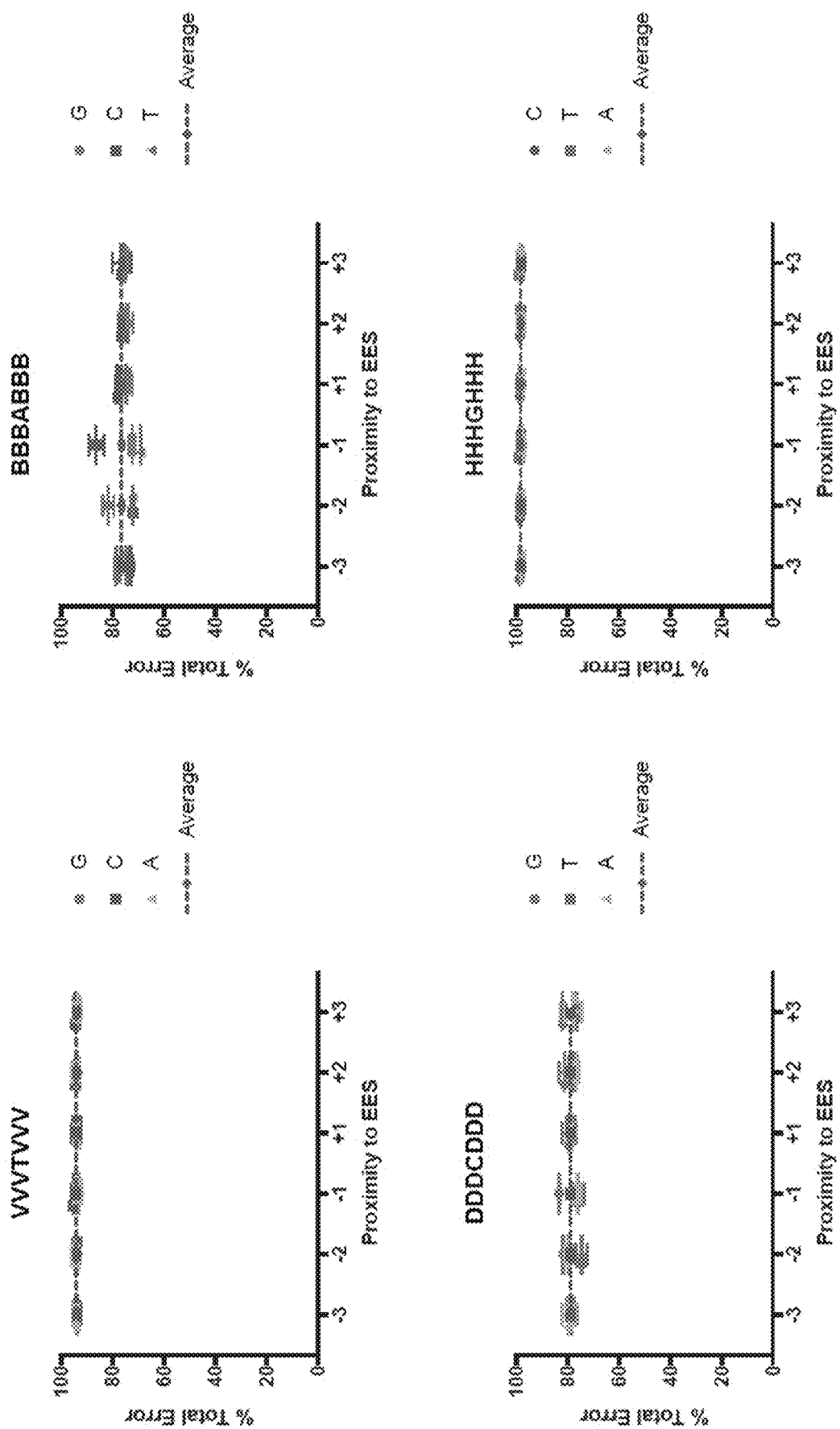
FIG. 16. Effect of sequence context on Sequenase 2.0 total error. Impact of identity and position of template bases flanking "T", "A", "C" and "G" EESs on the % total error Sequenase 2.0 creates at $10^{-7}$ μM dRTP when copying in VVVTVVV, BBBABBB, DDDCDDD, and HHHGHHH template contexts, respectively. A grey dotted line represents the average total error made by Sequenase 2.0 in a given context. Values represent the average of two experiments. Error bars signify standard deviation (n=2).
Figure 17:
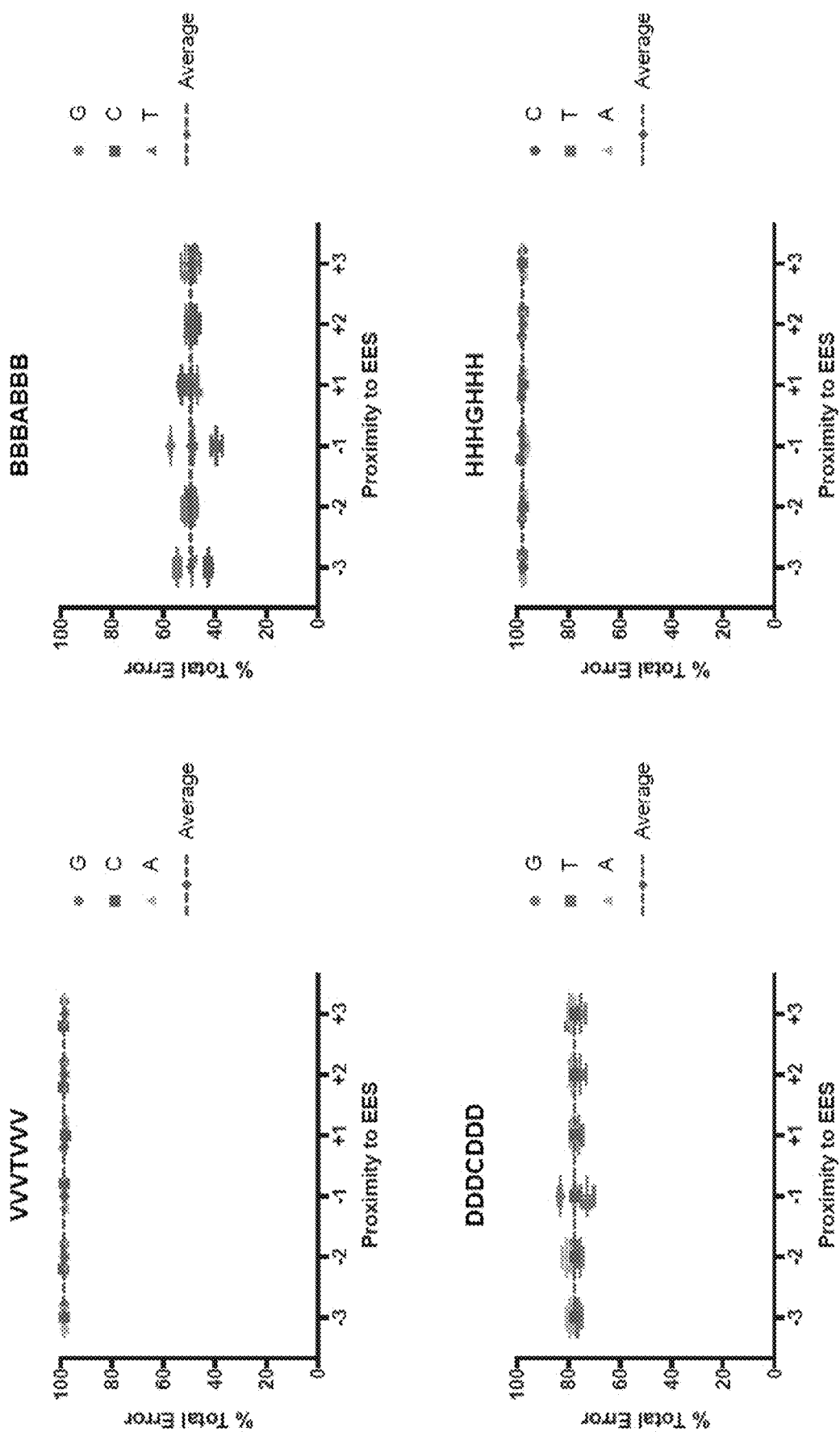
FIG. 17. Effect of sequence context on AMV RT total error. Impact of identity and position of template bases flanking "T", "A", "C" and "G" EESs on the % total error AMV RT creates at $10^{-7}$ μM dRTP when copying in VVVTVVV, BBBABBB, DDDCDDD, and HHHGHHH template contexts, respectively. A grey dotted line represents the average total error made by AMV RT in a given context. Values represent the average of two experiments. Error bars signify standard deviation (n=2).
Figure 18:
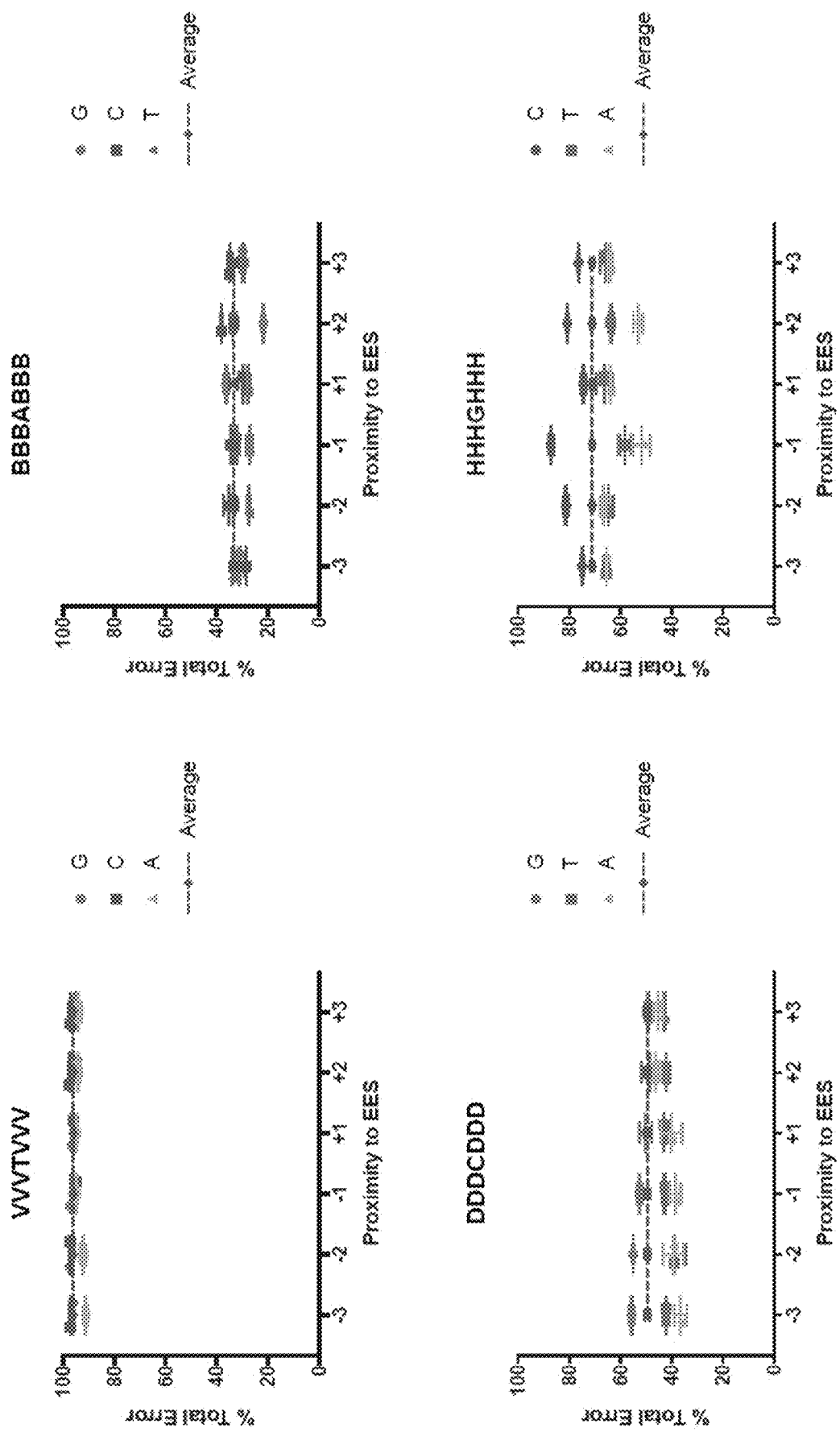
FIG. 18. Effect of sequence context on Phi29 total error. Impact of identity and position of template bases flanking "T", "A", "C" and "G" EESs on the % total error Phi29 creates at $10^{-7}$ μM dRTP when copying in VVVTVVV, BBBABBB, DDDCDDD, and HHHGHHH template contexts, respectively. A grey dotted line represents the average total error made by Phi29 in a given context. Values represent the average of two experiments. Error bars signify standard deviation (n=2).
Figure 19:
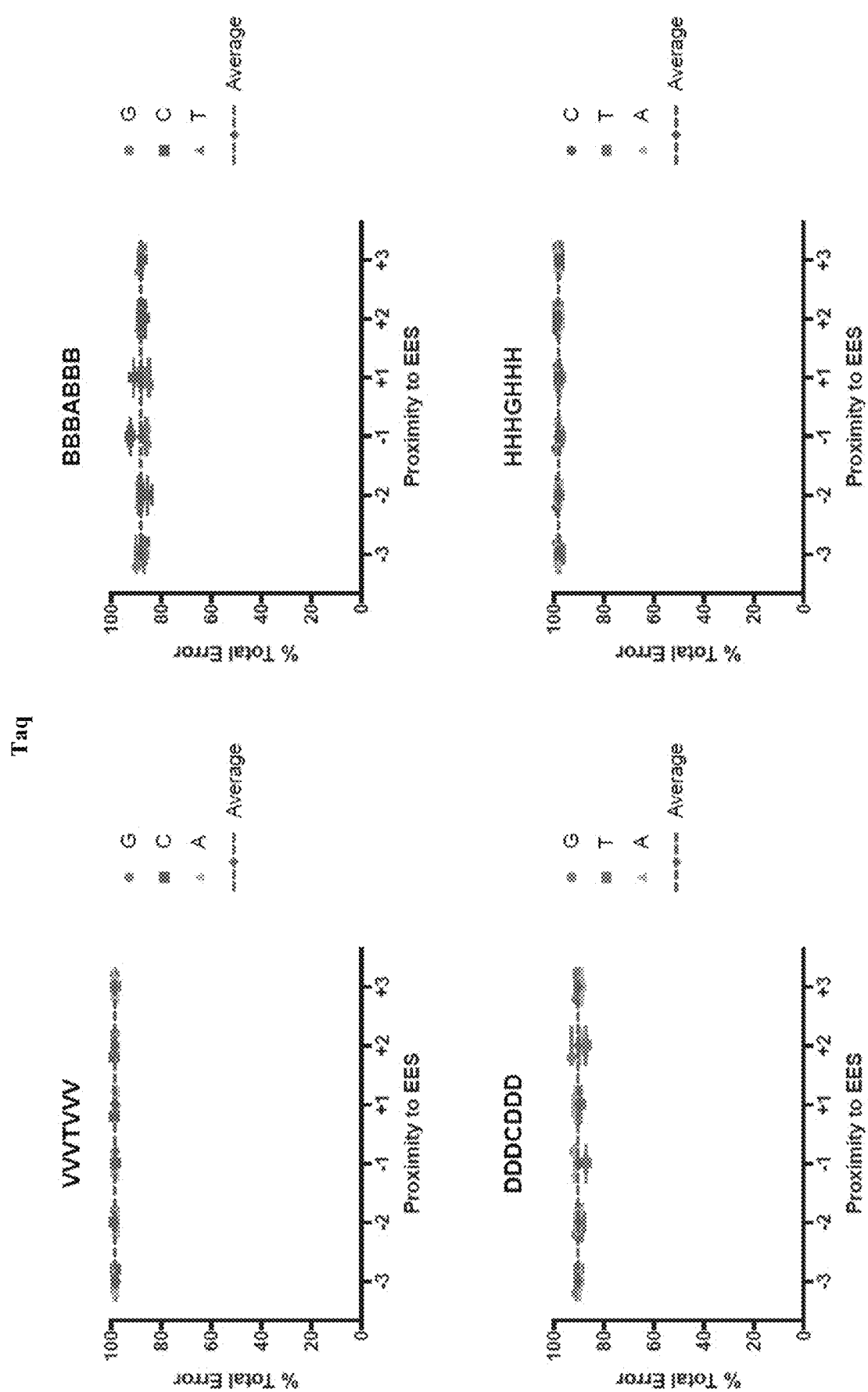
FIG. 19. Effect of sequence context on Taq total error. Impact of identity and position of template bases flanking "T", "A", "C" and "G" EESs on the % total error Taq creates at $10^{-7}$ μM dRTP when copying in VVVTVVV, BBBABBB, DDDCDDD, and HHHGHHH template contexts, respectively. A grey dotted line represents the average total error made by Taq in a given context. Values represent the average of two experiments. Error bars signify standard deviation (n=2).
Figure 20:
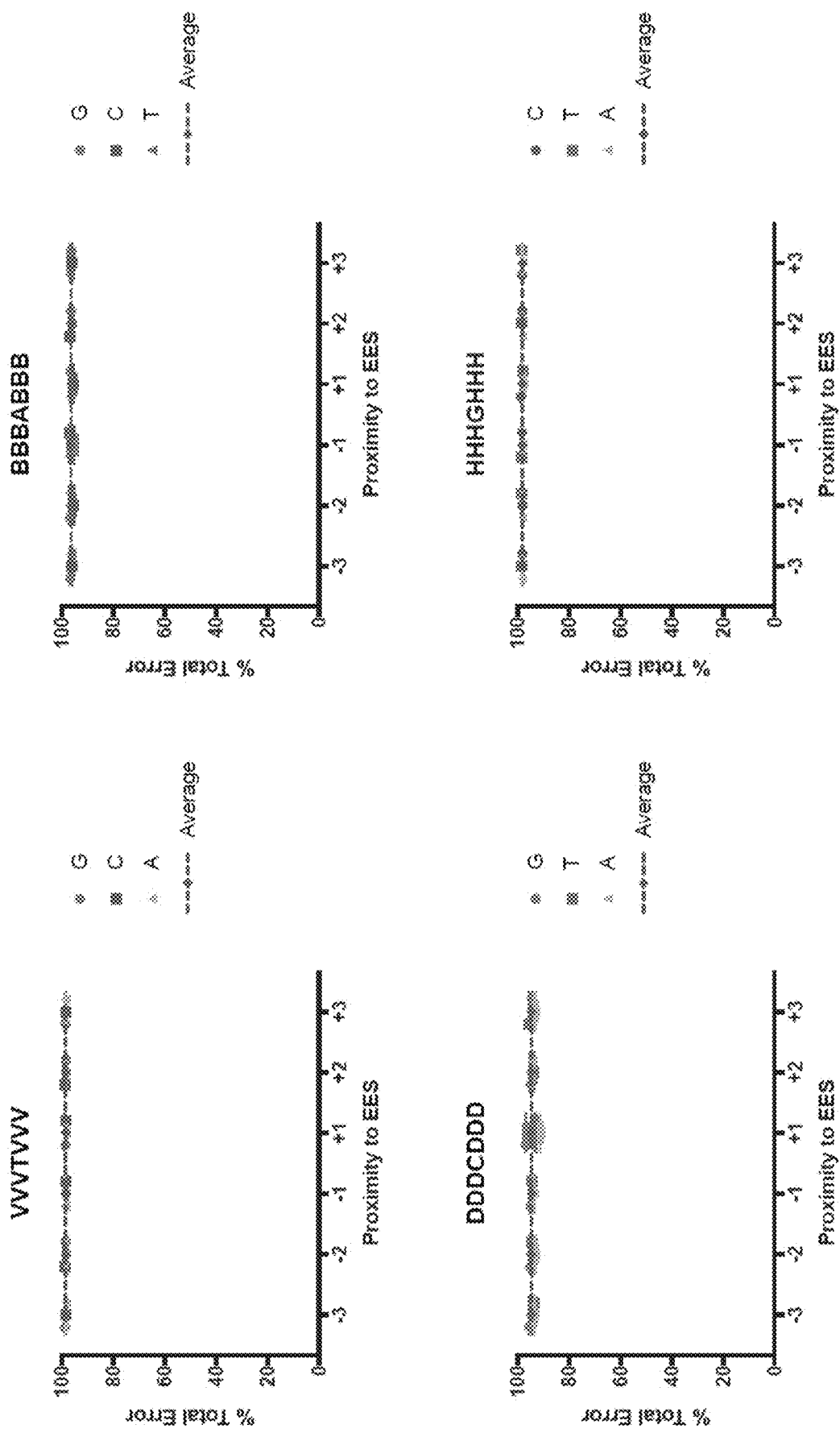
FIG. 20. Effect of sequence context on Dpo4 total error. Impact of identity and position of template bases flanking "T", "A", "C" and "G" EESs on the % total error Dpo4 creates at $10^{-7}$ μM dRTP when copying in VVVTVVV, BBBABBB, DDDCDDD, and HHHGHHH template contexts, respectively. A grey dotted line represents the average total error made by Dpo4 in a given context. Values represent the average of two experiments. Error bars signify standard deviation (n=2).
Figure 21A:
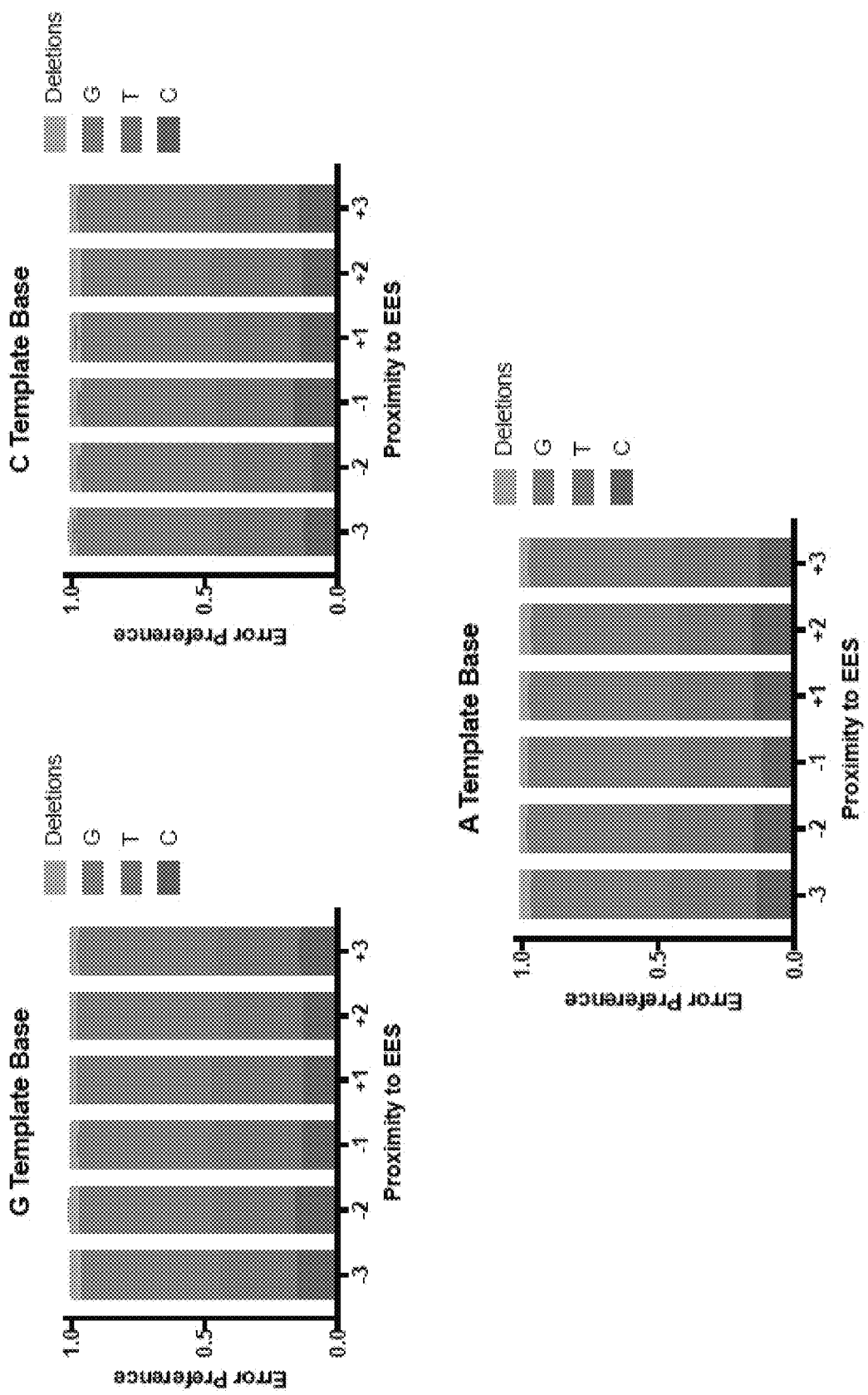
Figure 21C:
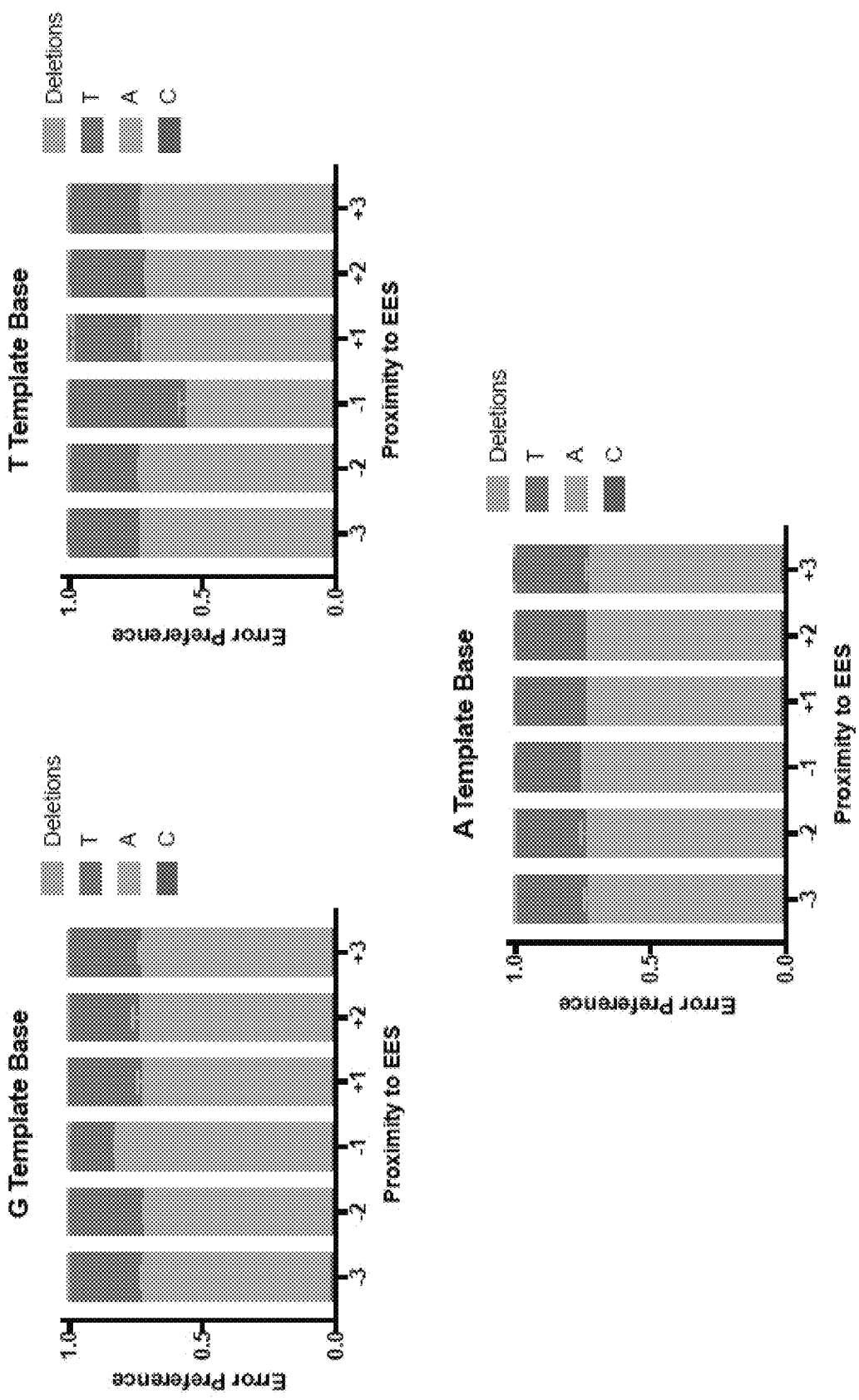
Figure 21D:
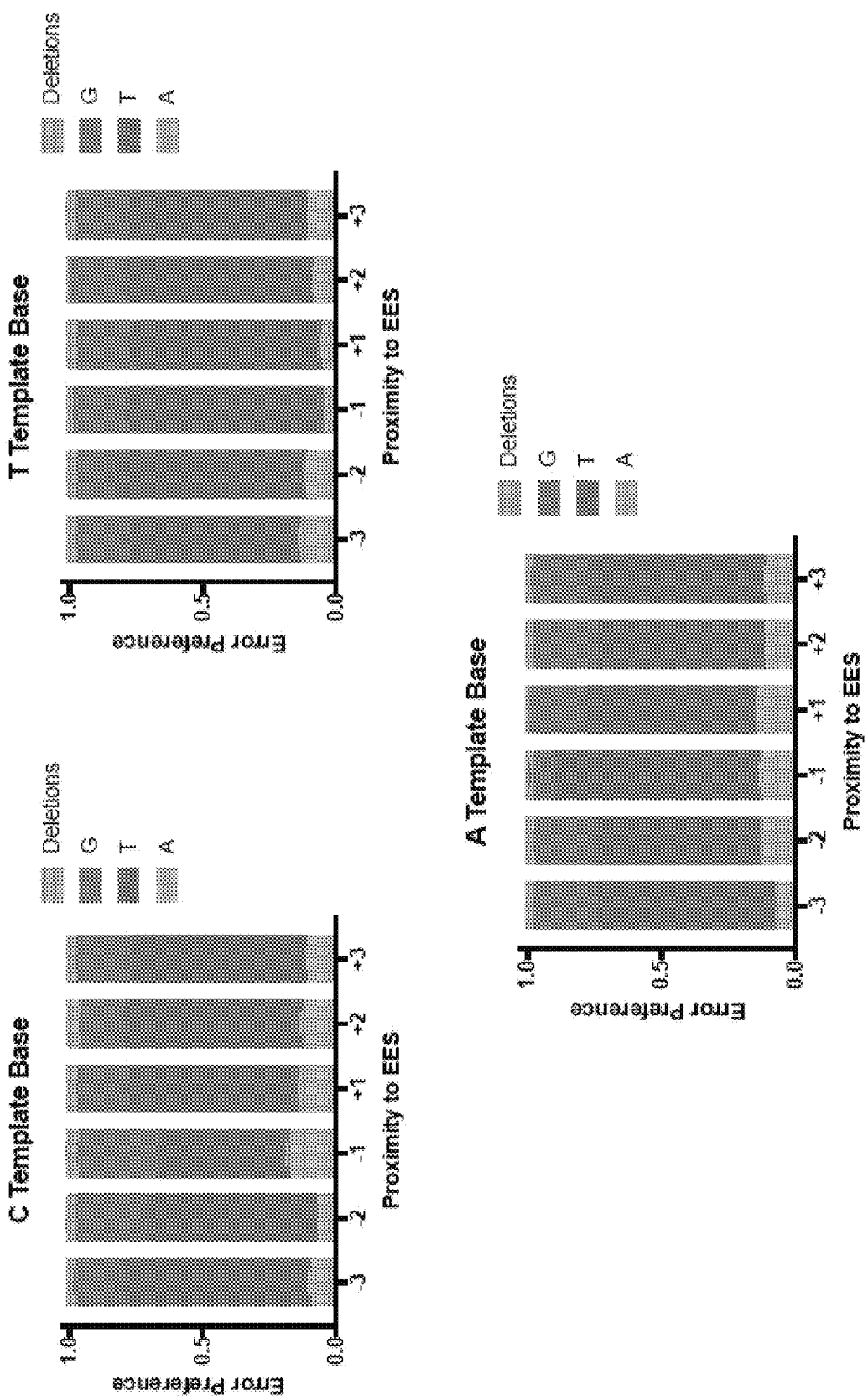
Figure 22A:
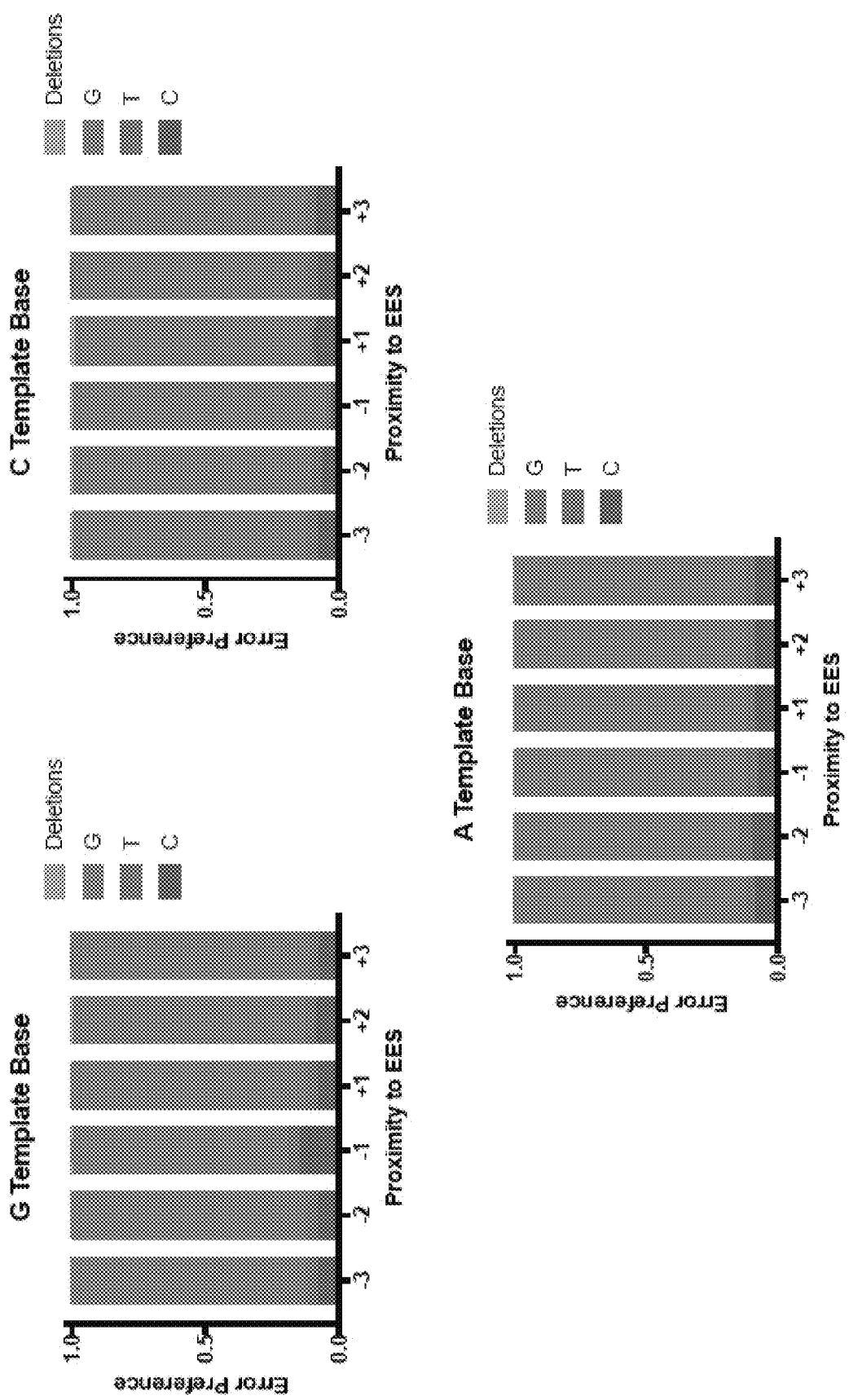
FIGS. 22A-22D: Effect of sequence context on AMV RT error preference. The identity and position of template bases flanking "T", "A", "C" and "G" EESs impact the distribution of preferred errors (nucleotide substitutions and deletions) created by AMV RT when copying in VVVTVVV (as shown in FIG. 22A), BBBABBB (as shown in FIG. 22B), DDDCDDD (as shown in FIG. 22C), and HHHGHHH (as shown in FIG. 22D) template contexts, respectively. Error preference was determined by normalizing error subtype frequency to the total error rate measured at $10^{-7}$ μM dRTP. Values represent the average of two experiments. Error bars signify standard deviation (n=2).
Figure 22B:
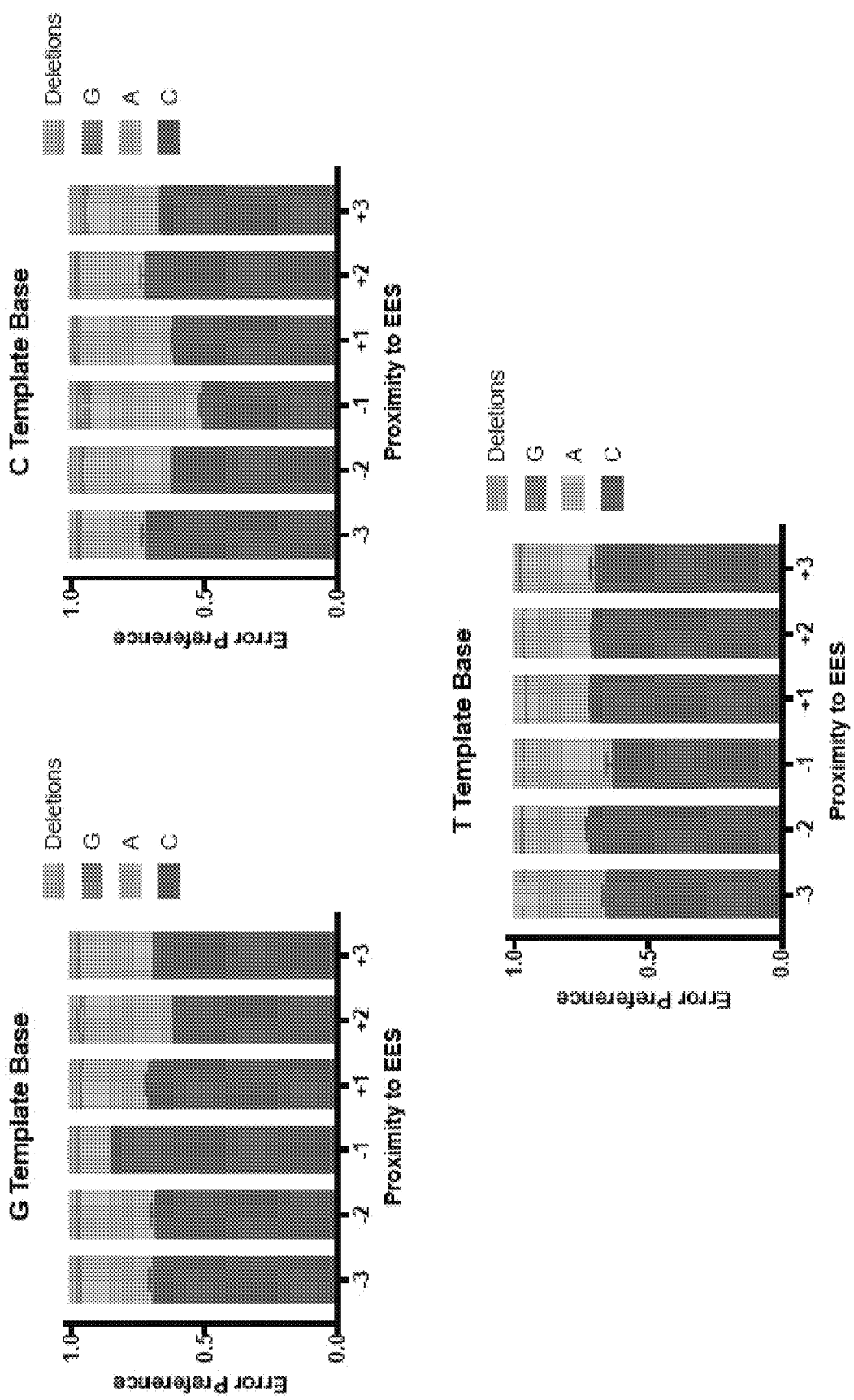
Figure 22C:
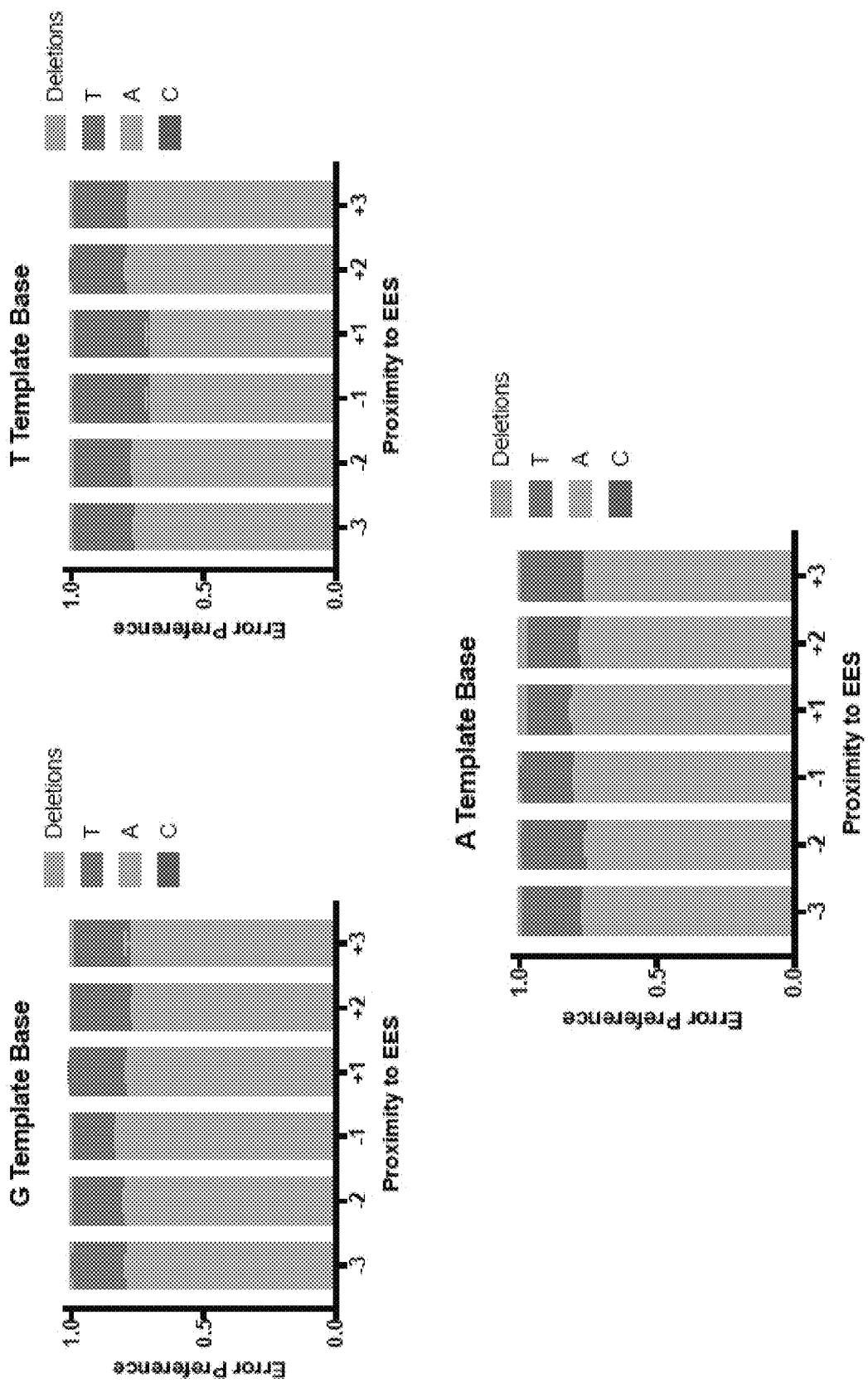
Figure 22D:
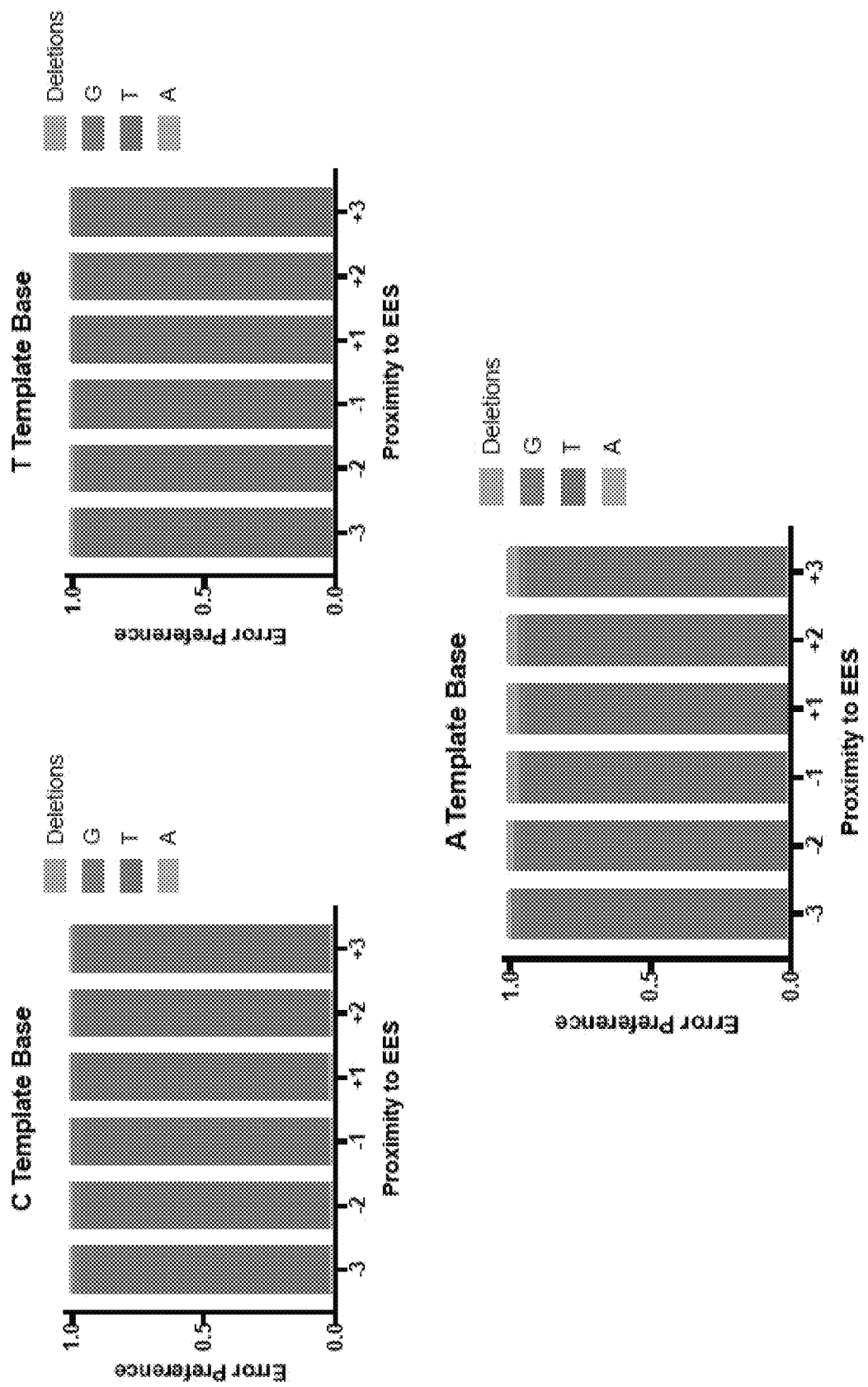
Figure 23A:
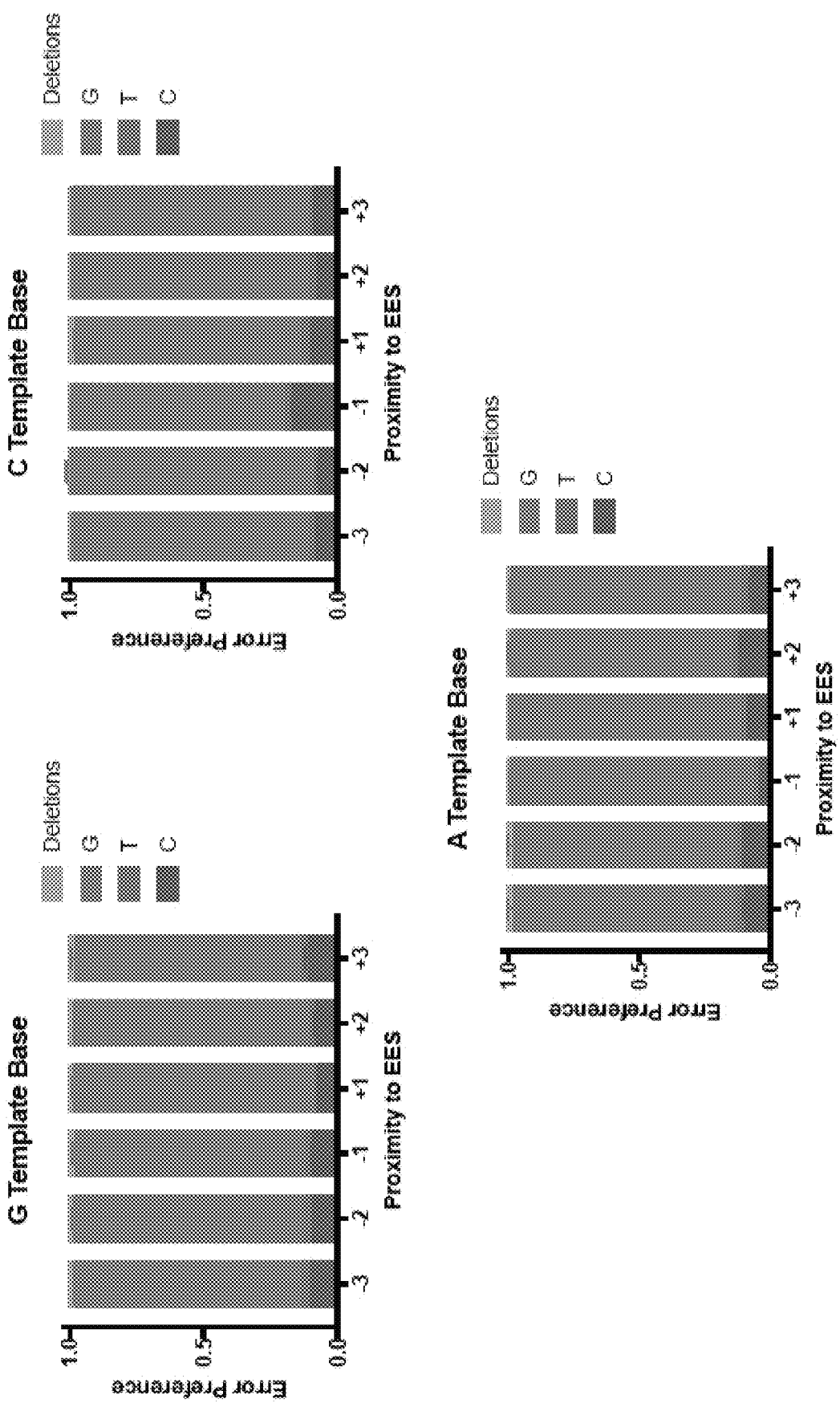
FIGS. 23A-23D: Effect of sequence context on Phi29 error preference. The identity and position of template bases flanking "T", "A", "C" and "G" EESs impact the distribution of preferred errors (nucleotide substitutions and deletions) created by Phi29 when copying in VVVTVVV (as shown in FIG. 23A), BBBABBB (as shown in FIG. 23B), DDDCDDD (as shown in FIG. 23C), and HHHGHHH (as shown in FIG. 23D) template contexts, respectively. Error preference was determined by normalizing error subtype frequency to the total error rate measured at $10^{-7}$ μM dRTP. Values represent the average of two experiments. Error bars signify standard deviation (n=2).
Figure 23B:
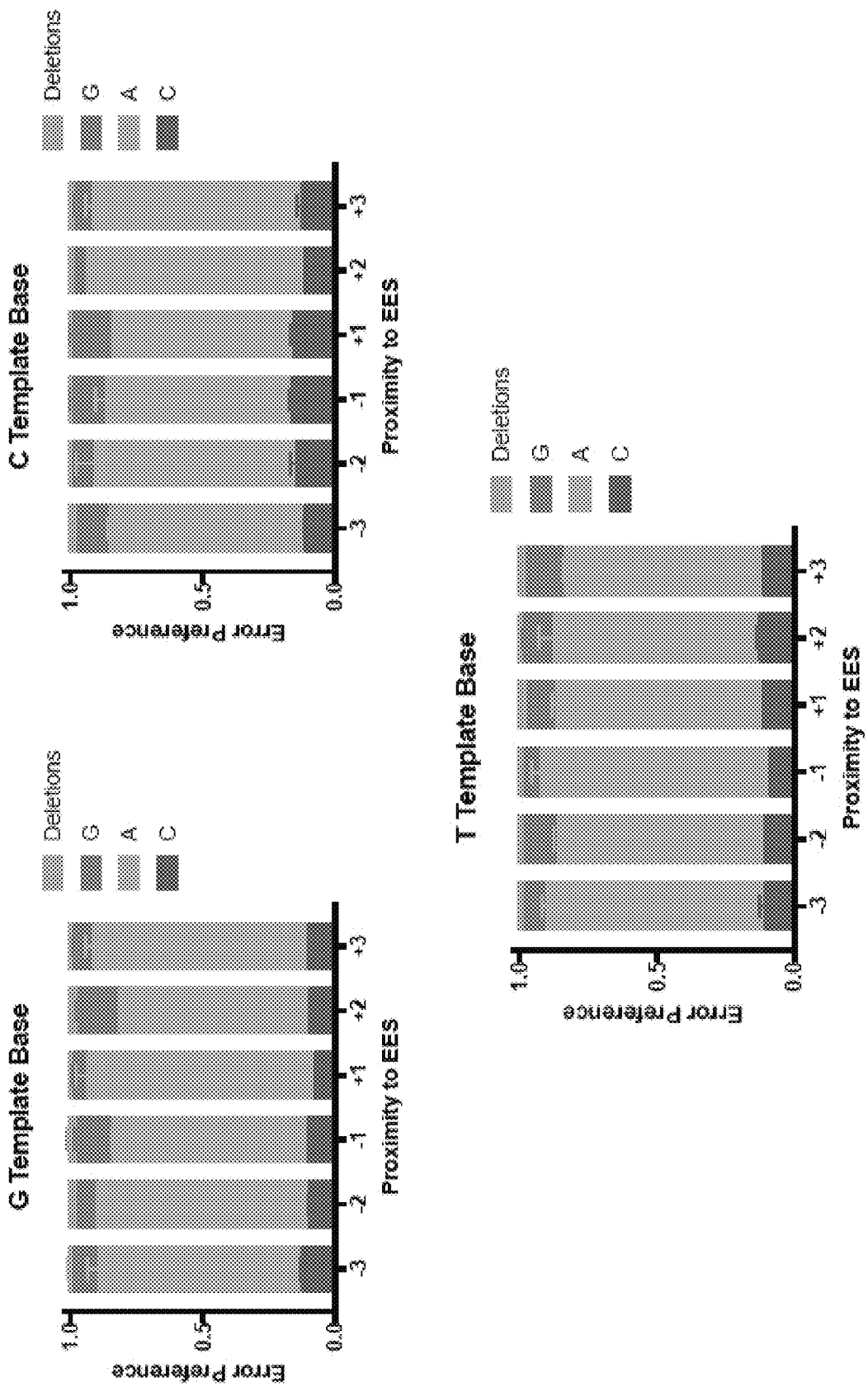
Figure 23C:
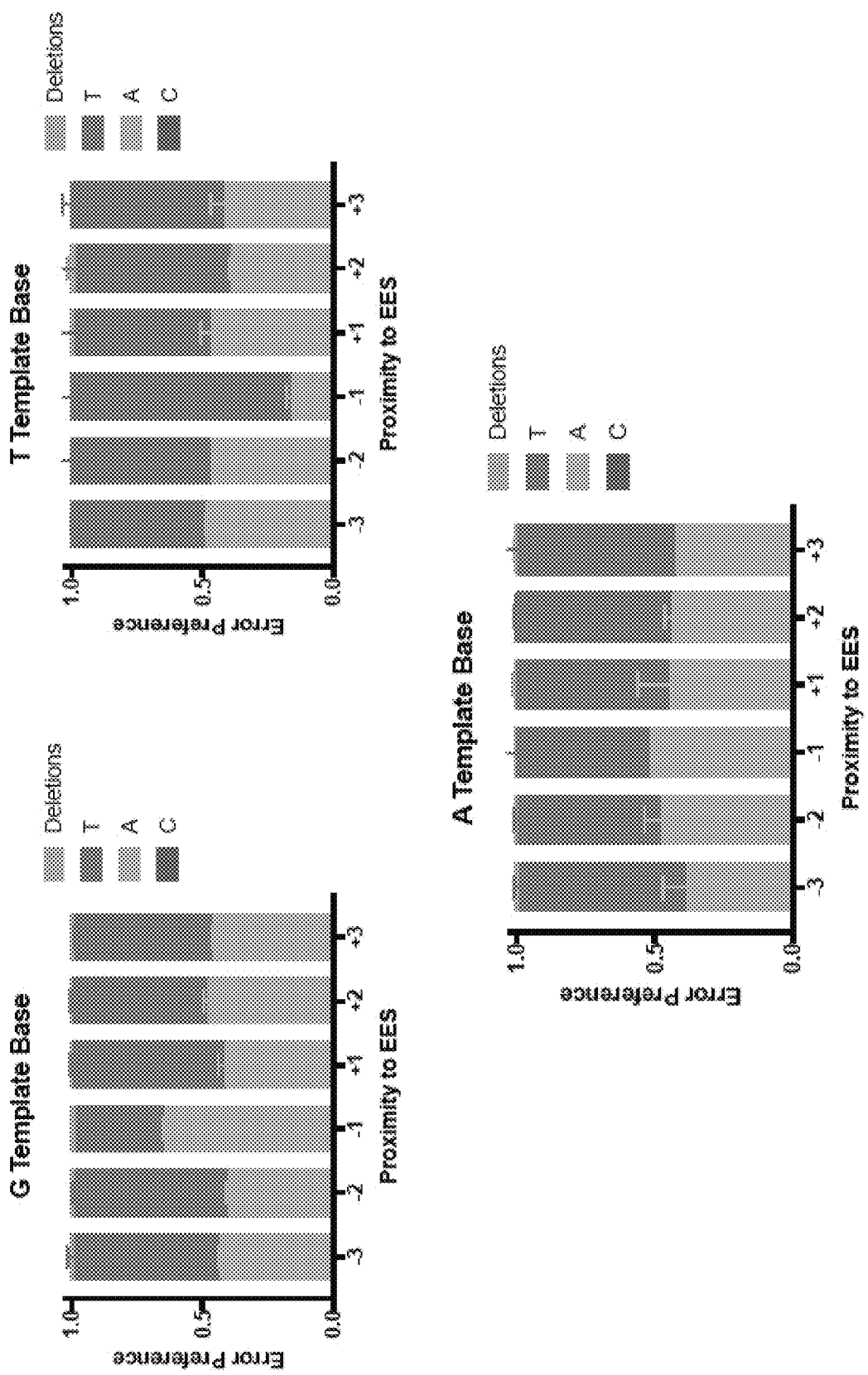
Figure 23D:
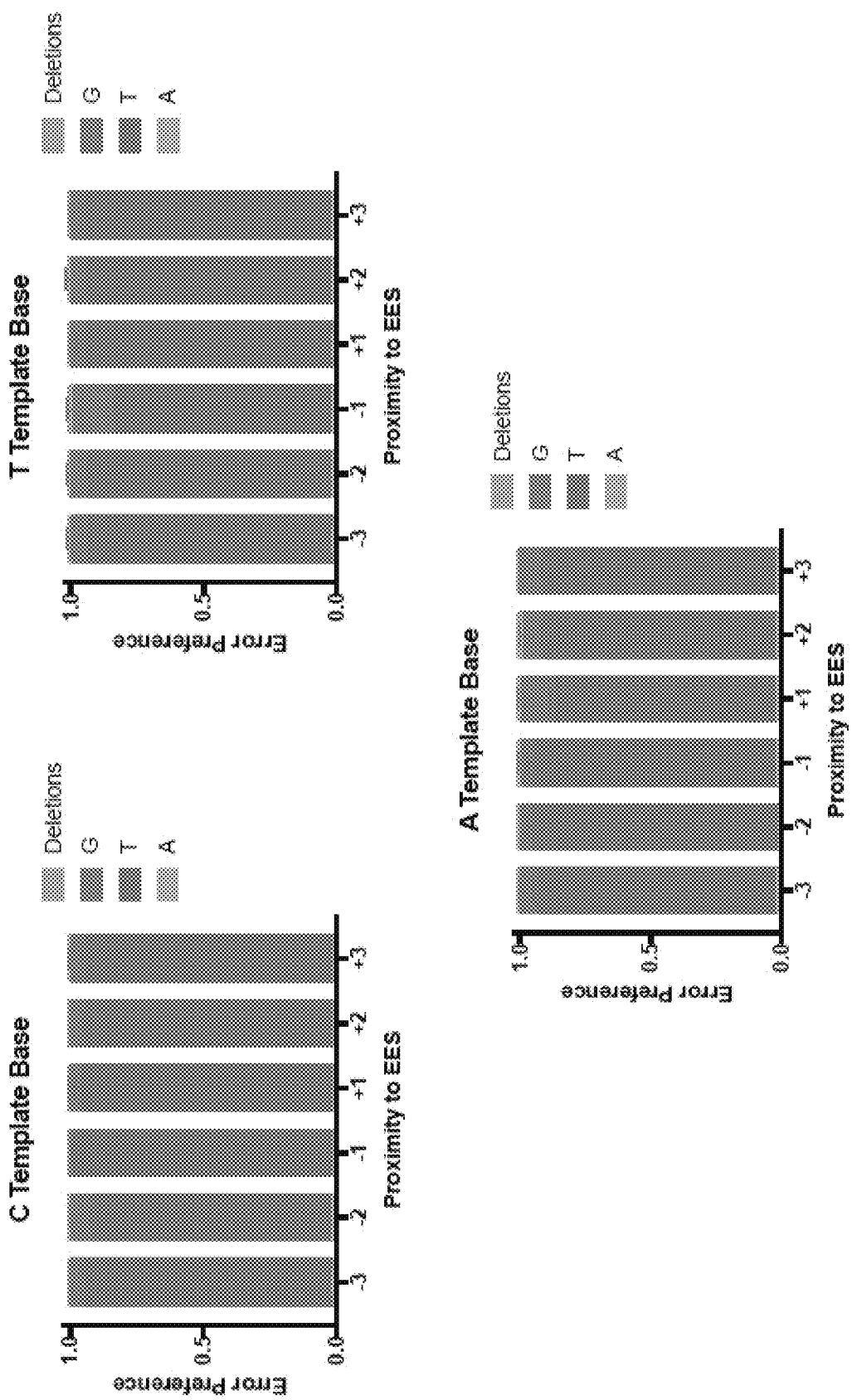
Figure 24A:
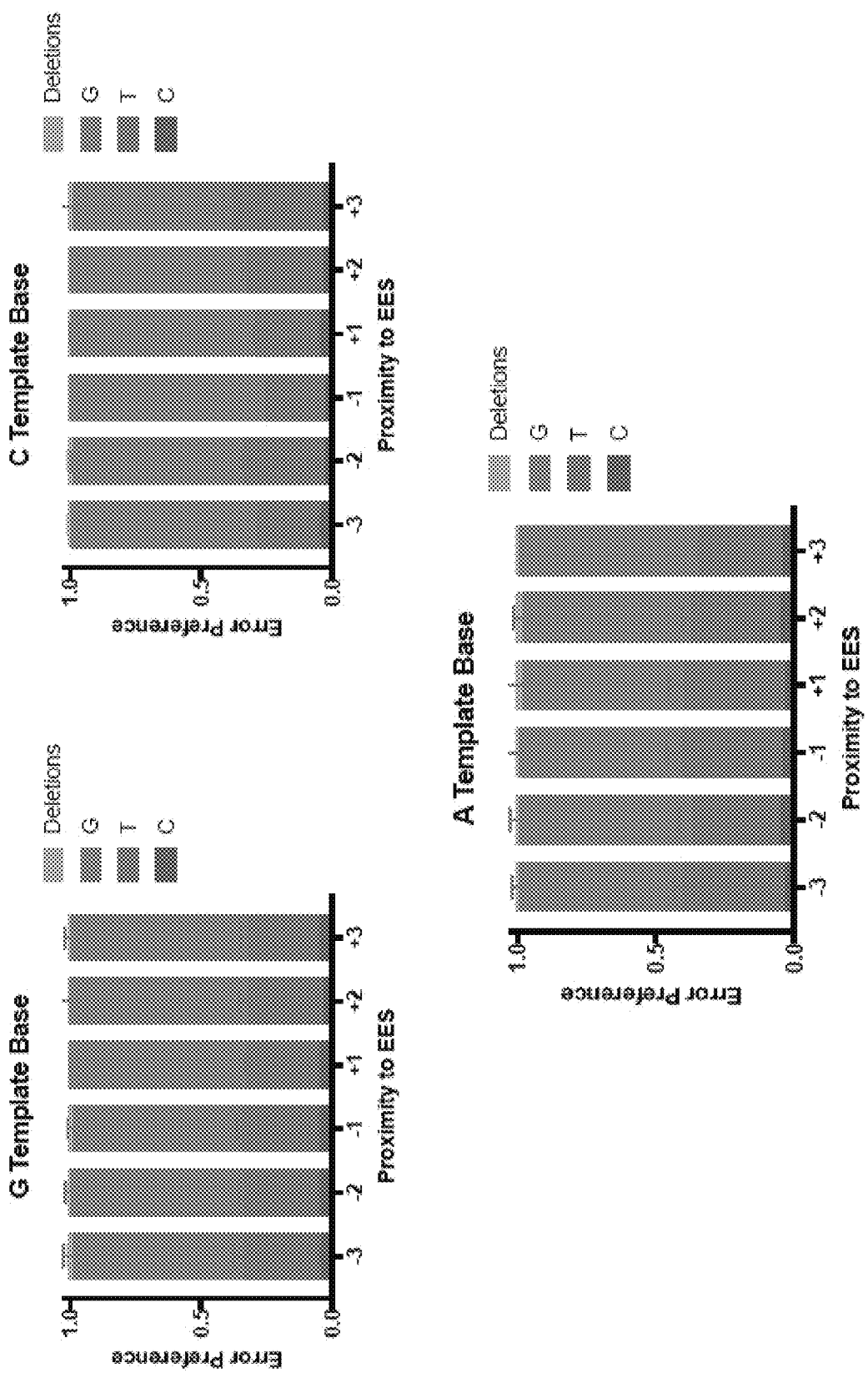
FIGS. 24A-24D: Effect of sequence context on Taq error preference. The identity and position of template bases flanking "T", "A", "C" and "G" EESs impact the distribution of preferred errors (nucleotide substitutions and deletions) created by Taq when copying in VVVTVVV (as shown in FIG. 24A), BBBABBB (as shown in FIG. 24B), DDDCDDD (as shown in FIG. 24C), and HHHGHHH (as shown in FIG. 24D) template contexts, respectively. Error preference was determined by normalizing error subtype frequency to the total error rate measured at $10^{-7}$ μM dRTP. Values represent the average of two experiments. Error bars signify standard deviation (n=2).
Figure 24B:
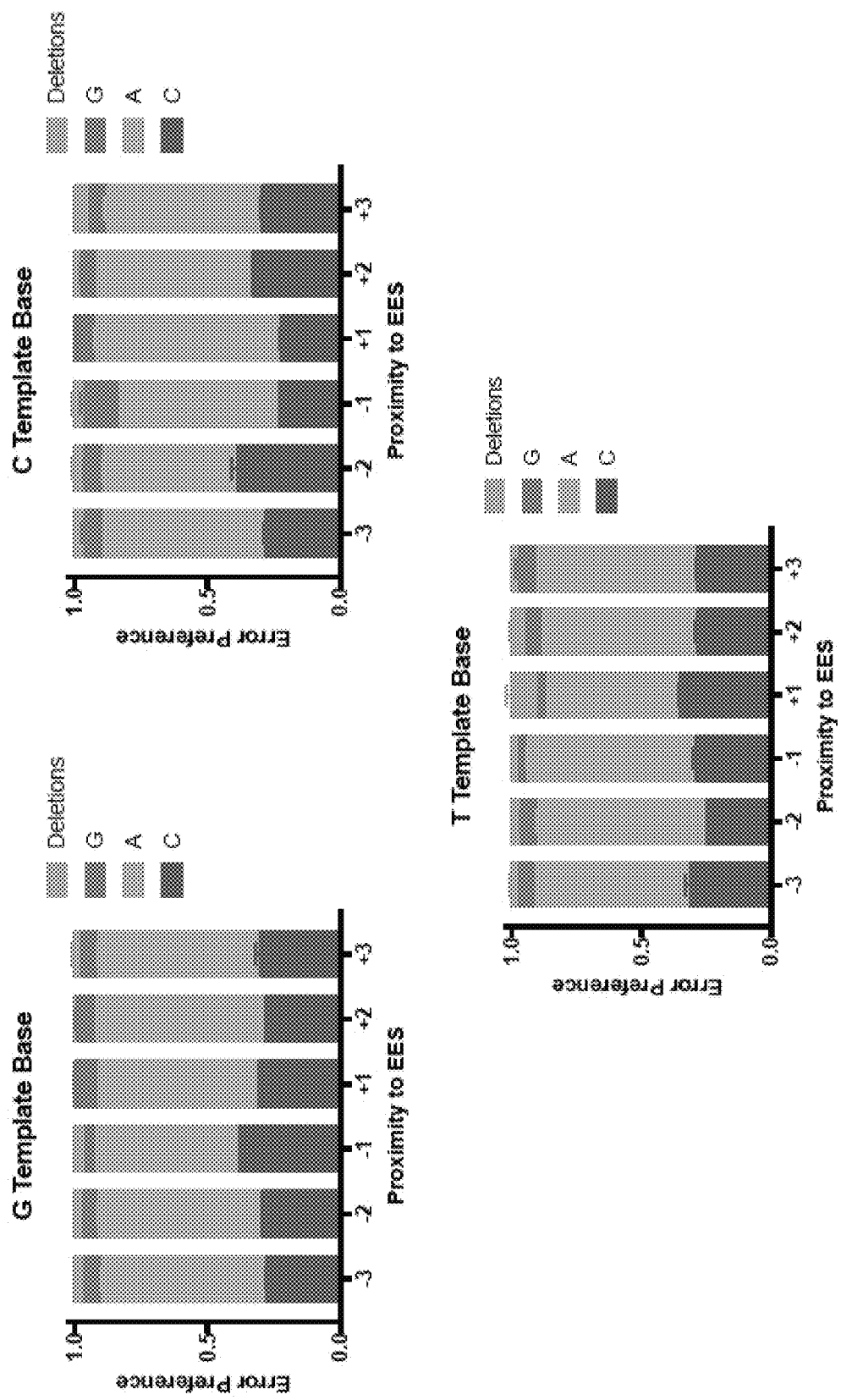
Figure 24C:
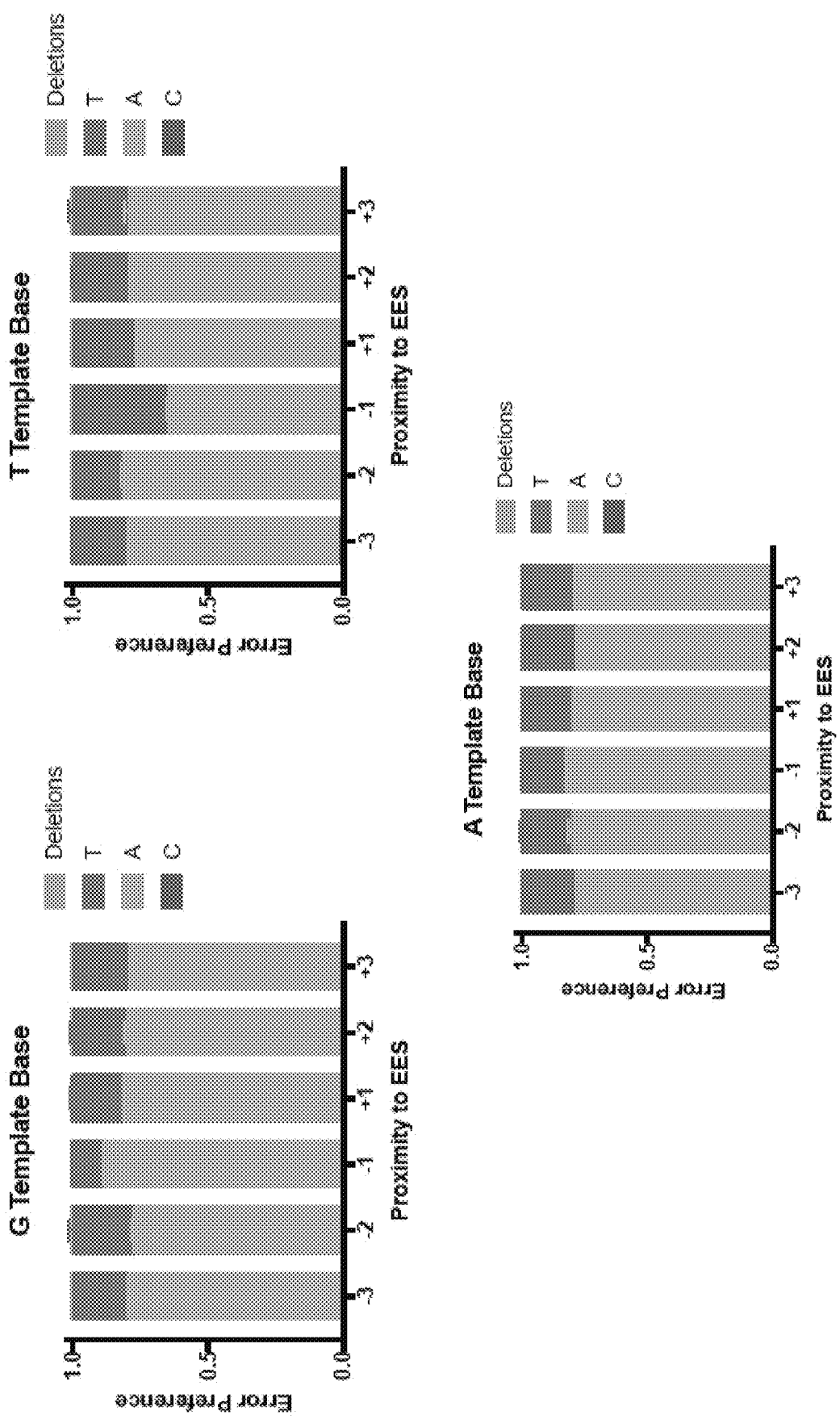
Figure 24D:
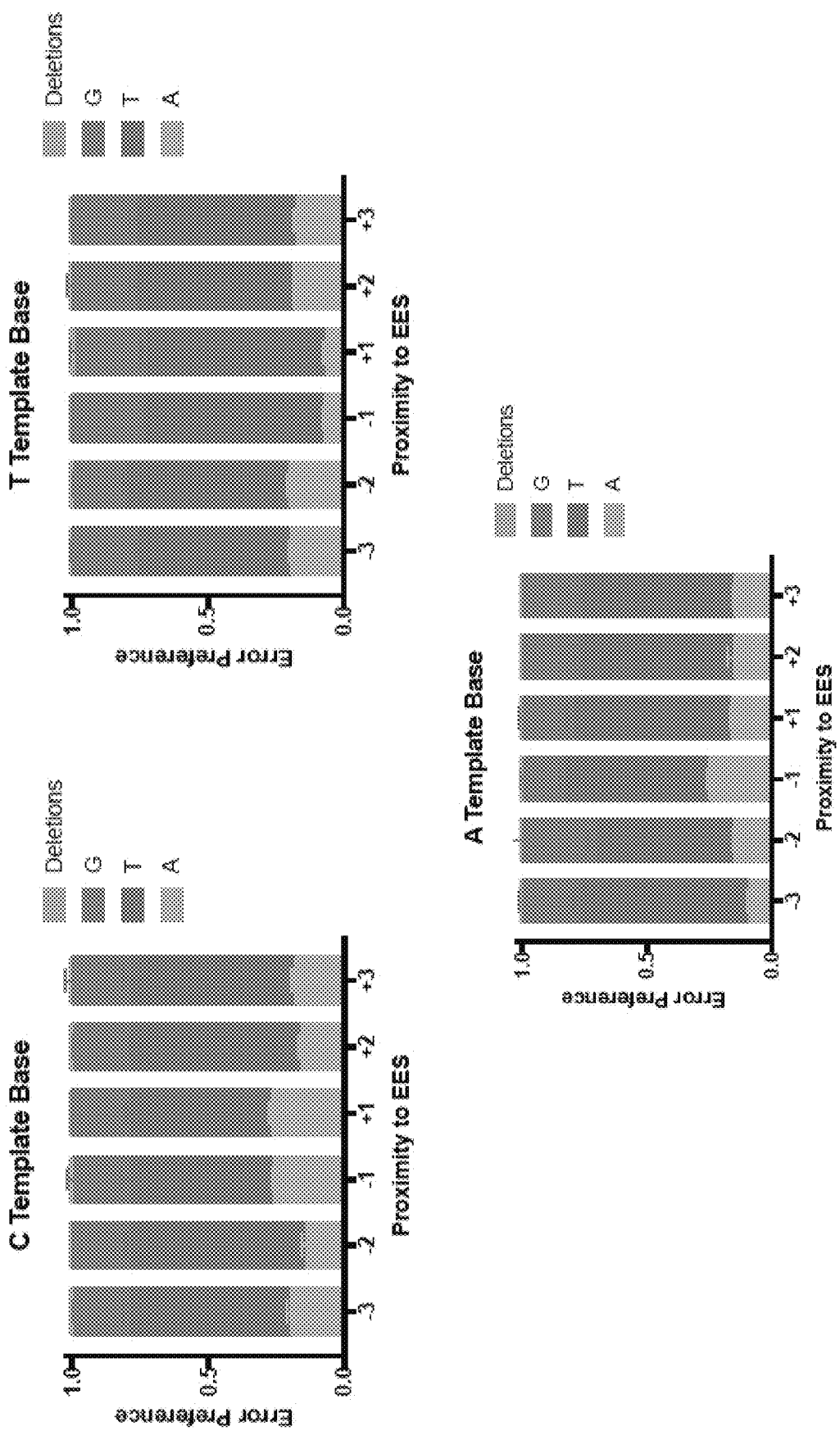
Figure 25A:
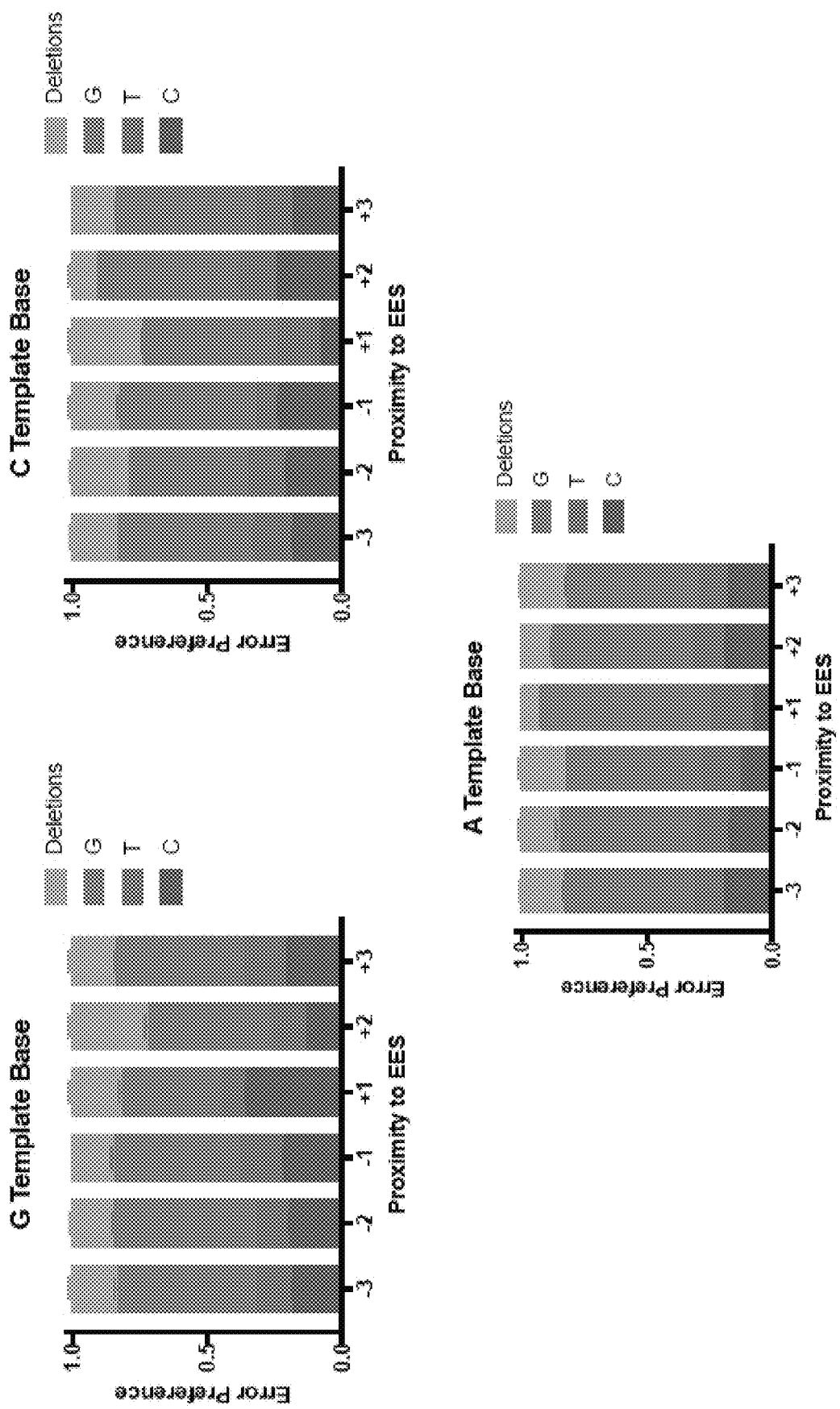
FIGS. 25A-25D: Effect of sequence context on Dpo4 error preference. The identity and position of template bases flanking "T", "A", "C" and "G" EESs impact the distribution of preferred errors (nucleotide substitutions and deletions) created by Dpo4 when copying in VVVTVVV (as shown in FIG. 25A), BBBABBB (as shown in FIG. 25B), DDDCDDD (as shown in FIG. 25C), and HHHGHHH (as shown in FIG. 25D) template contexts, respectively. Error preference was determined by normalizing error subtype frequency to the total error rate measured at $10^{-7}$ μM dRTP. Values represent the average of two experiments. Error bars signify standard deviation (n=2).
Figure 25B:
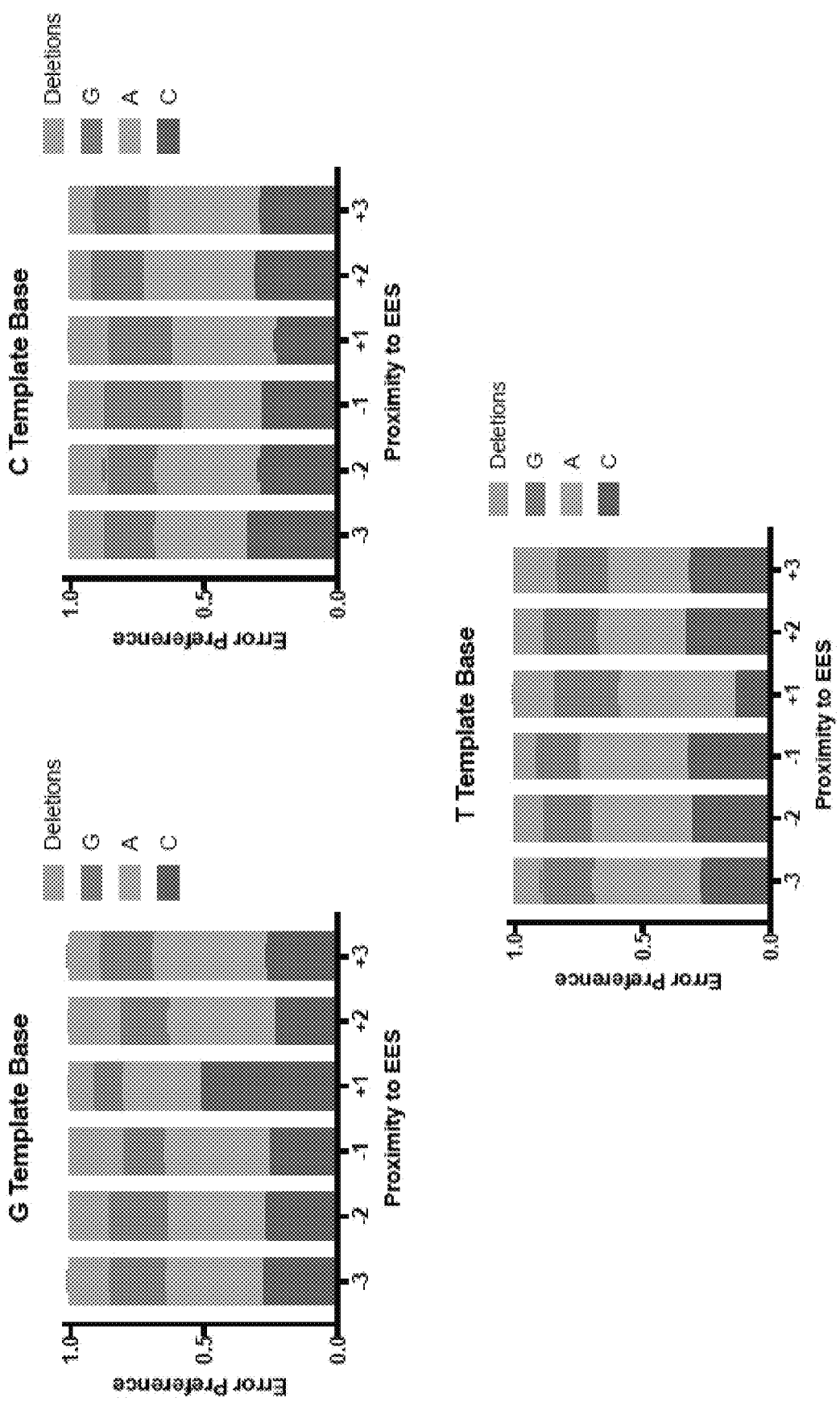
Figure 25C:
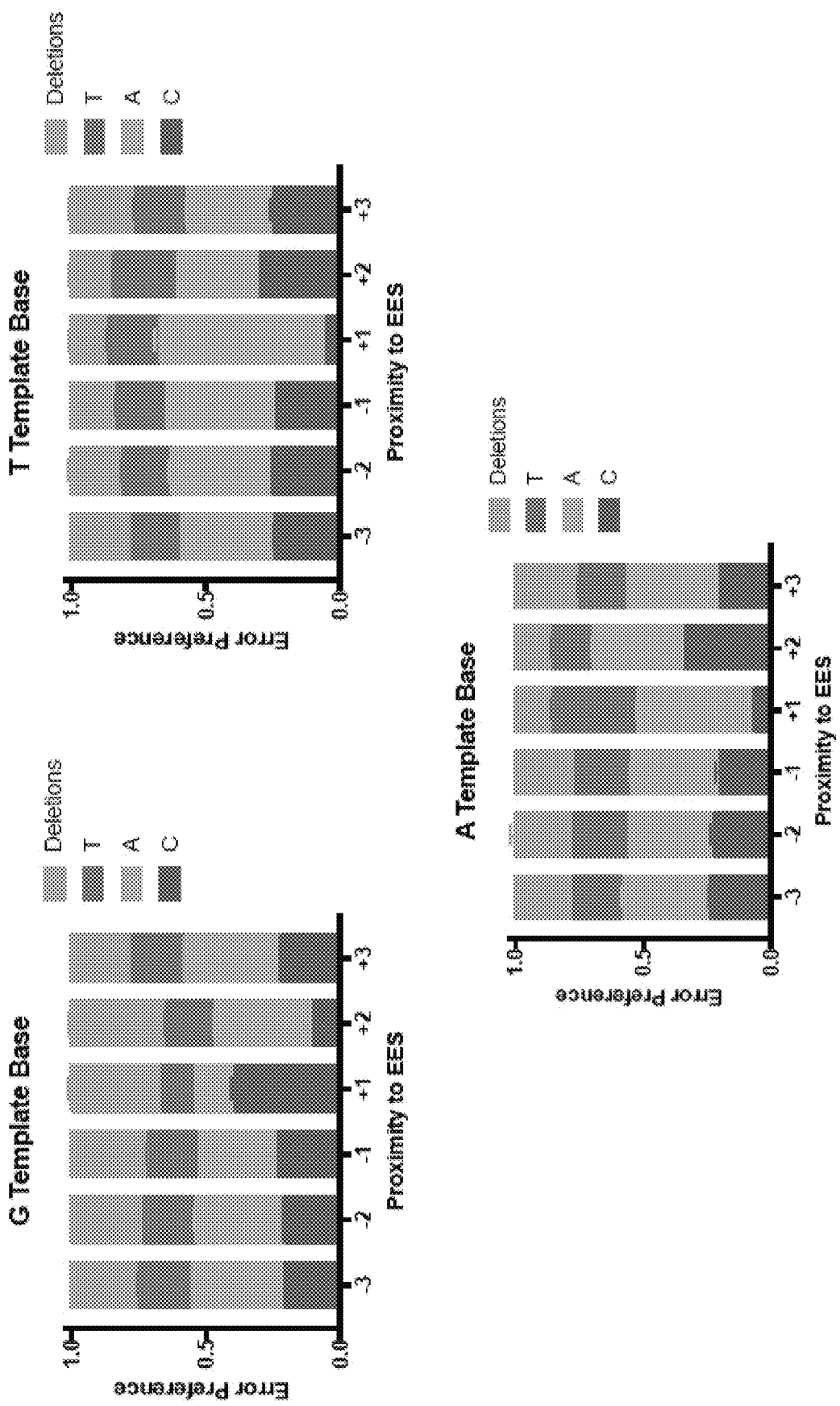
Figure 25D:
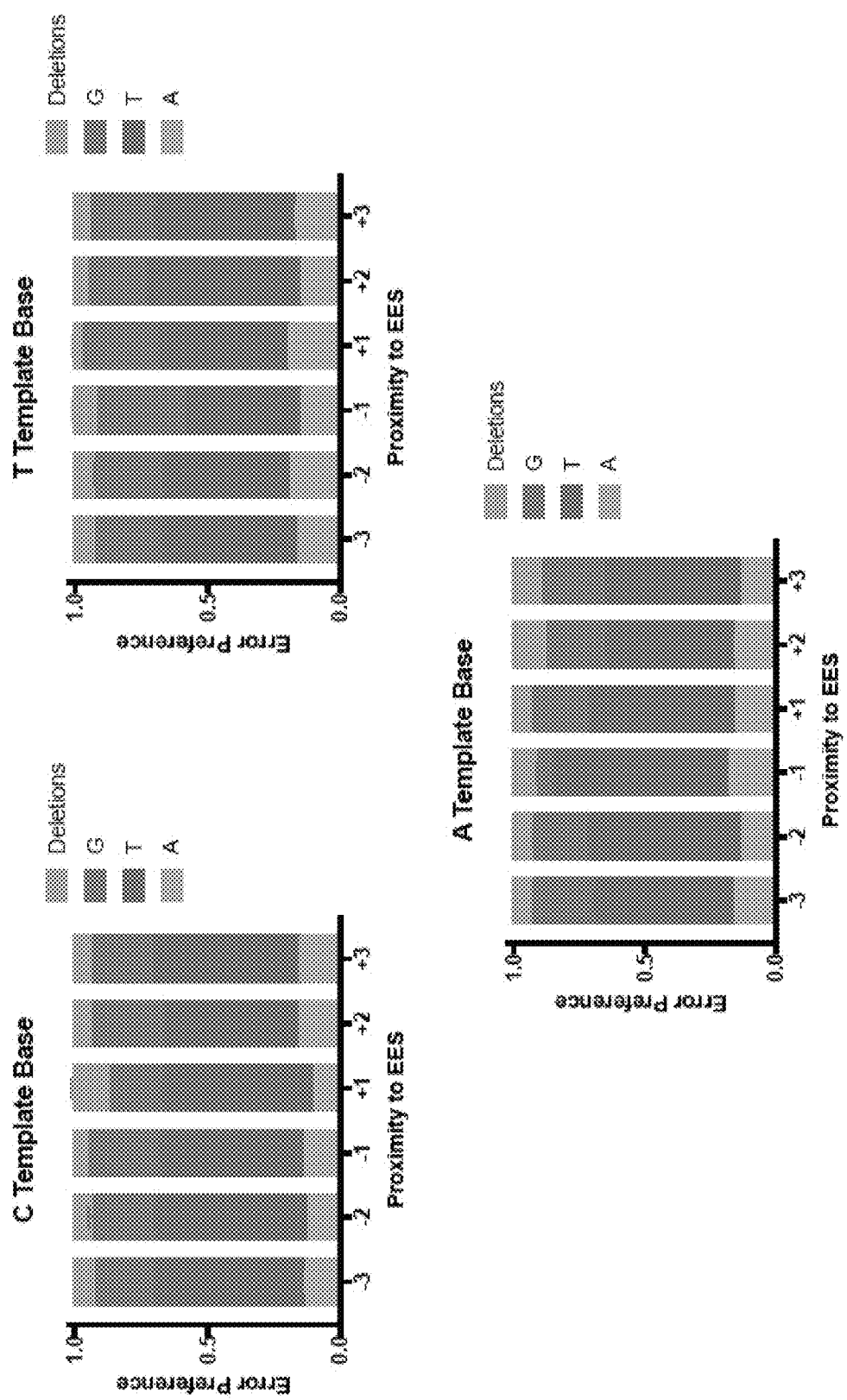

Correlation between error rates that were measured using a variety of fidelity assays and $FC_{50}$ outputs established assay fidelity readouts as biologically relevant. Analyses of $FC_{50}$ sensitivity (FIG. 8) and error rate variability between replicates (FIG. 9) for all five DNA polymerases copying in all four template contexts further established assay robustness and sensitivity.

Figure 4A:
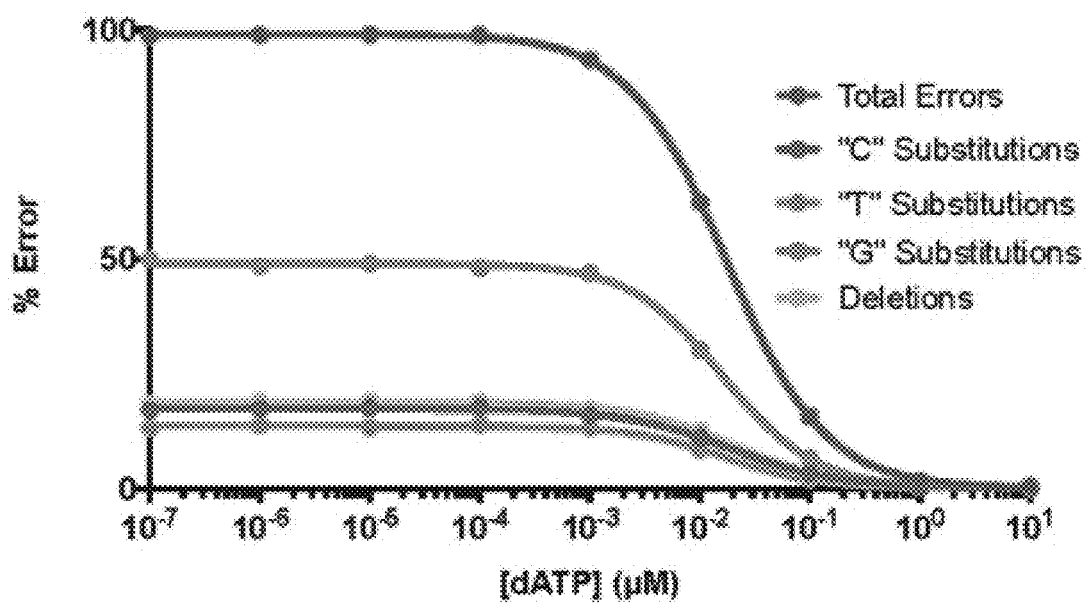
FIGS. 4A-4D: High-resolution Dpo4 fidelity profiles. Rare base titration curves are shown for Dpo4 copying in a FIG. 4A for "T" template context, FIG. 4B for "A" template context, FIG. 4C for "C" template context, and FIG. 4D for "G" template context. Preferred error type (nucleotide substitutions and deletions) is quantified for Dpo4 synthesizing in all four template contexts. Total error represents the sum of all error types. Values are the average of two experiments. Standard deviation error bars (n=2) are smaller than data points.
Figure 4B:
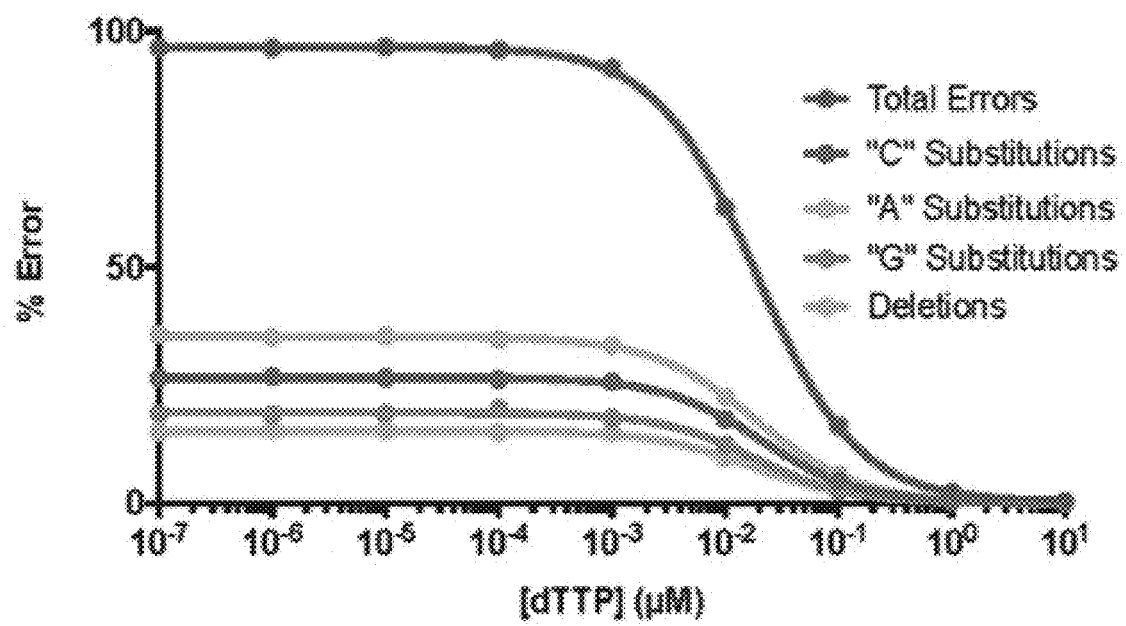
Figure 4C:
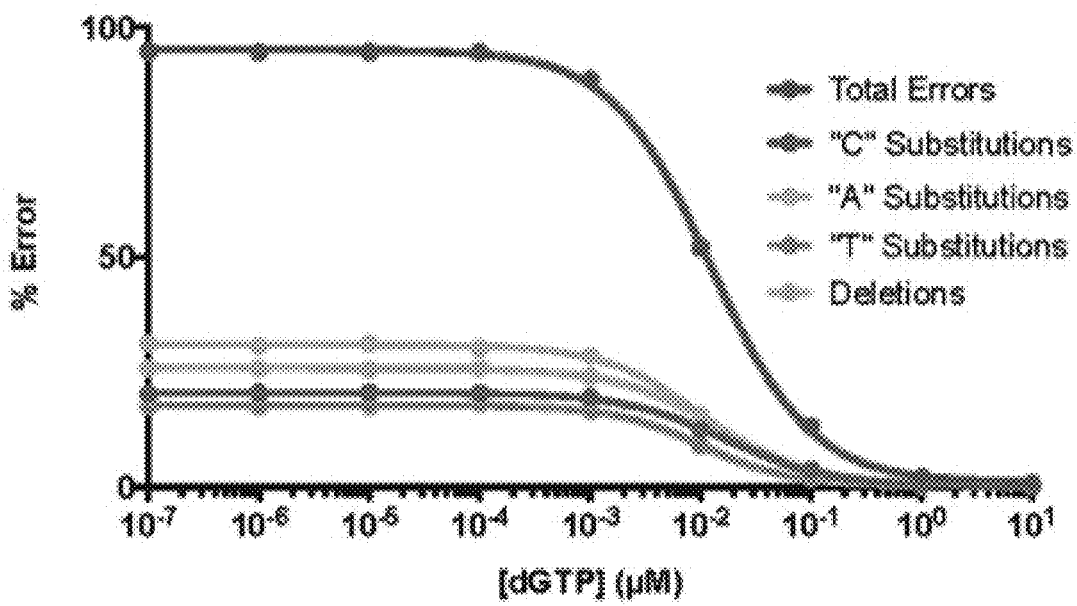
Figure 4D:
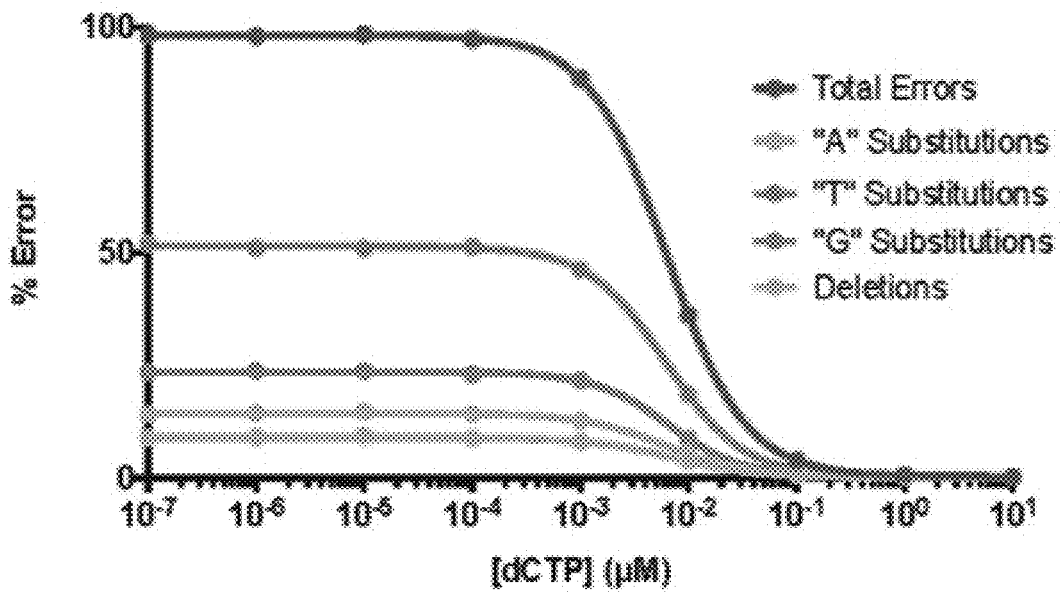
Figure 5A:
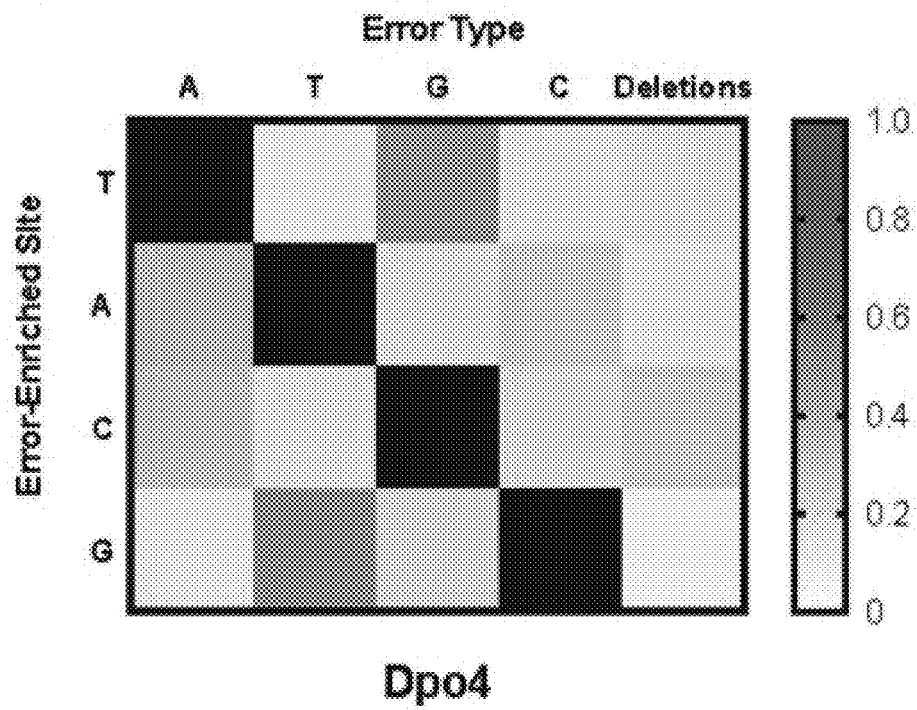
FIGS. 5A-5E: DNA polymerase error preferences. Heat maps reflect nucleotide substitution and deletion preferences of Dpo4 in FIG. 5A, Taq in FIG. 5B, Sequenase 2.0 in FIG. 5C, AMV RT in FIG. 5D, and Phi29 if FIG. 5E, copying in "T", "A", "C", and "G" template contexts. Error fraction was determined by normalizing individual error subtype frequencies to the total error rate measured at the lowest [dRTP] tested ($10^{-7}$ µM) for each template context. Values are the average of two experiments.
Figure 5B:
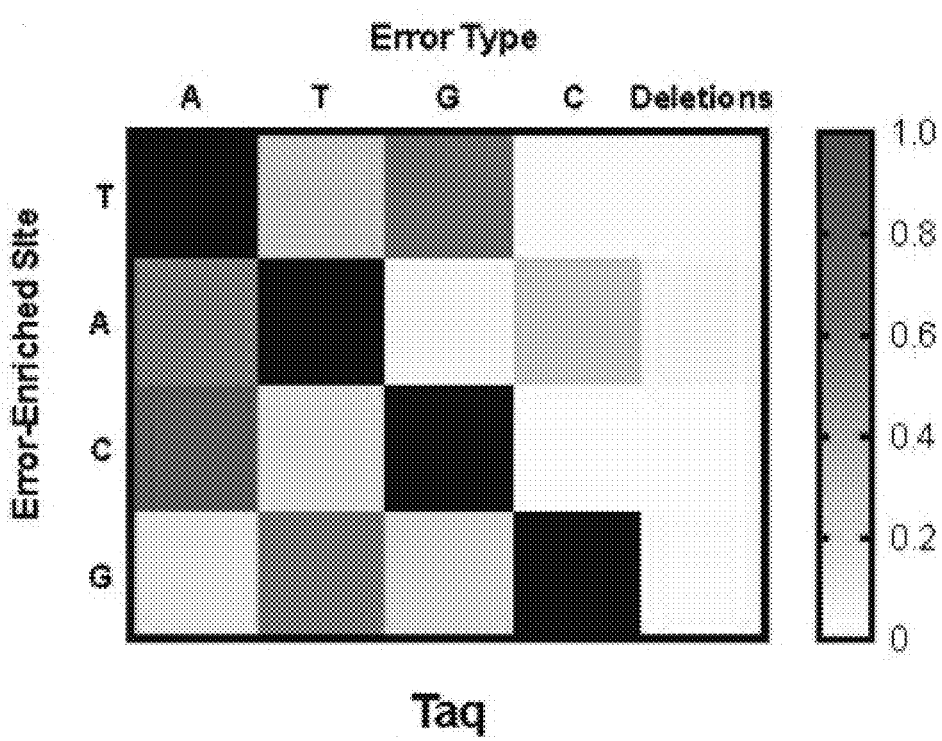
Figure 5C:
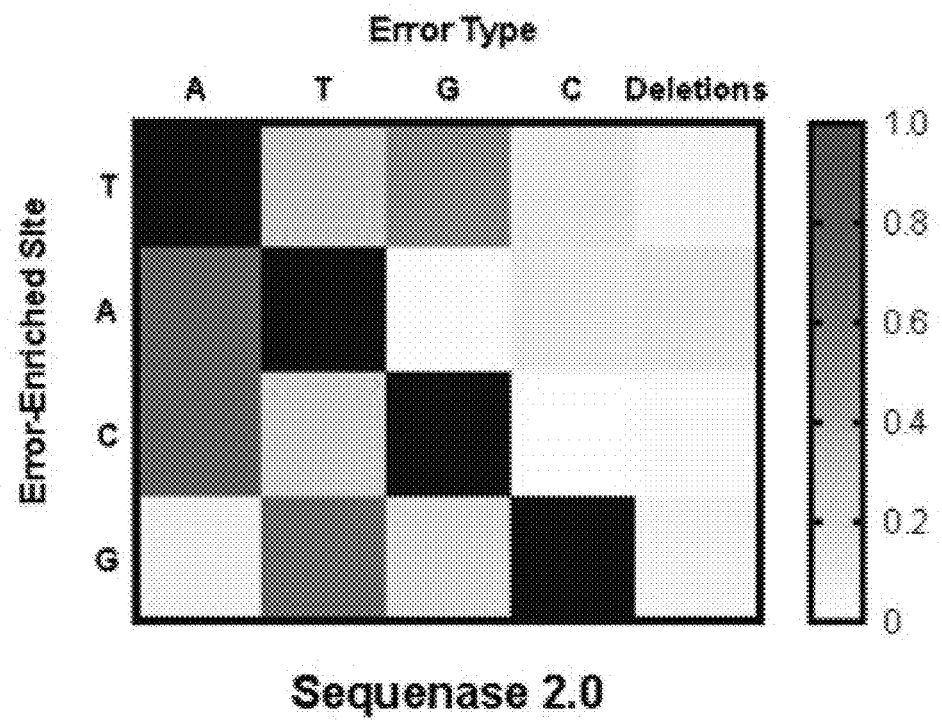
Figure 5D:
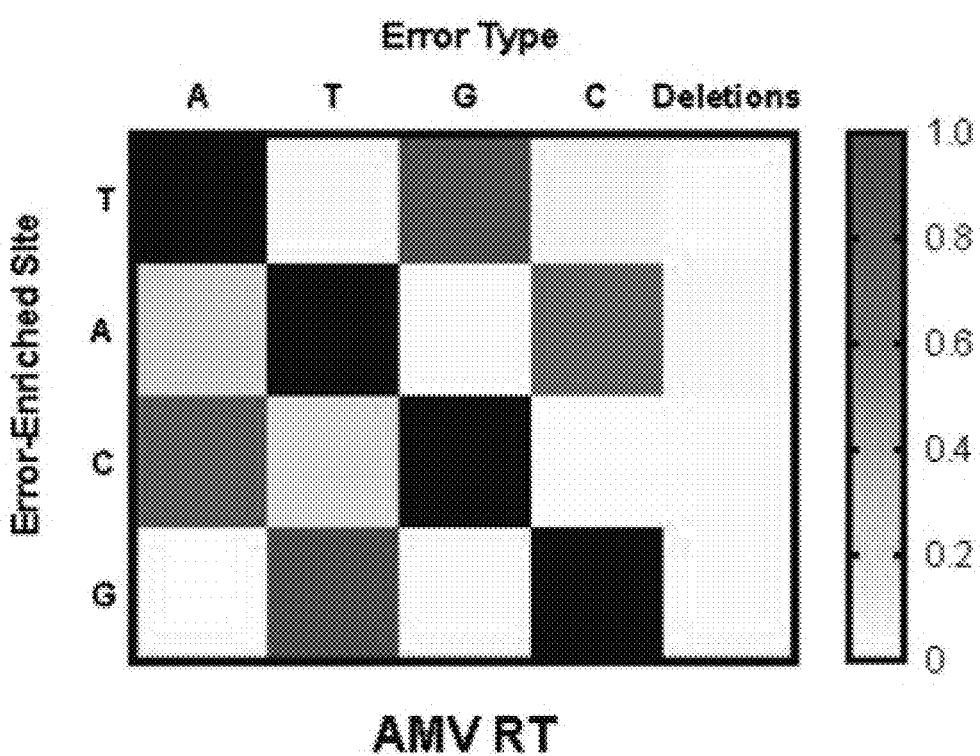
Figure 5E:
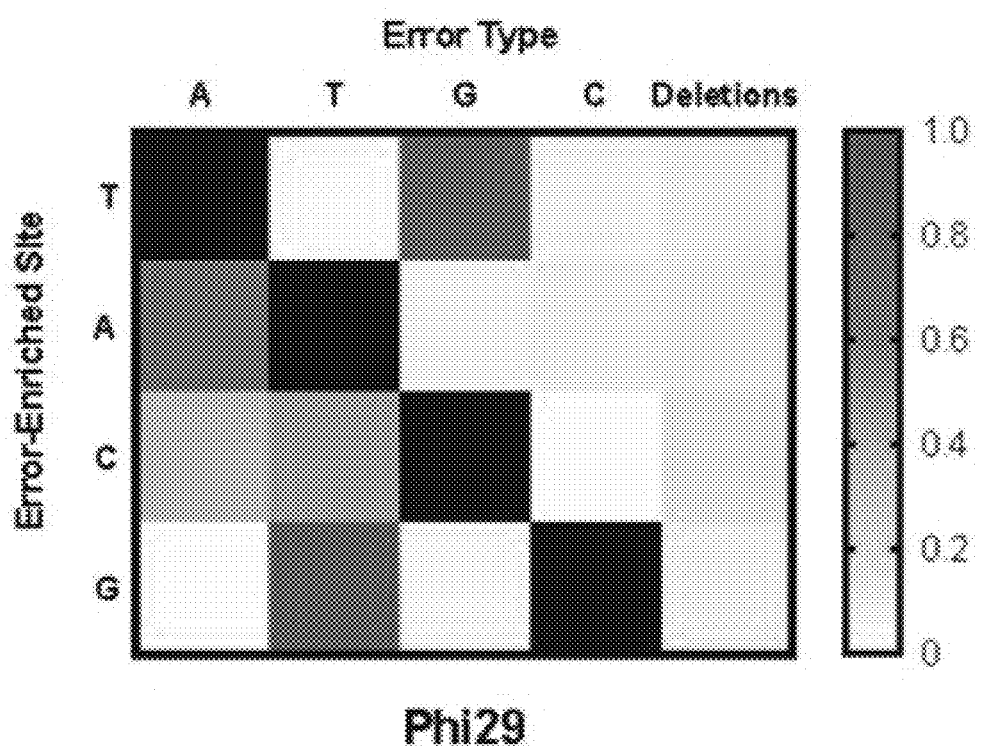

Nucleotide Imbalance Fidelity Assay Resolves DNA Polymerase Base Substitution and Deletion Preferences Sequencing data from each set of rare base conditions revealed high-resolution information on DNA polymerase fidelity preferences. In-depth fidelity profiles were calculated of Dpo4 copying in all four rare base contexts: "T" template (FIG. 4A), "A" template (FIG. 4B), "C" template (FIG. 4C), and "G" template (FIG. 4D). Each profile serves as a fidelity fingerprint, revealing polymerase mutation preferences by displaying the fraction of base substitutions and deletions (e.g., single nucleotide deletions) that were created. When copying a "T" template, Dpo4 favored T:dGTP substitutions over other error types. Similarly, in a "G" template context, Dpo4 preferentially created G:dTTP mismatches. A:dATP and C:dATP substitutions were only marginally preferred in "A" template and "C" template contexts, respectively. A study that measured all 12 base substitution rates for Sulfolobus solfataricus Dpo4, a close homologue of S. islandicus Dpo4, reported the following error preferences: T:dGTP>T:dCTP T:dTTP at T sites, A:dATP>A:dCTP>A:dGTP at A sites, G:dTTP>G:dGTP>G:dATP at G sites, and C:dCTP>C:dATP=C:dTTP at C sites (Ref. 41; herein incorporated by reference in its entirety). Similar trends were observed with S. islandicus Dpo4, with the exception of a slight preference for C:dATP over nearly equivalent C:dCTP and C:dTTP mispairs. Another report that measured S. solfataricus Dpo4 error preferences further corroborated these findings (Ref. 28; herein incorporated by reference in its entirety). High-resolution profiles for other DNA polymerases are shown in FIG. 10A-D.

For all DNA polymerases, error preference was quantified as the fraction of total errors that resulted in a particular error type (e.g., a specific base substitution or deletion (e.g., single nucleotide deletion)) at the lowest rare base concentration tested (since the lowest [dRTP] produced the largest error response) (FIG. 5A-5E). Consistent with past reports, Dpo4 was found to have a higher average deletion error rate than DNA polymerases from other families (e.g., A, B, RT) (Refs. 41-43; herein incorporated by reference in their entireties). Dpo4 also displayed the highest C:dCTP substitution rate, a typically rare mutation that almost never occurred with the other polymerases tested (Refs. 10, 41; herein incorporated by reference in their entireties). In general, Dpo4 errors were more evenly distributed across all possible error subtypes compared to the higher fidelity polymerases measured. The breakdown of error type at different template sites varied with the DNA polymerase. At "T" and "G" template sites, all polymerases made dominant T:dGTP and G:dTTP substitutions, respectively. At "A" template sites, all DNA polymerases preferentially misincorporated A:dATP with the exception of AMV RT, which preferred to make A:dCTP substitutions. At "C" template sites, all DNA polymerases except for Phi29 created preferential C:dATP mispairs. Phi29 displayed a marginal preference for C:dTTP mismatches. Overall, it was found that nucleotide imbalance fidelity assay data comprehensively reveals DNA polymerase error preferences at all possible bases, recapitulating past findings and uncovering new insights into DNA polymerase fidelity tendencies.

Nucleotide Imbalance Fidelity Assay Reveals Sequence Context Effects on Fidelity It is well established that template sequence context can impact DNA polymerase fidelity (Refs. 9, 10, 15-17; herein incorporated by reference in their entireties). Experiments were conducted during development of embodiments herein to examine the effect of neighboring bases on DNA polymerase error rates and error preferences. To examine the effects of sequence context on error rate decisions, each template type was designed to contain six degenerate base positions (−3, −2, −1, +1, +2, +3) flanking the EES (FIG. 1B, Table 2). Each resulting template library consisted of 729 unique 6-base combinations surrounding the EES and allowed thorough investigation of the positional effect of base identity on DNA polymerase error tendencies. For a given rare base context, position-dependent error rates were calculated by grouping sequencing readouts that shared the same base identity at the −3, −2, −1, +1, +2, or +3 positions. Sequence context-fixed error rates were then fit to obtain $FC_{50}$ values.

Figure 6A:
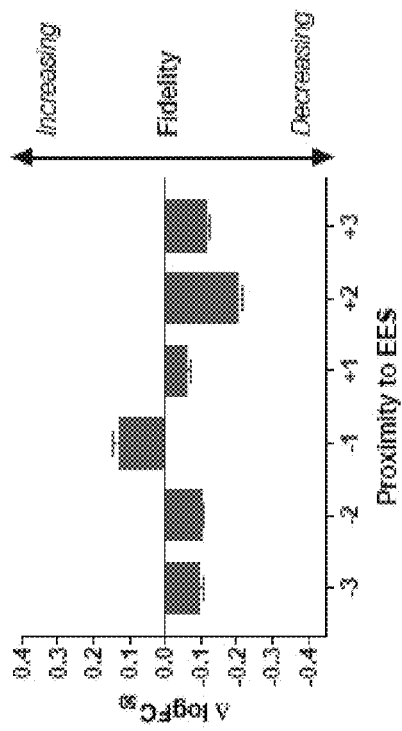
Figure 6A:
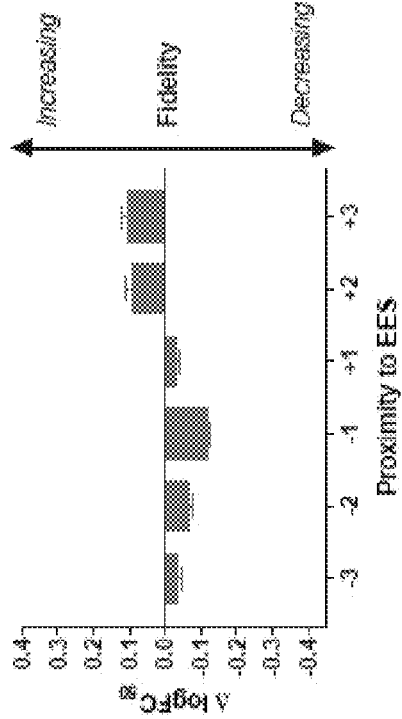
Figure 6A:
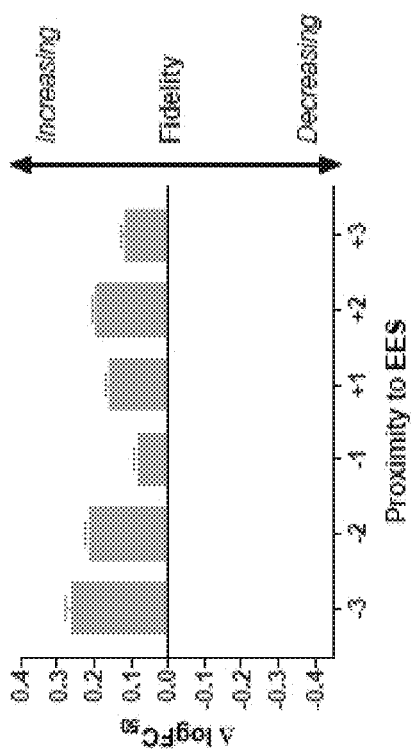

To determine whether sequence context could substantially impact the $FC_{50}$ readout, the extent to which sequence context-specific $FC_{50}$ values deviated from the average $FC_{50}$ of a given template library was calculated. For each DNA polymerase and template library, the change in $FC_{50}$ (log $FC_{50}$_Average−log $FC_{50}$_Fixed Template Base) was calculated for a given template base at each position surrounding the EES (FIGS. 11-15). Results showed that the −3, −2, −1, +1, +2, and +3 base identities and positions could modulate changes in $FC_{50}$ that indicated either increased or decreased fidelity. For example, when Phi29 replicated a VVVTVVV template library (FIG. 6A), G and C template bases could increase or decrease fidelity depending on their proximity to the EES, whereas A template bases consistently increased fidelity regardless of position. Further, template-mediated fold-changes in $FC_{50}$ as large as 2-fold were observed in both directions. For Dpo4, a +1 G in a DDDCDDD context led to a 2-fold increase in $FC_{50}$, signifying lower fidelity, whereas a +1 A in the same context yielded a −2-fold decrease in $FC_{50}$, indicating higher fidelity (FIG. 15). These data support error rate modulation by sequence context and furthermore demonstrate the sensitivity of the $FC_{50}$ metric to sequence-driven changes in DNA polymerase fidelity.

Apart from modulating $FC_{50}$, sequence context in certain cases also had an effect on the total error response (defined as the error rate measured at the lowest [dRTP] tested) that a DNA polymerase could create within a given rare base context (FIGS. 16-20). For example, Phi29's total error depended substantially on sequence context when replicating DDDCDDD and HHHGHHH template libraries (FIG. 6B). With a couple of exceptions, total error tended to increase with surrounding C and G template bases and decrease with surrounding A and T template bases. Such observations corroborate past reports that A+T-richness at the primer terminus helps to improve strand separation and therefore increase proofreading efficiency (Refs. 9, 47-50; herein incorporated by reference in their entireties), enabling higher fidelity outcomes for polymerases such as Phi29 bearing 3'-5' exonuclease activity.

Figure 6C:
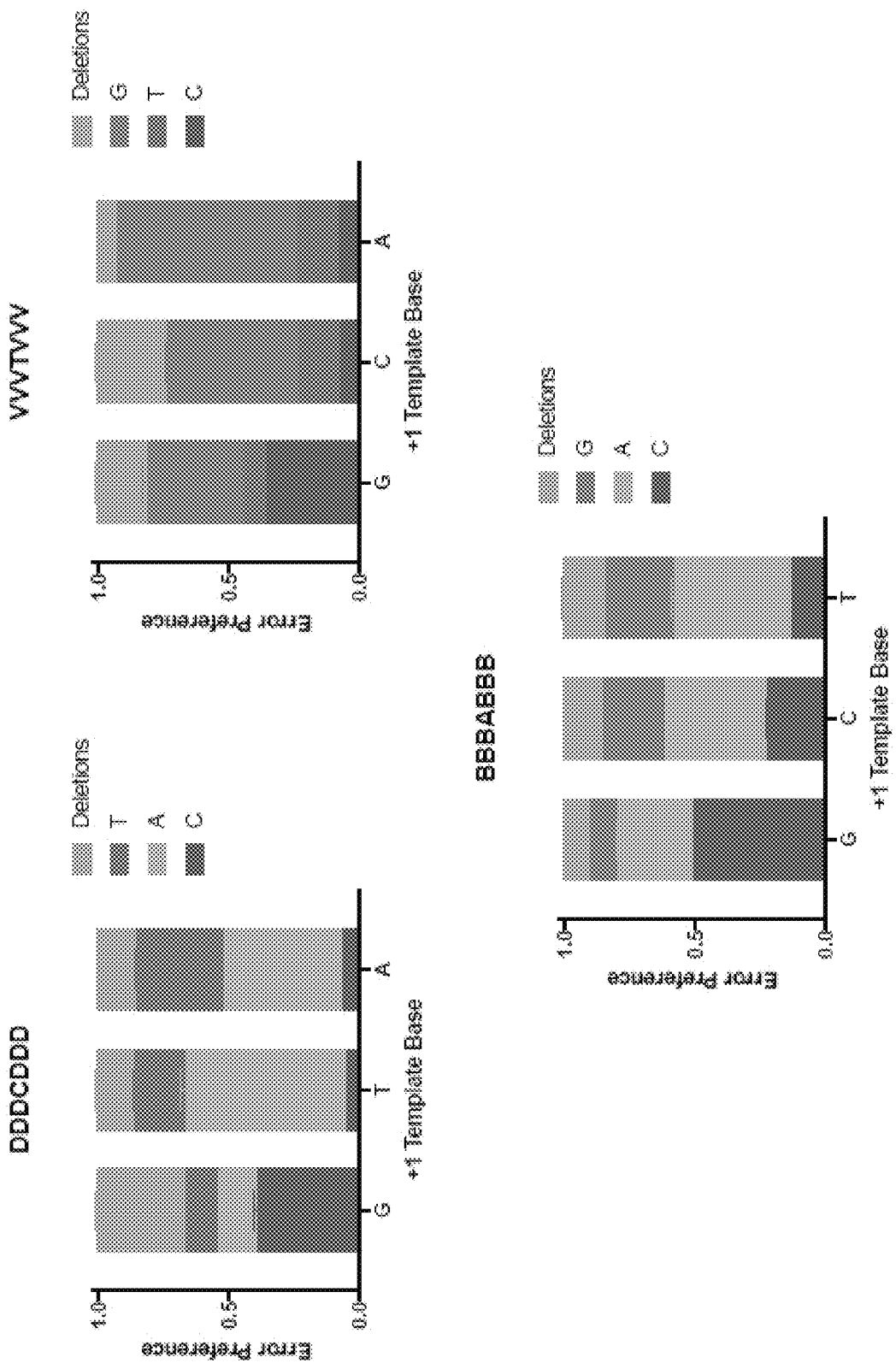

Experiments were conducted during development of embodiments herein to determine whether DNA polymerase error preference is modulated by the identity and position of neighboring template bases. Similar to before, error preference was determined by normalizing error subtype frequencies to total error rate at the lowest rare base concentration tested. For most DNA polymerases studied, it was found that base identity at the −1 template position tended to affect the preferred error distribution at the EES (FIGS. 21A-24D). For example, a −1 G in a DDDCDDD context led to Phi29 preferentially producing C:dATP errors, whereas a −1 T in the same context yielded dominant C:dTTP errors (FIG. 23A-23D). In contrast, it was found that Dpo4 error preferences were predominantly modulated by the +1 template base position (FIG. 25A-25D). For instance, in a DDDCDDD context, when the +1 base was A or T, Dpo4 predominantly misincorporated C:dATP, however, when the +1 base was G, Dpo4 error preference shifted to C:dCTP and deletions (e.g., single nucleotide deletions) also increased (FIG. 6C). This phenomenon, attributed to active site misalignment of Dpo4, has been previously reported to explain the unusually high rate of C:dCTP and deletion mutations in this particular sequence context (Refs. 41, 43; herein incorporated by reference in their entireties). +1 G-mediated increases in T:dCTP and A:dCTP rates were also observed when Dpo4 replicated in VVVTVVV and BBBABBB contexts, respectively (FIG. 6C), further supporting a misalignment mechanism (Ref 41; herein incorporated by reference in its entirety). Overall, sequence context data collectively point to the strong influence template base position and identity can exert on DNA polymerase fidelity decisions.

REFERENCES

The following references, some of which are cited above by number, are herein incorporated by reference in their entireties.

1. Kunkel, T. A. and Bebenek, K. (2000) DNA replication fidelity. *Annu Rev Biochem*, 69, 497-529.
2. Ganai, R. A. and Johansson, E. (2016) DNA Replication-A Matter of Fidelity. *Mol Cell*, 62, 745-755.
3. Loh, E., Salk, J. J. and Loeb, L. A. (2010) Optimization of DNA polymerase mutation rates during bacterial evolution. *Proc Natl Acad Sci USA*, 107, 1154-1159.
4. Tomasetti, C., Li, L. and Vogelstein, B. (2017) Stem cell divisions, somatic mutations, cancer etiology, and cancer prevention. *Science*, 355, 1330-1334.
5. Lange, S. S., Takata, K. and Wood, R. D. (2011) DNA polymerases and cancer. *Nat Rev Cancer*, 11, 96-110.
6. Freudenthal, B. D., Beard, W. A., Shock, D. D. and Wilson, S. H. (2013) Observing a DNA polymerase choose right from wrong. *Cell*, 154, 157-168.
7. Hohlbein, J., Aigrain, L., Craggs, T. D., Bermek, O., Potapova, O., Shoolizadeh, P., Grindley, N. D., Joyce, C. M. and Kapanidis, A. N. (2013) Conformational landscapes of DNA polymerase I and mutator derivatives establish fidelity checkpoints for nucleotide insertion. *Nat Commun*, 4, 2131.
8. Zakour, R. A., Kunkel, T. A. and Loeb, L. A. (1981) Metal-induced infidelity of DNA synthesis. *Environ Health Perspect*, 40, 197-205.
9. Petruska, J. and Goodman, M. F. (1985) Influence of neighboring bases on DNA polymerase insertion and proofreading fidelity. *J Biol Chem*, 260, 7533-7539.
10. Mendelman, L. V., Boosalis, M. S., Petruska, J. and Goodman, M. F. (1989) Nearest neighbor influences on DNA polymerase insertion fidelity. *J Biol Chem*, 264, 14415-14423.
11. Mathews, C. K. (2006) DNA precursor metabolism and genomic stability. *FASEB J*, 20, 1300-1314.
12. McCulloch, S. D. and Kunkel, T. A. (2008) The fidelity of DNA synthesis by eukaryotic replicative and translesion synthesis polymerases. *Cell Res*, 18, 148-161.
13. Kunkel, T. A. (2009) Evolving views of DNA replication (in)fidelity. *Cold Spring Harb Symp Quant Biol*, 74, 91-101.
14. Jack, B. R., Leonard, S. P., Mishler, D. M., Renda, B. A., Leon, D., Suarez, G. A. and Barrick, J. E. (2015) Predicting the Genetic Stability of Engineered DNA Sequences with the EFM Calculator. *ACS Synth Biol*, 4, 939-943.
15. Schroeder, J. W., Hirst, W. G., Szewczyk, G. A. and Simmons, L. A. (2016) The Effect of Local Sequence Context on Mutational Bias of Genes Encoded on the Leading and Lagging Strands. *Curr Biol*, 26, 692-697.
16. Lujan, S. A., Clausen, A. R., Clark, A. B., MacAlpine, H. K., MacAlpine, D. M., Malc, E. P., Mieczkowski, P. A., Burkholder, A. B., Fargo, D. C., Gordenin, D. A. et al. (2014) Heterogeneous polymerase fidelity and mismatch repair bias genome variation and composition. *Genome Res*, 24, 1751-1764.
17. Sung, W., Ackerman, M. S., Gout, J. F., Miller, S. F., Williams, E., Foster, P. L. and Lynch, M. (2015) Asymmetric Context-Dependent Mutation Patterns Revealed through Mutation-Accumulation Experiments. *Mol Biol Evol*, 32, 1672-1683.

18. Keith, B. J., Jozwiakowski, S. K. and Connolly, B. A. (2013) A plasmid-based lacZalpha gene assay for DNA polymerase fidelity measurement. *Anal Biochem*, 433, 153-161.
19. Bebenek, K. and Kunkel, T. A. (1995) Analyzing fidelity of DNA polymerases. *Methods Enzymol*, 262, 217-232.
20. Tindall, K. R. and Kunkel, T. A. (1988) Fidelity of DNA synthesis by the Thermus aquaticus DNA polymerase. *Biochemistry*, 27, 6008-6013.
21. Cariello, N. F., Swenberg, J. A. and Skopek, T. R. (1991) Fidelity of *Thermococcus litoralis* DNA polymerase (Vent) in PCR determined by denaturing gradient gel electrophoresis. *Nucleic Acids Res*, 19, 4193-4198.
22. Keohavong, P. and Thilly, W. G. (1989) Fidelity of DNA polymerases in DNA amplification. *Proc Natl Acad Sci USA*, 86, 9253-9257.
23. Lee, D. F., Lu, J., Chang, S., Loparo, J. J. and Xie, X. S. (2016) Mapping DNA polymerase errors by single-molecule sequencing. *Nucleic Acids Res*, 44, e118.
24. Hestand, M. S., Van Houdt, J., Cristofoli, F. and Vermeesch, J. R. (2016) Polymerase specific error rates and profiles identified by single molecule sequencing. *Mutat Res*, 784-785, 39-45.
25. Gregory, M. T., Bertout, J. A., Ericson, N. G., Taylor, S. D., Mukherjee, R., Robins, H. S., Drescher, C. W. and Bielas, J. H. (2016) Targeted single molecule mutation detection with massively parallel sequencing. *Nucleic Acids Res*, 44, e22.
26. Kinde, I., Wu, J., Papadopoulos, N., Kinzler, K. W. and Vogelstein, B. (2011) Detection and quantification of rare mutations with massively parallel sequencing. *Proc Natl Acad Sci USA*, 108, 9530-9535.
27. Schmitt, M. W., Kennedy, S. R., Salk, J. J., Fox, E. J., Hiatt, J. B. and Loeb, L. A. (2012) Detection of ultra-rare mutations by next-generation sequencing. *Proc Natl Acad Sci USA*, 109, 14508-14513.
28. Zamft, B. M., Marblestone, A. H., Kording, K., Schmidt, D., Martin-Alarcon, D., Tyo, K., Boyden, E. S. and Church, G. (2012) Measuring cation dependent DNA polymerase fidelity landscapes by deep sequencing. *PLoS One*, 7, e43876.
29. Kunz, B. A., Kohalmi, S. E., Kunkel, T. A., Mathews, C. K., McIntosh, E. M. and Reidy, J. A. (1994) International Commission for Protection Against Environmental Mutagens and Carcinogens. Deoxyribonucleoside triphosphate levels: a critical factor in the maintenance of genetic stability. *Mutat Res*, 318, 1-64.
30. Bebenek, K., Roberts, J. D. and Kunkel, T. A. (1992) The effects of dNTP pool imbalances on frameshift fidelity during DNA replication. *J Biol Chem*, 267, 3589-3596.
31. Echols, H. and Goodman, M. F. (1991) Fidelity mechanisms in DNA replication. *Annu Rev Biochem*, 60, 477-511.
32. Baldwin, J. E., Martin, S. L. and Sutherland, J. D. (1991) Site-specific forced misincorporation mutagenesis using modified T7 DNA polymerase. *Protein Eng*, 4, 579-584.
33. Spee, J. H., de Vos, W. M. and Kuipers, O. P. (1993) Efficient random mutagenesis method with adjustable mutation frequency by use of PCR and dITP. *Nucleic Acids Res*, 21, 777-778.
34. Liao, X. B. and Wise, J. A. (1990) A simple high-efficiency method for random mutagenesis of cloned genes using forced nucleotide misincorporation. *Gene*, 88, 107-111.
35. Bertram, J. G., Oertell, K., Petruska, J. and Goodman, M. F. (2010) DNA polymerase fidelity: comparing direct competition of right and wrong dNTP substrates with steady state and pre-steady state kinetics. *Biochemistry*, 49, 20-28.
36. Creighton, S., Bloom, L. B. and Goodman, M. F. (1995) Gel fidelity assay measuring nucleotide misinsertion, exonucleolytic proofreading, and lesion bypass efficiencies. *Methods Enzymol*, 262, 232-256.
37. Sinha, N. K. and Haimes, M. D. (1981) Molecular mechanisms of substitution mutagenesis. An experimental test of the Watson-Crick and topal-fresco models of base mispairings. *J Biol Chem*, 256, 10671-10683.
38. Caporaso, J. G., Lauber, C. L., Walters, W. A., Berg-Lyons, D., Huntley, J., Fierer, N., Owens, S. M., Betley, J., Fraser, L., Bauer, M. et al. (2012) Ultra-high-throughput microbial community analysis on the Illumina HiSeq and MiSeq platforms. *ISME J*, 6, 1621-1624.
39. Needleman, S. B. and Wunsch, C. D. (1970) A general method applicable to the search for similarities in the amino acid sequence of two proteins. *J Mol Biol*, 48, 443-453.
40. Rice, P., Longden, I. and Bleasby, A. (2000) EMBOSS: the European Molecular Biology Open Software Suite. *Trends Genet*, 16, 276-277.
41. Kokoska, R. J., Bebenek, K., Boudsocq, F., Woodgate, R. and Kunkel, T. A. (2002) Low fidelity DNA synthesis by a y family DNA polymerase due to misalignment in the active site. *J Biol Chem*, 277, 19633-19638.
42. Pata, J. D. (2010) Structural diversity of the Y-family DNA polymerases. *Biochim Biophys Acta*, 1804, 1124-1135.
43. Wu, Y., Wilson, R. C. and Pata, J. D. (2011) The Y-family DNA polymerase Dpo4 uses a template slippage mechanism to create single-base deletions. *J Bacteriol*, 193, 2630-2636.
44. Nelson, J. R., Cai, Y. C., Giesler, T. L., Farchaus, J. W., Sundaram, S. T., Ortiz-Rivera, M., Hosta, L. P., Hewitt, P. L., Mamone, J. A., Palaniappan, C. et al. (2002) TempliPhi, phi29 DNA polymerase based rolling circle amplification of templates for DNA sequencing. *Biotechniques, Suppl*, 44-47.
45. Paez, J. G., Lin, M., Beroukhim, R., Lee, J. C., Zhao, X., Richter, D. J., Gabriel, S., Herman, P., Sasaki, H., Altshuler, D. et al. (2004) Genome coverage and sequence fidelity of phi29 polymerase-based multiple strand displacement whole genome amplification. *Nucleic Acids Res*, 32, e71.
46. Esteban, J. A., Salas, M. and Blanco, L. (1993) Fidelity of phi 29 DNA polymerase. Comparison between protein-primed initiation and DNA polymerization. *J Biol Chem*, 268, 2719-2726.
47. Reha-Krantz, L. J., Woodgate, S. and Goodman, M. F. (2014) Engineering processive DNA polymerases with maximum benefit at minimum cost. *Front Microbiol*, 5, 380.
48. Bloom, L. B., Otto, M. R., Eritja, R., Reha-Krantz, L. J., Goodman, M. F. and Beechem, J. M. (1994) Pre-steady-state kinetic analysis of sequence-dependent nucleotide excision by the 3'-exonuclease activity of bacteriophage T4 DNA polymerase. *Biochemistry*, 33, 7576-7586.
49. Reha-Krantz, L. J. (2010) DNA polymerase proofreading: Multiple roles maintain genome stability. *Biochim Biophys Acta*, 1804, 1049-1063.
50. Bessman, M. J. and Reha-Krantz, L. J. (1977) Studies on the biochemical basis of spontaneous mutation. V. Effect of temperature on mutation frequency. *J Mol Biol*, 116, 115-123.

51. Garcia-Diaz, M. and Bebenek, K. (2007) Multiple functions of DNA polymerases. *CRC Crit Rev Plant Sci,* 26, 105-122.

52. Rittie, L. and Perbal, B. (2008) Enzymes used in molecular biology: a useful guide. *J Cell Commun Signal,* 2, 25-45.

53. Goodwin, S., McPherson, J. D. and McCombie, W. R. (2016) Coming of age: ten years of next-generation sequencing technologies. *Nat Rev Genet,* 17, 333-351.

54. Eckert, K. A. and Kunkel, T. A. (1991) DNA polymerase fidelity and the polymerase chain reaction. *Genome Research,* 1, 17-24.

55. Koag, M. C., Nam, K. and Lee, S. (2014) The spontaneous replication error and the mismatch discrimination mechanisms of human DNA polymerase beta. *Nucleic Acids Res,* 42, 11233-11245.

56. Boutabout, M., Wilhelm, M. and Wilhelm, F. X. (2001) DNA synthesis fidelity by the reverse transcriptase of the yeast retrotransposon Ty1. *Nucleic Acids Res,* 29, 2217-2222.

57. Yu, H. and Goodman, M. F. (1992) Comparison of HIV-1 and avian myeloblastosis virus reverse transcriptase fidelity on RNA and DNA templates. *J Biol Chem,* 267, 10888-10896.

58. Taube, R., Avidan, O., Bakhanashvili, M. and Hizi, A. (1998) DNA synthesis exhibited by the reverse transcriptase of mouse mammary tumor virus: processivity and fidelity of misinsertion and mispair extension. *Eur J Biochem,* 258, 1032-1039.

59. Erlich, Y. and Zielinski, D. (2017) DNA Fountain enables a robust and efficient storage architecture. *Science,* 355, 950-954.

60. Camps, M., Naukkarinen, J., Johnson, B. P. and Loeb, L. A. (2003) Targeted gene evolution in Escherichia coli using a highly error-prone DNA polymerase I. *Proc Natl Acad Sci USA,* 100, 9727-9732.

61. Ellefson, J. W., Gollihar, J., Shroff, R., Shivram, H., Iyer, V. R. and Ellington, A. D. (2016) Synthetic evolutionary origin of a proofreading reverse transcriptase. *Science,* 352, 1590-1593.

62. Rogozin, I. B. and Pavlov, Y. I. (2003) Theoretical analysis of mutation hotspots and their DNA sequence context specificity. *Mutat Res,* 544, 65-85.

---

The invention claimed is:

1. A method comprising:
   (a) contacting a polymerase with:
      (i) a synthetic sequence library comprising at least one synthetic nucleic acid template comprising an error-enriched site (EES), wherein the at least one synthetic nucleic acid template comprises a sequence selected from:
      VVVT/UVVV, wherein T/U is the EES;
      BBBABBB, wherein A is the EES;
      DDDCDDD, wherein C is the EES; and
      HHHGHHH, wherein G is the EES; and
      wherein each V independently represents A, C, or G; each B independently represents C, G, or T/U; each D independently represents A, G or T/U; and each H independently represents A, C, or T/U; and (ii) nucleoside triphosphates (NTPs) that are complementary to the at least one synthetic nucleic acid template for the four nucleotide types, wherein the complementary NTP that is complementary to the EES is present at lower concentration than the NTPs that are complementary to the other nucleotides in the at least one synthetic nucleic acid template;

(b) allowing the polymerase to synthesize a new nucleic acid strand from the at least one synthetic nucleic acid template and NTPs;
(c) monitoring replication/synthesis errors at the EES; and
(d) repeating steps (a) through (c) with varied concentrations of the NTP that is complementary to the EES.

2. The method of claim 1, wherein replication/synthesis errors are monitored by nucleic acid sequencing.

3. The method of claim 2, wherein replication/synthesis errors at the EES are monitored by a next-generation sequencing (NGS) technique.

4. The method of claim 2, wherein replication/synthesis errors at the EES are monitored by a single-molecule sequencing technique.

5. The method of claim 1, wherein the at least one synthetic nucleic acid template is deoxyribonucleic acid (DNA) or ribonucleic acid (RNA).

6. The method of claim 1, wherein the NTPs are deoxyribonucleoside triphosphates (dNTPs) and the new nucleic acid strand is a DNA strand or ribonucleotides (rNTPs) and the new nucleic acid strand is an RNA strand.

7. The method of claim 1, wherein the polymerase is a DNA polymerase.

8. The method of claim 1, wherein the nucleotide type present at the EES is present at 5% or fewer of the positions of the nucleic acid template.

9. The method of claim 8, wherein the nucleotide type present at the EES is not present elsewhere in the nucleic acid template.

10. The method of claim 1, wherein the complementary NTPs for the primary nucleotide types are present at concentrations between 10 and $10^9$ greater than the complementary NTP for the EES.

11. The method of claim 1, wherein a replication/synthesis error results in one or more substitutions in the new nucleic acid strand.

12. The method of claim 1, further comprising:
(e) determining the concentration of the complementary NTP for the EES at which the polymerase makes a replication/synthesis error at the EES 50% of the time.

13. A method comprising performing the steps of claim 1 for separate synthetic nucleic acid templates comprising each of the four nucleotide types at the EES.

14. The method of claim 13, wherein said method comprises four separate reactions, each of which comprises a single one of each of the four nucleotide types at the EES.

15. The method of claim 1, wherein at least one said template comprises a plurality of different templates, wherein each of said templates comprises different nucleic acid sequences flanking said EES.

16. The method of claim 15, wherein said flanking sequence comprises 1 to 3 nucleotides on one or both sides of said EES.

17. The method of claim 1, wherein the polymerase is a RNA polymerase.

18. The method of claim 1, wherein the polymerase is a reverse transcriptase.

19. The method of claim 1, wherein a replication/synthesis error results in one or more insertions in the new nucleic acid strand.

20. The method of claim 1, wherein a replication/synthesis error results in one or more deletions in the new nucleic acid strand.

21. A method comprising:
(a) contacting a polymerase with:
at least one synthetic nucleic acid template that is at least 20 nucleotides in length and comprises three out of four of: (1) adenine (A), (2) cytosine (C), (3) guanine (G), and (4) thymine (T) or uracil (U) as primary nucleotide types, and an error-enriched site (EES) that comprises a fourth nucleotide type that is not one of the primary nucleotide types, wherein the nucleotide type of the EES represents 5% or fewer of the total nucleotides of the at least one synthetic nucleic acid template; and
(ii) nucleoside triphosphates (NTPs) for the four nucleotide types, wherein the complementary NTP for the EES is present at lower concentration than the complementary NTPs for the primary nucleotide types of the at least one synthetic nucleic acid template;
(b) allowing the polymerase to synthesize a new nucleic acid strand from the at least one synthetic nucleic acid template and NTPs;
(c) monitoring replication/synthesis errors at the EES; and
(d) repeating steps (a) through (c) with varied concentrations of the complementary NTP for the EES.

22. The method of claim 21, wherein replication/synthesis errors are monitored by nucleic acid sequencing.

23. The method of claim 22, wherein replication/synthesis errors at the EES are monitored by a next-generation sequencing (NGS) technique.

24. The method of claim 22, wherein replication/synthesis errors at the EES are monitored by a single-molecule sequencing technique.

25. The method of claim 21, wherein the at least one synthetic nucleic acid template is deoxyribonucleic acid (DNA) or ribonucleic acid (RNA).

26. The method of claim 21, wherein the NTPs are deoxyribonucleoside triphosphates (dNTPs) and the new nucleic acid strand is a DNA strand or ribonucleotides (rNTPs) and the new nucleic acid strand is an RNA strand.

27. The method of claim 21, wherein the polymerase is a DNA polymerase.

28. The method of claim 21, wherein the polymerase is a RNA polymerase.

29. The method of claim 21, wherein the polymerase is a reverse transcriptase.

30. The method of claim 21, wherein the nucleotide type present at the EES is not present elsewhere in the at least one synthetic nucleic acid template.

31. The method of claim 21, wherein the complementary NTPs for the primary nucleotide types are present at concentrations between 10 and $10^9$ greater than the complementary NTP for the EES.

32. The method of claim 21, wherein a replication/synthesis error results in one or more substitutions in the new nucleic acid strand.

33. The method of claim 21, further comprising:
(e) determining the concentration of the complementary NTP for the EES at which the polymerase makes a replication/synthesis error at the EES 50% of the time.

34. The method of claim 21, wherein at least one said synthetic nucleic acid template comprises a plurality of different synthetic templates, wherein each of said synthetic templates comprises different nucleic acid sequences flanking said EES.

35. The method of claim 21, wherein said flanking sequence comprises 1 to 3 nucleotides on one or both sides of said EES.

36. A method comprising performing the steps of claim 21 for separate nucleic acid synthetic templates comprising each of the four nucleotide types at the EES.

37. The method of claim 36, wherein said method comprises four separate reactions, each of which comprises a single one of each of the four nucleotide types at the EES.

\* \* \* \* \*